United States Patent
Gonzalez, Jr. et al.

(10) Patent No.: US 9,470,680 B2
(45) Date of Patent: Oct. 18, 2016

(54) FLUORESCENCE-BASED APPROACH TO MONITOR RELEASE FACTOR-CATALYZED TERMINATION OF PROTEIN SYNTHESIS

(75) Inventors: Ruben L. Gonzalez, Jr., New York, NY (US); Samuel H. Sternberg, Lancaster, PA (US); Dileep K. Pulukkunat, New York, NY (US)

(73) Assignee: THE TRUSTEES OF COLUMBIA UNIVERSITY IN THE CITY OF NEW YORK, New York, NY (US)

(*) Notice: Subject to any disclaimer, the term of this patent is extended or adjusted under 35 U.S.C. 154(b) by 319 days.

(21) Appl. No.: 13/407,438

(22) Filed: Feb. 28, 2012

(65) Prior Publication Data
US 2013/0034914 A1 Feb. 7, 2013

Related U.S. Application Data

(60) Provisional application No. 61/447,646, filed on Feb. 28, 2011.

(51) Int. Cl.
*G01N 33/542* (2006.01)
(52) U.S. Cl.
CPC ................... *G01N 33/542* (2013.01)
(58) Field of Classification Search
CPC ..... C12P 21/02; C12P 21/64; C12P 21/6428; C12R 1/01
See application file for complete search history.

(56) References Cited

PUBLICATIONS

Nakahigashi et al., HemK, a class of protein methyl transferase with similarity to DNA methyl transferases, methylates polypeptide chain release factors, and hemK knockout induces defects in translational termination., PNAS (2002), vol. 99, pp. 1473-1478.*
BioTek (2006).*
Iwunze., The characterization of the fluorescence of I-histidine in simulated body fluid., Journal of Photochemistry and Photobiology A: Chemistry (2007), vol. 186, pp. 283-289.*
Sternberg et al., Translation factors direct intrinsic ribosome dynamics during translation termination and ribosome recycling., Nature Structural & Molecular Biology (Epub Jul. 13, 2009), vol. 16, pp. 861-868.*
Agirrezabala, X. et al., "Visualization of the hybrid state of tRNA binding promoted by spontaneous ratcheting of the ribosome," Mol. Cell, vol. 32, pp. 190-197 (Oct. 24, 2008).
Agrawal, R.K. et al., "Visualization of ribosome-recycling factor on the *Escherichia coli* 70S ribosome: Functional implications," Proc. Natl. Acad. Sci. U S A, vol. 101, No. 24, pp. 8900-8905 (Jun. 15, 2004).
Alkalaeva, E.Z. et al., "In vitro reconstitution of eukaryotic translation reveals cooperativity between release factors eRF1 and eRF3," Cell, vol. 125, No. 6, pp. 1125-1136 (Jun. 16, 2006).
Altschul, S.F. et al., "Basic local alignment search tool," J. Mol. Biol., vol. 215, pp. 403-410 (1990).

(Continued)

*Primary Examiner* — Alexander Kim
(74) *Attorney, Agent, or Firm* — Wilmer Cutler Pickering Hale and Dorr LLP

(57) ABSTRACT

Provided are probes comprising a class 1 release factor conjugated to a fluorescent label and methods of making the probes. Also provided are methods for detecting conformational changes in ribosomes and associated molecules, such as class 1 release factors. In addition, methods of identifying a compound for reducing nonsense-mediated decay of mRNA and/or for inhibiting termination of protein synthesis at a premature stop codon, are described. Methods of assaying RF3 activity are also included.

17 Claims, 40 Drawing Sheets
(39 of 40 Drawing Sheet(s) Filed in Color)

(56) References Cited

PUBLICATIONS

Anczukow, O. et al., "Does the nonsense-mediated mRNA decay mechanism prevent the synthesis of truncated BRCA1, CHK2, and p53 proteins?," Human Mutattion, vol. 29, No. 1, pp. 65-73 (2008).

Andrec, M. et al., "Direct Determination of Kinetic Rates from Single-Molecule Photon Arrival Trajectories Using Hidden Markov Models," J. Phys. Chem. A., vol. 107, No. 38, pp. 7454-7464 (Sep. 25, 2003).

Barat, C. et al., "Progression of the ribosome recycling factor through the ribosome dissociates the two ribosomal subunits," Mol. Cell, vol. 27, No. 2, pp. 250-261 (Jul. 20, 2007).

Bartley, L.E. et al., "Exploration of the transition state for tertiary structure formation between an RNA helix and a large structured RNA," J. Mol. Biol., vol. 328, pp. 1011-1026 (2003).

Barton-Davis, E.R. et al., "Aminoglycoside antibiotics restore dystrophin function to skeletal muscles of mdx mice," J. Clin. Invest., vol. 104, No. 4, pp. 375-381, 9 pages (Aug. 1999).

Bastiaens, P.I. et al., "Microspectroscopic imaging tracks the intracellular processing of a signal transduction protein: fluorescent-labeled protein kinase C beta I," Proc. Natl. Acad. Sci. U S A, vol. 93, pp. 8407-8412 (Aug. 1996).

Bertram, G. et al., "Endless possibilities: translation termination and stop codon recognition," Microbiology, vol. 147, Pt. 2, pp. 255-269 (2001).

Björnsson, A. et al., "Structure of the C-terminal end of the nascent peptide influences translation termination," Embo. J., vol. 15, No. 7, pp. 1696-1704 (1996).

Blanchard, S.C. et al., "tRNA selection and kinetic proofreading in translation," Nat. Struct. Mol. Biol., vol. 11, No. 10, pp. 1008-1014 (Oct. 2004).

Blanchard, S.C. et al., "tRNA dynamics on the ribosome during translation," Proc. Natl. Acad. Sci. U S A, vol. 101, No. 35, pp. 12893-12898 (Aug. 31, 2004).

Bonetti, B. et al., "The efficiency of translation termination is determined by a synergistic interplay between upstream and downstream sequences in *Saccharomyces cerevisiae*," J. Mol. Biol., vol. 251, pp. 334-345 (1995).

Borovinskaya, M.A. et al., "Structural basis for aminoglycoside inhibition of bacterial ribosome recycling," Nature Structural & Molecular Biology, vol. 17, No. 8, pp. 727-732, 7 pages (Aug. 2007).

Brito, M. et al., "Polyglycine expansions in eRF3/GSPT1 are associated with gastric cancer susceptibility," Carcinogenesis, vol. 26, No. 12, pp. 2046-2049 (2005).

Brown, C.M. et al., "Two regions of the *Escherichia coli* 16S ribosomal RNA are important for decoding stop signals in polypeptide chain termination," Nucleic Acids Research, vol. 21, No. 9, pp. 2109-2115, 8 pages (1993).

Buckingham, R.H. et al., "Polypeptide chain release factors," Molecular Microbiology, vol. 24, No. 3, pp. 449-456 (1997).

Chabelskaya, S. et al., "Inactivation of NMD increases viability of sup45 nonsense mutants in *Saccharomyces cerevisiae*," BMC Molecular Biology, vol. 8, No. 71, 12 pages (2007).

Chang, Y.F. et al., "The nonsense-mediated decay RNA surveillance pathway," Annu. Rev. Biochem., vol. 76, pp. 51-74, 25 pages (2007).

Chavatte, L. et al., "The polypeptide chain release factor eRF1 specifically contacts the s(4)UGA stop codon located in the A site of eukaryotic ribosomes," Eur. J. Biochem., vol. 268, pp. 2896-2904 (Feb. 2001).

Cheng, Z. et al., "Structural insights into eRF3 and stop codon recognition by eRF1," Genes & Development, vol. 23, pp. 1106-1118, 14 pages (2009).

Clancy, J.P. et al., "Evidence that systemic gentamicin suppresses premature stop mutations in patients with cystic fibrosis," AM. J. Resplr. Crit. Care Med., vol. 163, pp. 1683-1692 (2001).

Collins, R.T. et al., "A genetic screen in *Drosophila* for identifying novel components of the hedgehog signaling pathway," Genetics, vol. 170, No. 1, pp. 173-184, 14 pages (May 2005).

Connell, S.R. et al., "Structural basis for interaction of the ribosome with the switch regions of GTP-bound elongation factors," Molecular Cell, vol. 25, pp. 751-764 (Mar. 9, 2007).

Cornish, P.V. et al., "Following movement of the L1 stalk between three functional states in single ribosomes," Proc. Natl. Acad. Sci. U S A, vol. 106, No. 8, pp. 2571-2576 (Feb. 24, 2009).

Cornish, P.V. et al., "Spontaneous intersubunit rotation in single ribosomes," Molecular Cell, vol. 30, pp. 578-588 (Jun. 6, 2008).

Dincbas-Renqvist V. et al., "A post-translational modification in the GGQ motif of RF2 from *Escherichia coli* stimulates termination of translation," The EMBO Journal, vol. 19, No. 24, pp. 6900-6907 (2000).

Dorywalska, M. et al., "Site-specific labeling of the ribosome for single-molecule spectroscopy," Nucleic Acids Research, vol. 33, No. 1, pp. 182-189 (2005).

Du, M. et al., "PTC124 is an orally bioavailable compound that promotes suppression of the human CFTR G542X nonsense allele in a CF mouse model," PNAS, vol. 105, No. 6, pp. 2064-2069 (Feb. 12, 2008).

Dubourg, C. et al., "Evaluation of ETF1/eRF1, mapping to 5q31, as a candidate myeloid tumor suppressor gene," Cancer Genetics and Cytogenetics, vol. 134, pp. 33-37 (2002).

English, B.P. et al., "Ever-fluctuating single enzyme molecules: Michaelis-Menten equation revisited," Nature Chemical Biology, vol. 2, No. 2, pp. 87-94 (Feb. 2006).

Ermolenko, D.N. et al., "Observation of intersubunit movement of the ribosome in solution using FRET," J. Mol. Biol., vol. 370, pp. 530-540, 11 pages (2007).

Fei, J. et al., "Coupling of ribosomal L1 stalk and tRNA dynamics during translation elongation," Mol. Cell, vol. 30, pp. 348-359 (May 9, 2008).

Fourmy, D. et al., "Structure of the A site of *E. coli* 16S ribosomal RNA complexed with an aminoglycoside antibiotic," Science, vol. 274, pp. 1367-1371, 7 pages (Nov. 22, 1996).

Frank, J. et al., "A ratchet-like inter-subunit reorganization of the ribosome during translocation," Nature, vol. 406, No. 6793, pp. 318-322, 7 pages (Jul. 20, 2000).

Freistroffer, D.V. et al., "The accuracy of codon recognition by polypeptide release factors," PNAS, vol. 97, No. 5, pp. 2046-2051 (Feb. 29, 2000).

Freistroffer, D.V. et al., "Release factor RF3 in *E. coli* accelerates the dissociation of release factors RF1 and RF2 from the ribosome in a GTP-dependent manner," The EMBO Journal, vol. 16, No. 13, pp. 4126-4133 (1997).

Frischmeyer, P.A. et al., "Nonsense-mediated mRNA decay in health and disease," Human Molecular Genetics, vol. 8, No. 10, pp. 1893-1900 (1999).

Frolova, L.Y. et al., "Mutations in the highly conserved GGQ motif of class 1 polypeptide release factors abolish ability of human eRF1 to trigger peptidyl-tRNA hydrolysis," RNA, vol. 5, pp. 1014-1020, 8 pages (1999).

Fujiwara, T. et al., "Ribosome recycling factor disassembles the post-termination ribosomal complex independent of the ribosomal translocase activity of elongation factor G," Molecular Microbiology, vol. 53, No. 2, pp. 517-528 (2004).

Gao, H. et al., "RF3 induces ribosomal conformational changes responsible for dissociation of class I release factors," Cell, vol. 129, pp. 929-941 (Jun. 1, 2007).

Gao, N. et al., "Specific interaction between EF-G and RRF and its implication for GTP-dependent ribosome splitting into subunits," J. Mol. Biol., vol. 374, pp. 1345-1358 (2007).

Gao, N. et al., "Mechanism for the disassembly of the posttermination complex inferred from cryo-EM studies," Molecular Cell, vol. 18, pp. 663-674 (Jun. 10, 2005).

Goncalves, J. et al., "Modulation of translation factor's gene expression by histone deacetylase inhibitors in breast cancer cells," Clin. Chem. Lab. Med., vol. 43, No. 2, pp. 151-156, 7 pages (2005).

Gonzalez Jr. et al., "Thiostrepton inhibition of tRNA delivery to the ribosome," RNA, vol. 13, pp. 2091-2097, 8 pages (2007).

Graille, M. et al., "Molecular basis for bacterial class I release factor methylation by PrmC," Molecular Cell, vol. 20, pp. 917-927 (Dec. 22, 2005).

(56) References Cited

OTHER PUBLICATIONS

Green, R.E. et al., "Widespread predicted nonsense-mediated mRNA decay of alternatively spliced transcripts of human normal and disease genes," Bioinfomatics, vol. 19, Suppl. 1, pp. i118-i121 (2003).
Guenet, L. et al., "Eukaryotic translation termination factor gene (ETF1/eRF1) maps at D5S500 in a commonly deleted region of chromosome 5q31 in malignant myeloid diseases," Cytogenet. Cell, vol. 88, pp. 82-86, 6 pages (2000).
Guex, N. et al., "Swiss-Model and the Swiss-PdbViewer: an environment for comparative protein modeling," Electrophoresis, vol. 18, pp. 2714-2723, 11 pages (1997).
Guo, P. et al., "Domain II plays a crucial role in the function of ribosome recycling factor," Biochem. J., vol. 393, pp. 767-777 (2006).
Hermanson, Greg T., "Bioconjugate Techniques," Academic Press, San Diego, 15 pages (1996).
Heurgue-Hamard, V. et al., "The hemK gene in *Escherichia coli* encodes the N(5)-glutamine methyltransferase that modifies peptide release factors," The EMBO Journal, vol. 21, No. 4, pp. 769-778 (2002).
Hirokawa, G. et al., "The role of ribosome recycling factor in dissociation of 70S ribosomes into subunits," RNA, vol. 11, pp. 1317-1328, 13 pages (2005).
Hirokawa, G. et al., "In vivo effect of inactivation of ribosome recycling factor—fate of ribosomes after unscheduled translation downstream of open reading frame,". Mol. Microbiol., vol. 54, No. 4, pp. 1011-1021 (2004).
Hirokawa, G. et al., "Binding of ribosome recycling factor to ribosomes, comparison with tRNA," The Journal of Biological Chemistry, vol. 277, No. 39, pp. 35847-35852 (Sep. 27, 2002).
Hohng, S. et al., "Single-molecule three-color FRET," Biophys. J., vol. 87, pp. 1328-1337 (Aug. 2004).
Horton, H.R. et al., "Principles of Biochemistry,3rd Edition," Pearson Prentice Hall, 18 pages (2006).
Howard, M.T. et al., "Sequence specificity of aminoglycoside-induced stop condon readthrough: potential implications for treatment of Duchenne muscular dystrophy," Ann. Neurol., vol. 48, pp. 164-169 (2000).
Ionov, Y. et al., "Manipulation of nonsense mediated decay identifies gene mutations in colon cancer Cells with microsatellite instability," Oncogene, vol. 23, pp. 639-645 (2004).
Ito, K. et a., "A tripeptide 'anticodon' deciphers stop codons in messenger RNA," Nature, vol. 403, pp. 680-684, 7 pages (Feb. 10, 2000).
Ito, K. et al., "Single amino acid substitution in prokaryote polypeptide release factor 2 permits it to terminate translation at all three stop codons," Proc. Natl. Acad. Sci. USA, vol. 95, pp. 8165-8169 (Jul. 1998).
Ivanov, I. et al., "Identifying candidate colon cancer tumor suppressor genes using inhibition of nonsense-mediated mRNA decay in colon cancer cells," Oncogene, vol. 26, pp. 2873-2884 (2007).
Janosi, L. et al., "Evidence for in vivo ribosome recycling, the fourth step in protein biosynthesis," The EMBO Journal, vol. 17, No. 4, pp. 1141-1151 (1998).
Janzen, D.M. et al., "The effect of eukaryotic release factor depletion on translation termination in human cell lines," Nucleic Acids Research, vol. 32, No. 15, pp. 4491-4502 (2004).
Jorgensen, F. et al., "Release factor-dependent false stops are infrequent in *Escherichia coli*," J. Mol. Biol., vol. 230, pp. 41-50 (1993).
Julian, P. et al., "Structure of ratcheted ribosomes with tRNAs in hybrid states," Proc. Natl. Acad. Sci. USA, vol. 105, No. 44, pp. 16924-16927 (Nov. 4, 2008).
Karimi, R. et al., "Novel roles for classical factors at the interface between translation termination and initiation," Molecular Cell, vol. 3, pp. 601-609 (May 1999).
Keeling, K.M. et al., "Clinically relevant aminoglycosides can suppress diseaseassociated premature stop mutations in the IDUA and P53 cDNAs in a mammalian translation system," J. Mol. Med., vol. 80, pp. 367-376 (2002).
Kiel, M.C. et al., "Release of ribosome-bound ribosome recycling factor by elongation factor G," The Journal of Biological Chemistry, vol. 278, No. 48, pp. 48041-48050 (Nov. 28, 2003).
Kim, H.D. et al., "Fluctuations of transfer RNAs between classical and hybrid states," Biophysical Journal, vol. 93, pp. 3575-3582 (Nov. 2007).
Klaholz, B.P. et al., "Visualization of release factor 3 on the ribosome during termination of protein synthesis," Nature, vol. 427, Issue 6977, pp. 862-865, 6 pages (Feb. 26, 2004).
Klaholz, B.P. et al., "Structure of the *Escherichia coli* ribosomal termination complex with release factor 2," Nature, vol. 421, Issue 6918, pp. 90-94, 7 pages (Jan. 2, 2003).
Lancaster, L. et al., "Orientation of ribosome recycling factor in the ribosome from directed hydroxyl radical probing," Cell, vol. 111, pp. 129-140 (Oct. 4, 2002).
Laurberg, M. et al., "Structural basis for translation termination on the 70S ribosome," Nature vol. 454, Issue 7206, pp. 852-857, 8 pages (Aug. 14, 2008).
Linde, L. et al., "Nonsense mediated mRNA decay affects nonsense transcript levels and governs response of cystic fibrosis patients to gentamicin," J. Clin. Invest., vol. 117, No. 3, pp. 683-692, 12 pages (Mar. 2007).
Malta-Vacas, J. et al., "Differential expression of the eukaryotic release factor 3 (eRF3/GSPT1) according to gastric cancer histological types," J. Clin. Pathol., vol. 58, pp. 621-625 (2005).
Martin, R. et al., "Aminoglycoside suppression at UAG, UAA and UGA codons in *Escherichia coli* and human tissue culture cells," Mol. Gen. Genet., vol. 271, pp. 411-418, 10 pages (1989).
McKinney, S.A. et al., "Analysis of single-molecule FRET trajectories using hidden Markov modeling," Biophys. J., vol. 91, No. 5, pp. 1941-1951 (Sep. 2006).
Mitkevich, V.A. et al., "Termination of translation in eukaryotes is mediated by the quaternary eRF1*eRF3*GTP*Mg2+ complex. The biological roles of eRF3 and prokaryotic RF3 are profoundly distinct," Nucleic Acids Research, vol. 34, No. 14, pp. 3947-3954 (2006).
Mora, L. et al., "Stop codon recognition and interactions with peptide release factor RF3 of truncated and chimeric RF1 and RF2 from *Escherichia coli*," Molecular Microbiology, vol. 50, No. 5, pp. 1467-1476 (2003).
Munro, J.B. et al., "Identification of two distinct hybrid state intermediates on the ribosome," Molecular Cell, vol. 25, pp. 505-517 (Feb. 23, 2007).
Nakamura, Y. et al., "A tripeptide discriminator for stop codon recognition," FEBS Letters, vol. 514, pp. 30-33 (2002).
Nakano, H. et al., "Structure and binding mode of a ribosome recycling factor (RRF) from mesophilic bacterium," The Journal of Biological Chemistry, vol. 278, No. 5, pp. 3427-3436 (Jan. 31, 2003).
Ogle, J.M. et al., "Recognition of cognate transfer RNA by the 30S ribosomal subunit," Science, vol. 292, pp. 897-902, 8 pages (May 4, 2001).
Pape, T. et al., "Complete kinetic mechanism of elongation factor Tu-dependent binding of aminoacyl-tRNA to the A site of the *E. coli* ribosome," The EMBO Journal, vol. 17, No. 24, pp. 7490-7497 (1998).
Pavlov, M.Y. et al., "Complementary roles of initiation factor 1 and ribosome recycling factor in 70S ribosome splitting," The EMBO Journal, vol. 27, pp. 1706-1717 (2008).
Peske, F. et al., "Sequence of steps in ribosome recycling as defined by kinetic analysis," Molecular Cell, vol. 18, pp. 403-412 (May 13, 2006).
Petry, S. et al., "Crystal structures of the ribosome in complex with release factors RF1 and RF2 bound to a cognate stop codon," Cell, vol. 123, pp. 1255-1266 (Dec. 29, 2005).
Pisarev, A.V. et al., "Recycling of eukaryotic posttermination ribosomal complexes," Cell, vol. 131, pp. 286-299 (Oct. 19, 2007).
Pisareva, V.P. et al., "Kinetic analysis of interaction of eukaryotic release factor 3 with guanine nucleotides," The Journal of Biological Chemistry, vol. 281, No. 52, pp. 40224-40235 (Dec. 29, 2006).
Politano, L. et al., "Gentamicin administration in Duchenne patients with premature stop codon," Acta Myologica, pp. 15-21, 8 pages (May 2003).

(56) References Cited

OTHER PUBLICATIONS

Poole, E.S. et al., "Translational termination in *Escherichia coli*: three bases following the stop codon crosslink to release factor 2 and affect the decoding efficiency of UGA-containing signals," Nucleic Acids Research, vol. 26, No. 4, pp. 954-960 (1998).
Poole, E.S. et al., "The identity of the base following the stop codon determines the efficiency of in vivo translational termination in *Escherichia coli*," The EMBO Journal, vol. 14, No. 1, pp. 151-158 (1995).
Qin, F. et al., "A direct optimization approach to hidden Markov modeling for single channel kinetics," Biophysical Journal, vol. 79, pp. 1915-1927 (Oct. 2000).
Qin, F. et al., "Hidden Markov modeling for single channel kinetics with filtering and correlated noise," Biophysical Journal, vol. 79, pp. 1928-1944 (Oct. 2000).
Rawat, U. et al., "Interactions of the release factor RF1 with the ribosome as revealed by cryo-EM," J. Mol. Biol., vol. 357, pp. 1144-1153 (2006).
Rawat, U.B. et al., "A cryo-electron microscopic study of ribosome-bound termination factor RF2," Nature, vol. 421, Issue 6918, pp. 87-90, 6 pages (Jan. 2, 2003).
Rodnina, M.V. et al., "Recognition and selection of tRNA in translation," FEBS Letters, vol. 579, pp. 938-942 (2005).
Rossi, M.R. et al., "Identification of inactivating mutations in the JAK1, SYNJ2, and CLPTM1 genes in prostate cancer cells using inhibition of nonsense-mediated decay and microarray analysis," Cancer Genetics and Cytogenetics, vol. 161, pp. 97-103 (2005).
Sarkar, S.K. et al., "Engineered holliday junctions as single-molecule reporters for protein-DNA interactions with application to a MerR-family regulator," Journal of the American Chemical Society, vol. 129, No. 41, pp. 12461-12467, 9 pages (Oct. 17, 2007).
Seo, H.S. et al., "Kinetics and thermodynamics of RRF, EF-G, and thiostrepton interaction on the *Escherichia coli* ribosome," Biochemistry, vol. 43, No. 40, pp. 12728-12740, 15 pages (Oct. 12, 2004).
Seshadri, A. et al., "Mechanism of recycling of post-termination ribosomal complexes in eubacteria: a new role of initiation factor 3," Journal of Biosciences, vol. 31, No. 2, pp. 281-289, 11 pages (Jun. 2006).
Shin, D.H. et al., "Structural analyses of peptide release factor 1 from Thermotoga maritima reveal domain flexibility required for its interaction with the ribosome," J. Mol. Biol., vol. 341, pp. 227-239 (2004).
Spahn, C.M. et al., "Domain movements of elongation factor eEF2 and the eukaryotic 80S ribosome facilitate tRNA translocation," The EMBO Journal, vol. 23, pp. 1008-1019 (2004).
Stansfield, I. et al., "Depletion in the levels of the release factor eRF1 causes a reduction in the efficiency of translation termination in yeast," Molecular Microbiology, vol. 20, No. 6, pp. 1135-1143 (1996).
Stansfield, I. et al., "The products of the SUP45 (eRF1) and SUP35 genes interact to mediate translation termination in *Saccharomyces cerevisiae*," The EMBO Journal, vol. 14, No. 17, pp. 4365-4373 (1995).
Tate, W.P. et al., "The translational stop signal: Codon with a context, or extended factor recognition element?," Biochimie, vol. 78, pp. 945-952 (1996).
Tate, W.P. et al., "Translational termination: "Stop" for protein synthesis or "pause" for regulation of gene expression," Biochemistry, vol. 31, No. 9, pp. 2443-2450 (Mar. 10, 1992).
Taylor, D.J. et al., "Structures of modified eEF2 80S ribosome complexes reveal the role of GTP hydrolysis in translocation," The EMBO Journal, vol. 26, pp. 2421-2431 (2007).
Traut, R.R. et al., "The puromycin reaction and its relation to protein synthesis," J. Mol. Biol., vol. 10, pp. 63-72 (1964).
Uno, M. et al., "Polypeptide release at sense and noncognate stop codons by localized charge-exchange alterations in translational release factors," PNAS, vol. 99, No. 4, pp. 1819-1824 (Feb. 19, 2002).

Valle, M. et al., "Locking and unlocking of ribosomal motions," Cell, vol. 114, pp. 123-134 (Jul. 11, 2003).
Vestergaard, B. et al., "The SAXS solution structure of RF1 differs from its crystal structure and is similar to its ribosome bound cryo-EM structure," Molecular Cell, vol. 20, pp. 929-938 (Dec. 22, 2005).
Wagner, K.R. et al., "Gentamicin treatment of Duchenne and Becker muscular dystrophy due to nonsense mutations," Ann. Neurol., vol. 49, pp. 706-711 (2001).
Ware, M.D. et al., "Does nonsense-mediated mRNA decay explain the ovarian cancer cluster region of the BRCA2 gene?," Oncogene, vol. 25, pp. 323-328 (2006).
Weixlbaumer, A. et al., "Crystal structure of the ribosome recycling factor bound to the ribosome," Nature Structural & Molecular Biology, vol. 14, No. 8, pp. 733-737 (Aug. 2007).
Welch, E.M. et al., "PTC124 targets genetic disorders caused by nonsense mutations," Nature, vol. 447, pp. 87-91, 7 pages (May 3, 2007).
Wilschanski, M. et al., "Gentamicin induced correction of CFTR function in patients with cystic fibrosis and CFTR stop mutations," The New England Journal of Medicine, vol. 349, No. 15, pp. 1433-1441, 11 pages (Oct. 9, 2003).
Wilson, D.N. et al., "Protein synthesis at atomic resolution: mechanistics of translation in the light of highly resolved structures for the ribosome," Current Protein and Peptide Science, vol. 3, pp. 1-53 (2002).
Wilson, K.S. et al., "Functional sites of interaction between release factor RF1 and the ribosome," Nature Structural Biology, vol. 7, No. 10, pp. 866-870, 7 pages (Oct. 2000).
Wolf, M. et al., "NMD microarray analysis for rapid genome-wide screen of mutated genes in cancer," Cellular Oncology, vol. 27, pp. 169-173 (2005).
Yang, H. et al., "Probing single-molecule conformation dynamics photon by photon," Biophysical Journal 46th Annual Meeting of the Biophysical Society, San Francisco, California, USA, 1 page (Feb. 23-27, 2002).
Youngman, E.M. et al., "Stop codon recognition by release factors induces structural rearrangement of the ribosomal decoding center that is productive for peptide release," Molecular Cell, vol. 28, pp. 533-543 (Nov. 30, 2007).
Youngman, E.M. et al., "Two distinct conformations of the conserved RNA-rich decoding center of the small ribosomal subunit are recognized by tRNAs and release factors," Cold Spring Harb Symp Quant Biol, vol. 71, pp. 545-549, 7 pages (2006).
Zavialov, A.V. et al., "Splitting of the posttermination ribosome into subunits by the concerted action of RRF and EF-G," Molecular Cell, vol. 18, pp. 675-686 (Jun. 10, 2005).
Zavialov, A.V. et al., "Peptidyl-tRNA regulates the GTPase activity of translation factors," Cell, vol. 114, pp. 113-122 (Jul. 11, 2003).
Zavialov, A.V. et al., "Release of peptide promoted by the GGQ motif of class 1 release factors regulates the GTPase activity of RF3," Molecular Cell, vol. 10, pp. 789-798 (Oct. 2002).
Zavialov, A.V. et al., "A posttermination ribosomal complex is the guanine nucleotide exchange factor for peptide release factor RF3," Cell, vol. 107, pp. 115-124 (Oct. 5, 2001).
Zoldak, G. et al., "Release factors 2 from *Escherichia coli* and Thermus thermophilus: structural, spectroscopic and microcalorimetric studies," Nucleic Acids Research, vol. 35, No. 4, pp. 1343-1353 (2007).
Clegg R.M., Fluorescence resonance energy transfer, *Current Opinion in Biotechnology*, 6:103-110 (1995).
Berlman, I.B., Energy transfer parameters of aromatic compounds, Academic Press, New York, NY (1973) 5 pages.
Molecular Probes' Handbook of Fluorescent Probes and Research Chemicals, 6th Edition, Eugene, OR (1996), p. ix-xii and 1-6.
Selvin, The renaissance of fluorescence resonance energy transfer, *Nat Struct Biol.*, 7(9):730-4 (2000).
Wu and Brand, Resonance energy transfer: methods and applications, *Analytical Biochemistry*, 218:1-13 (1994).

* cited by examiner

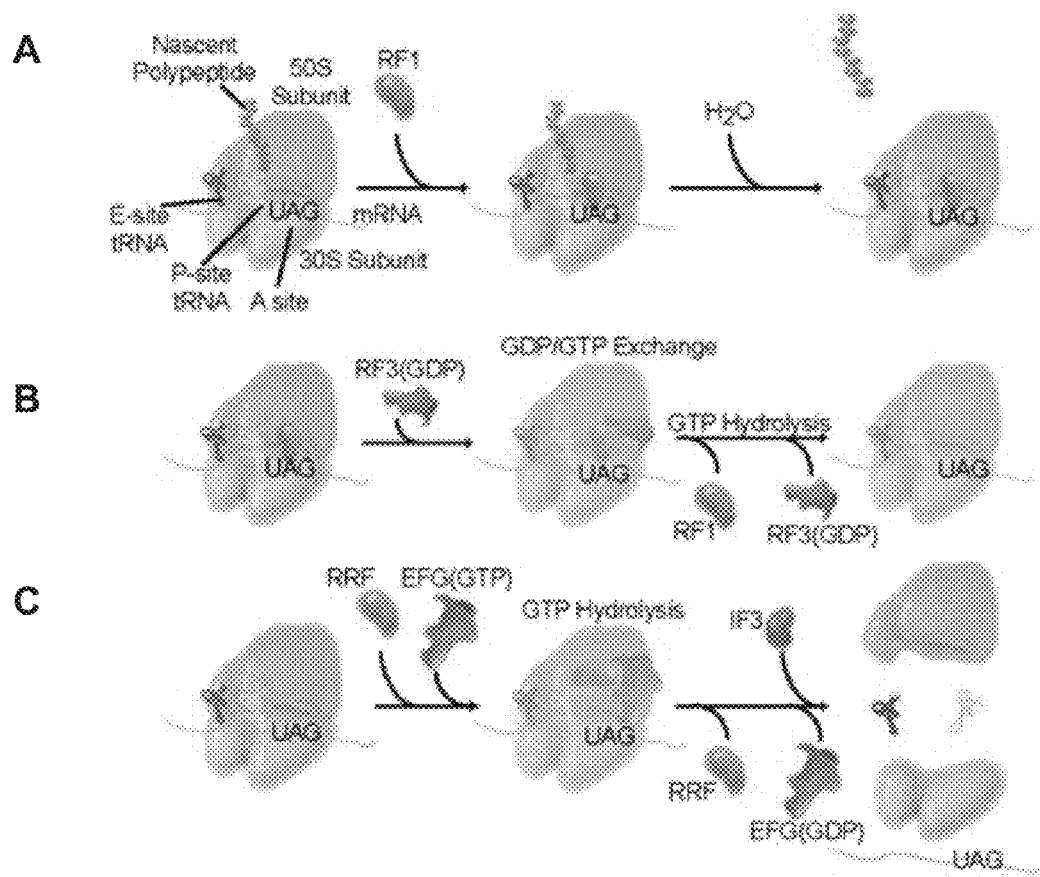
Figure 1A-C

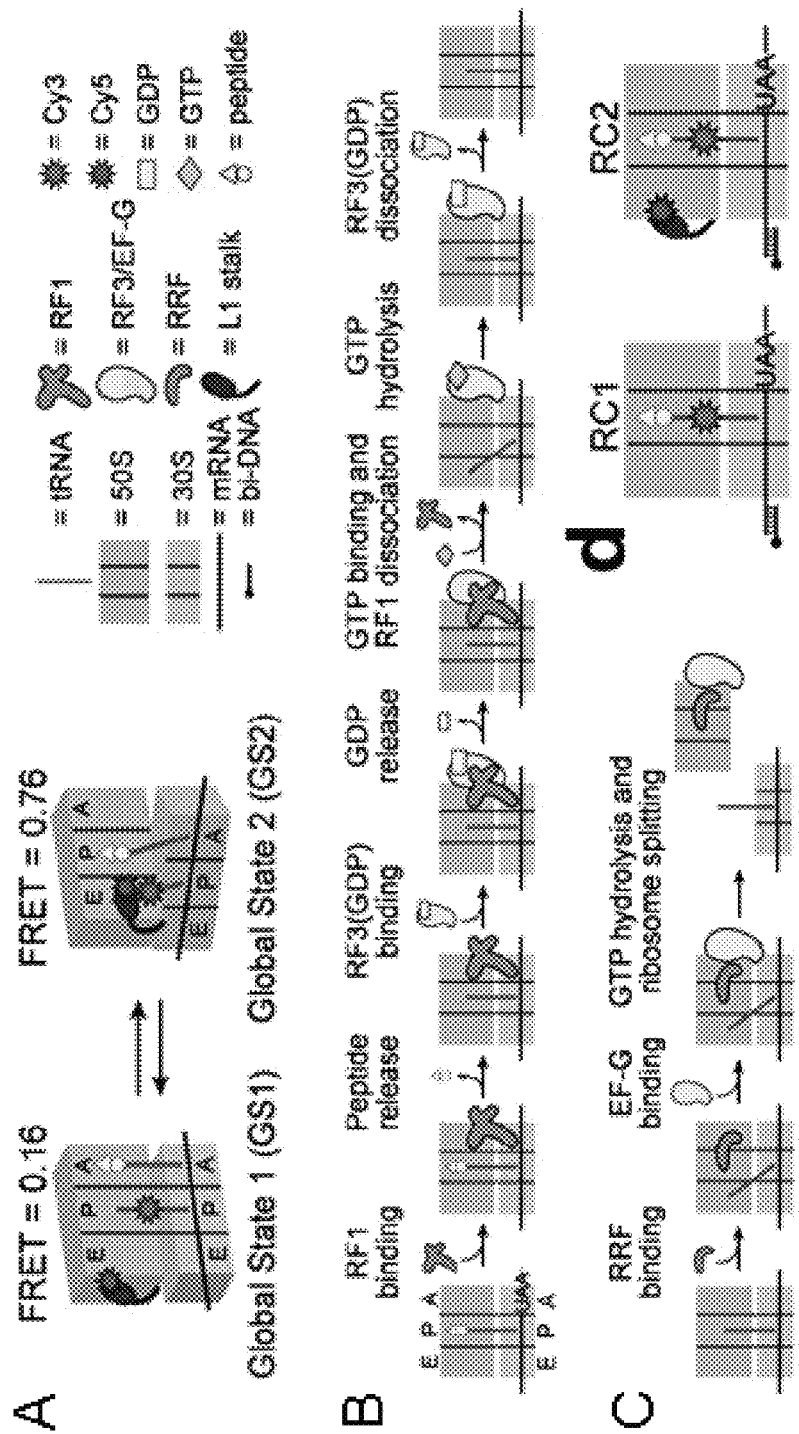
Figure 2A-D

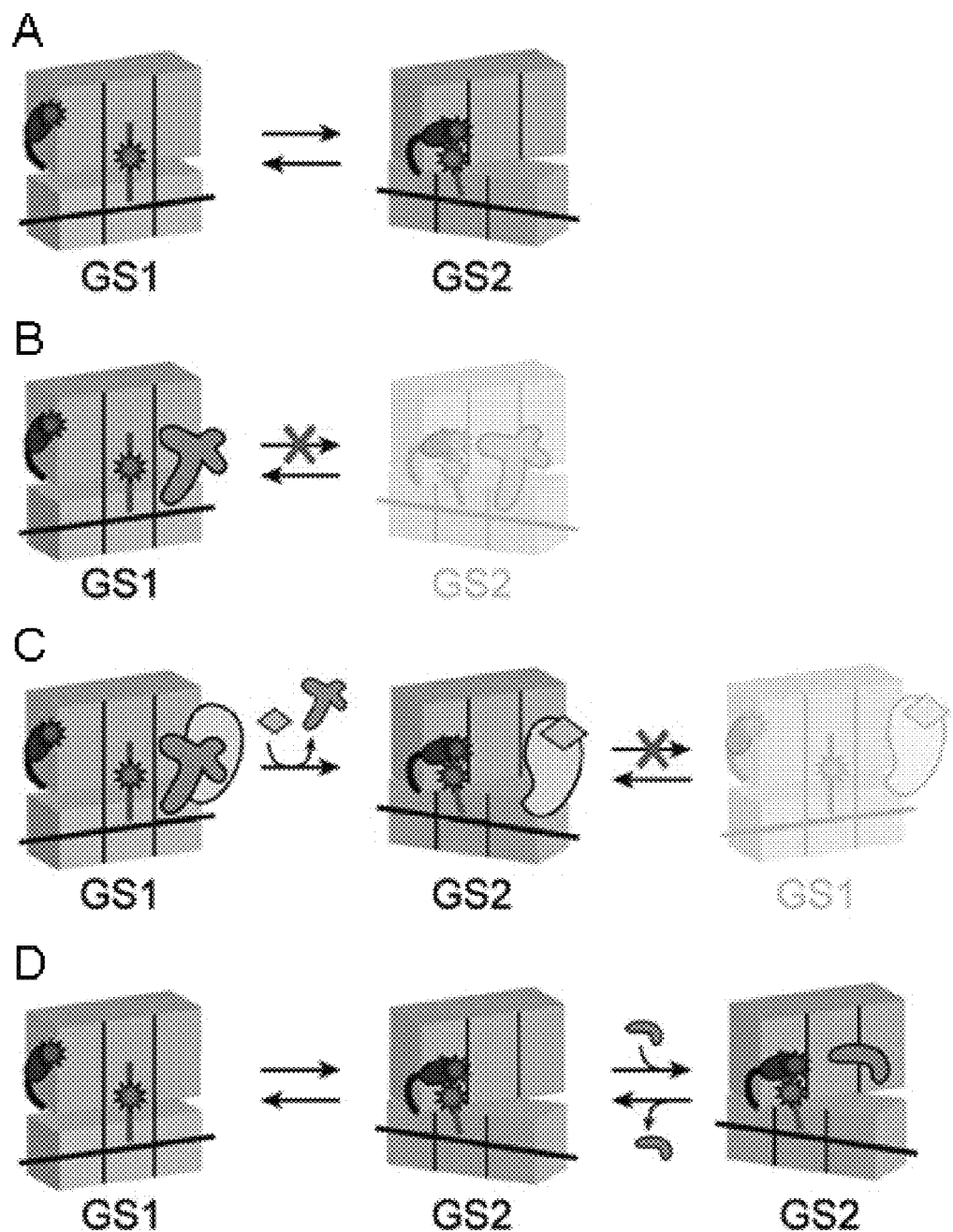
Figures 3A-D

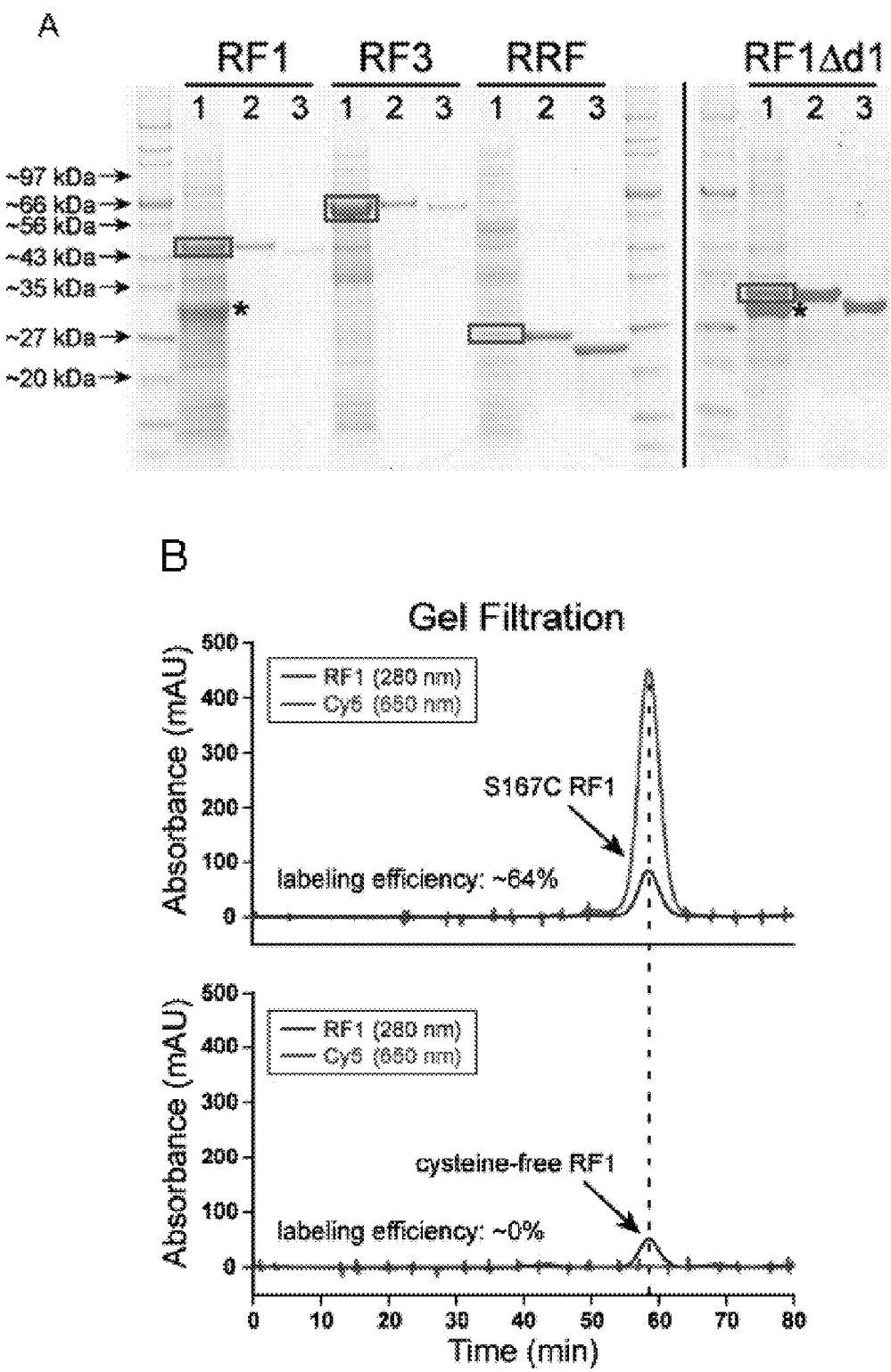
Figures 4A-B

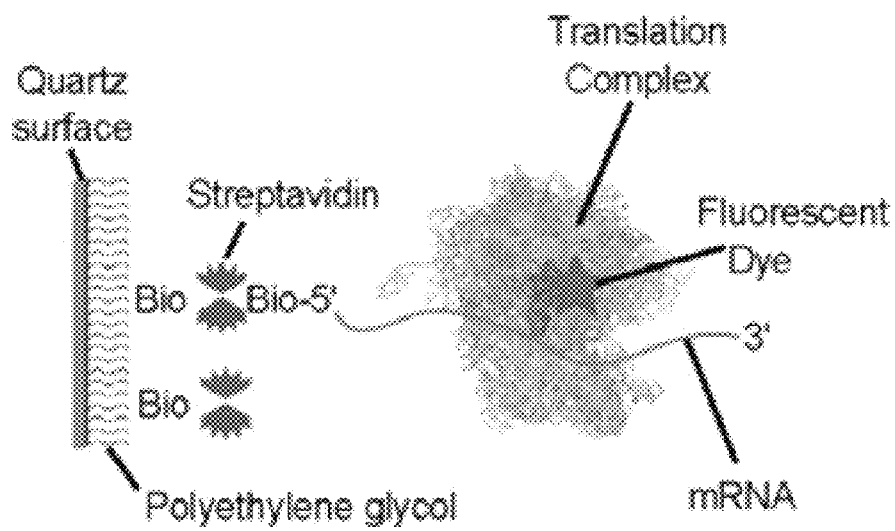
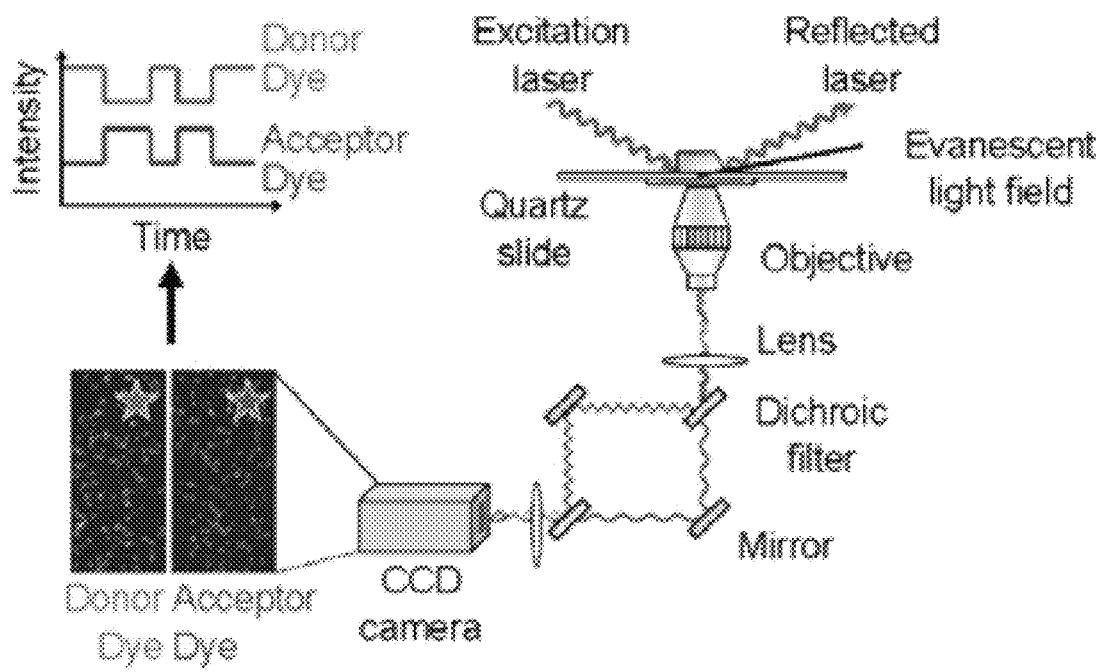
Figure 10A-B

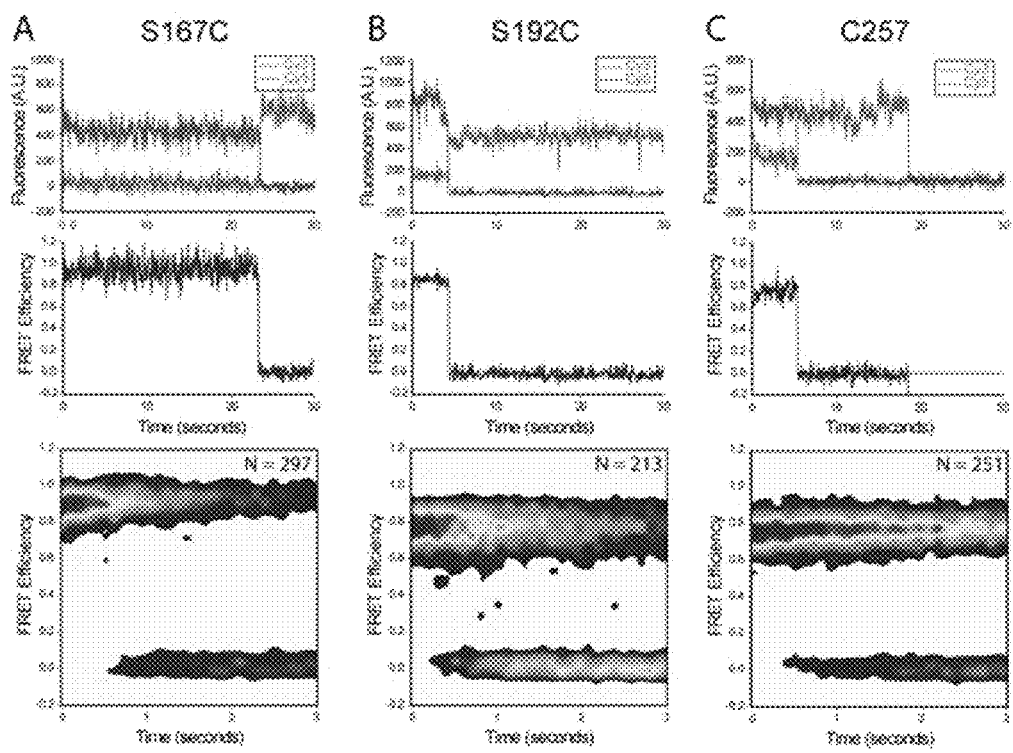
Figure 11A-C

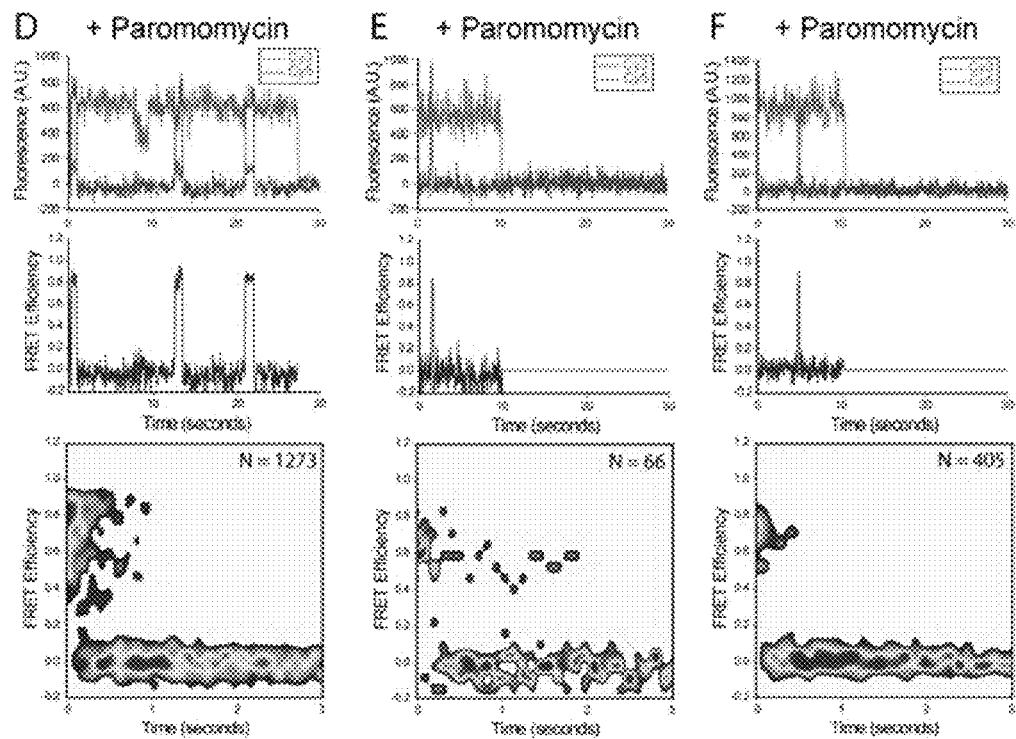
Figure 11D-F

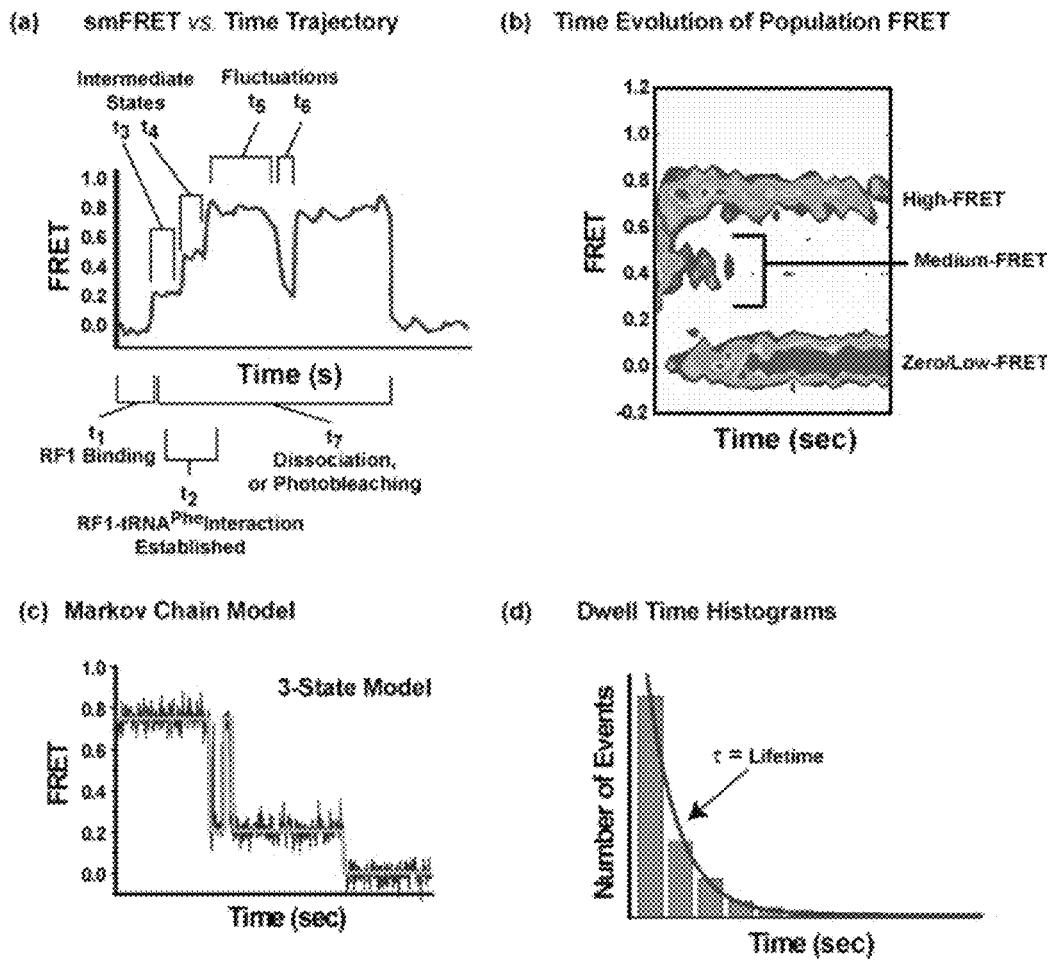
Figure 15A-D

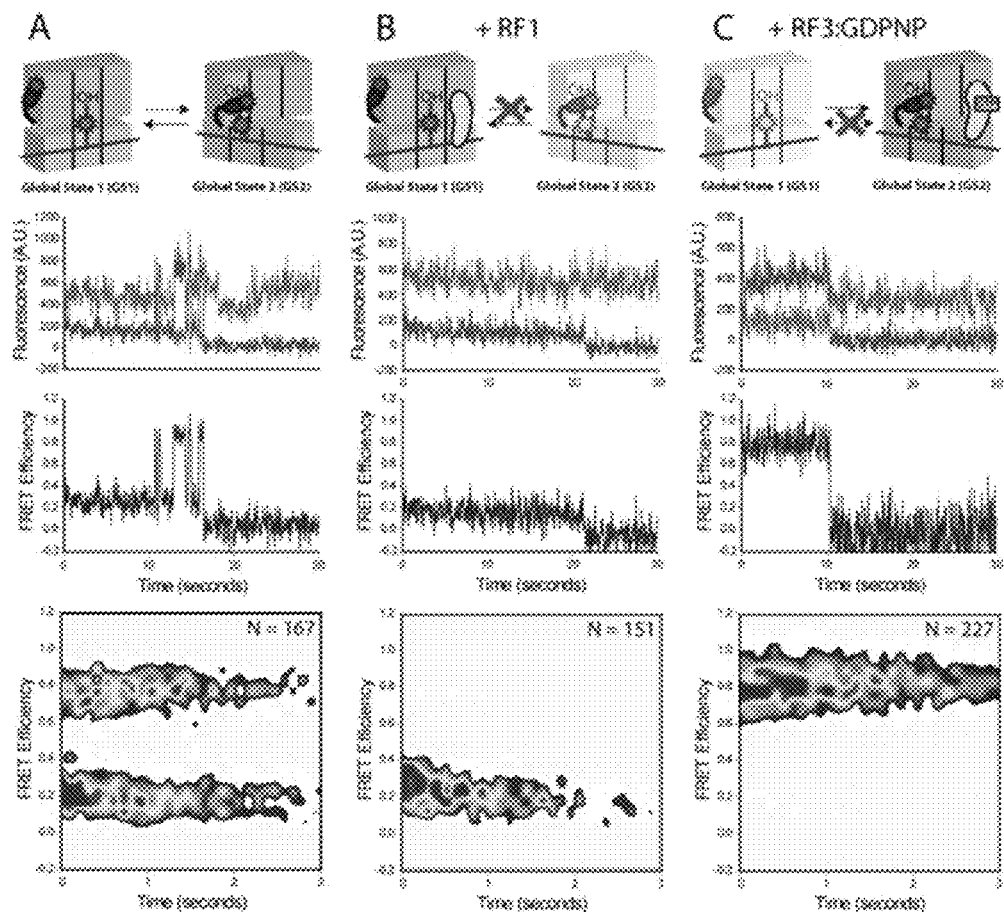
Figure 16A-C

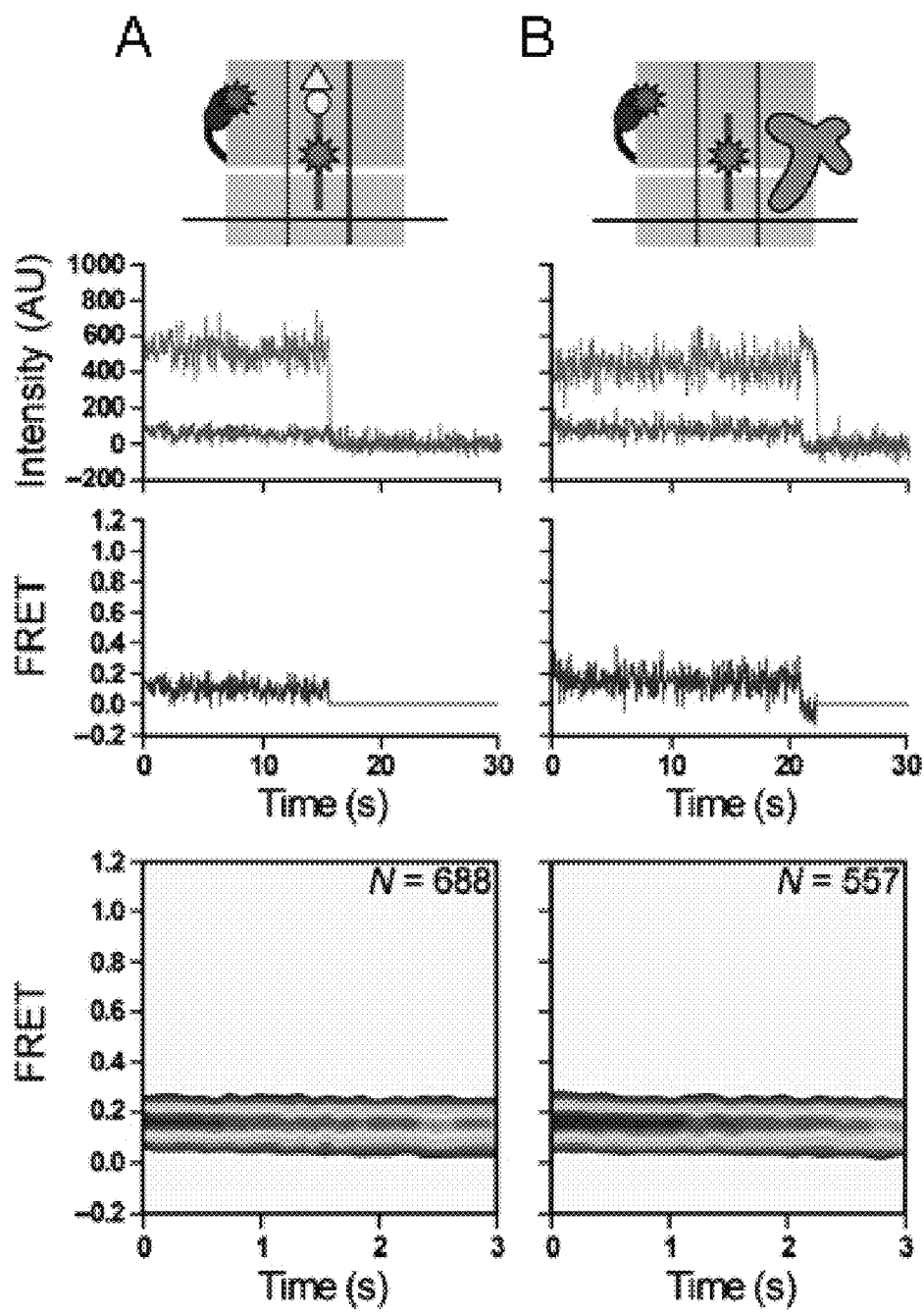
Figures 17A-B

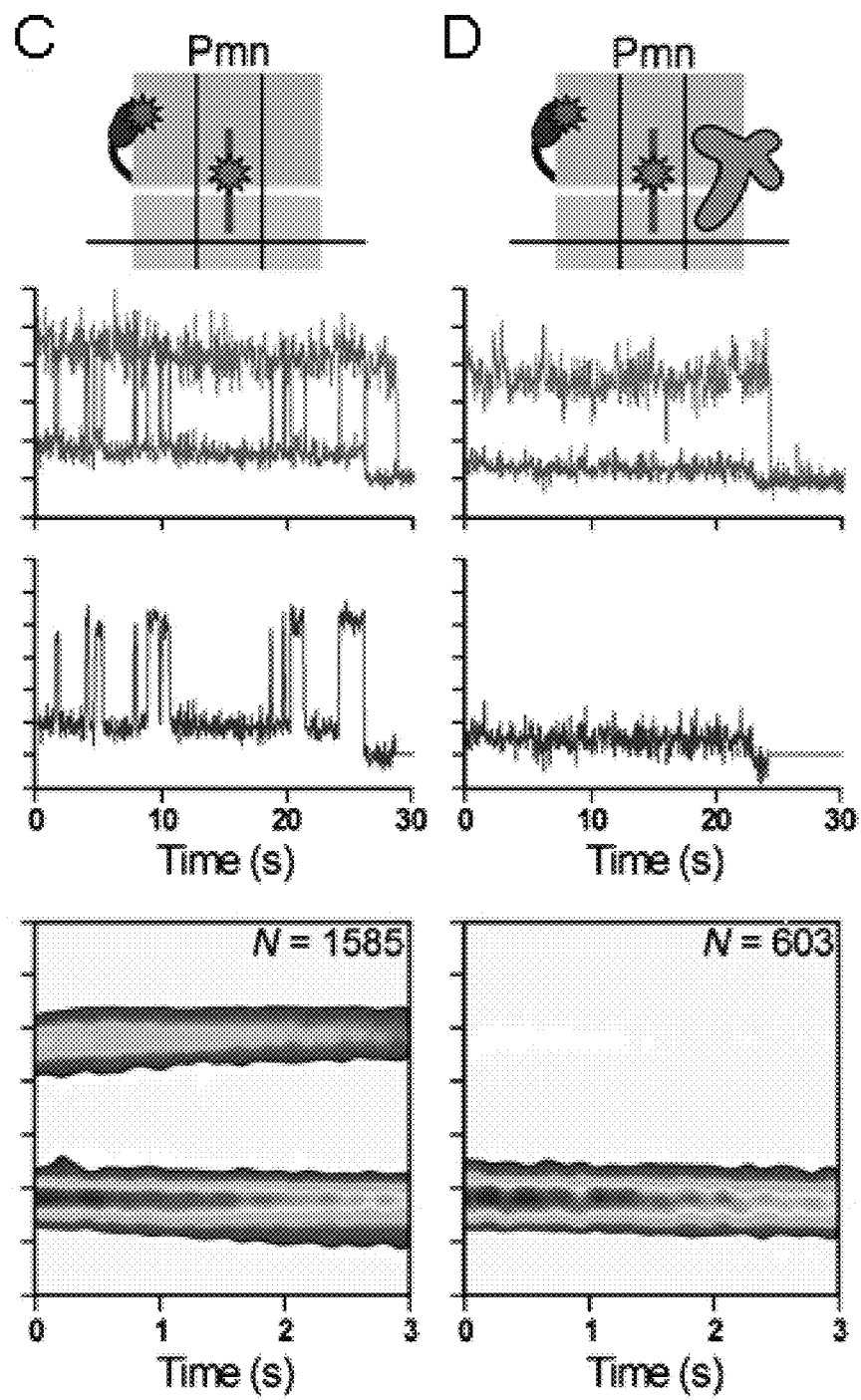
Figures 17C-D

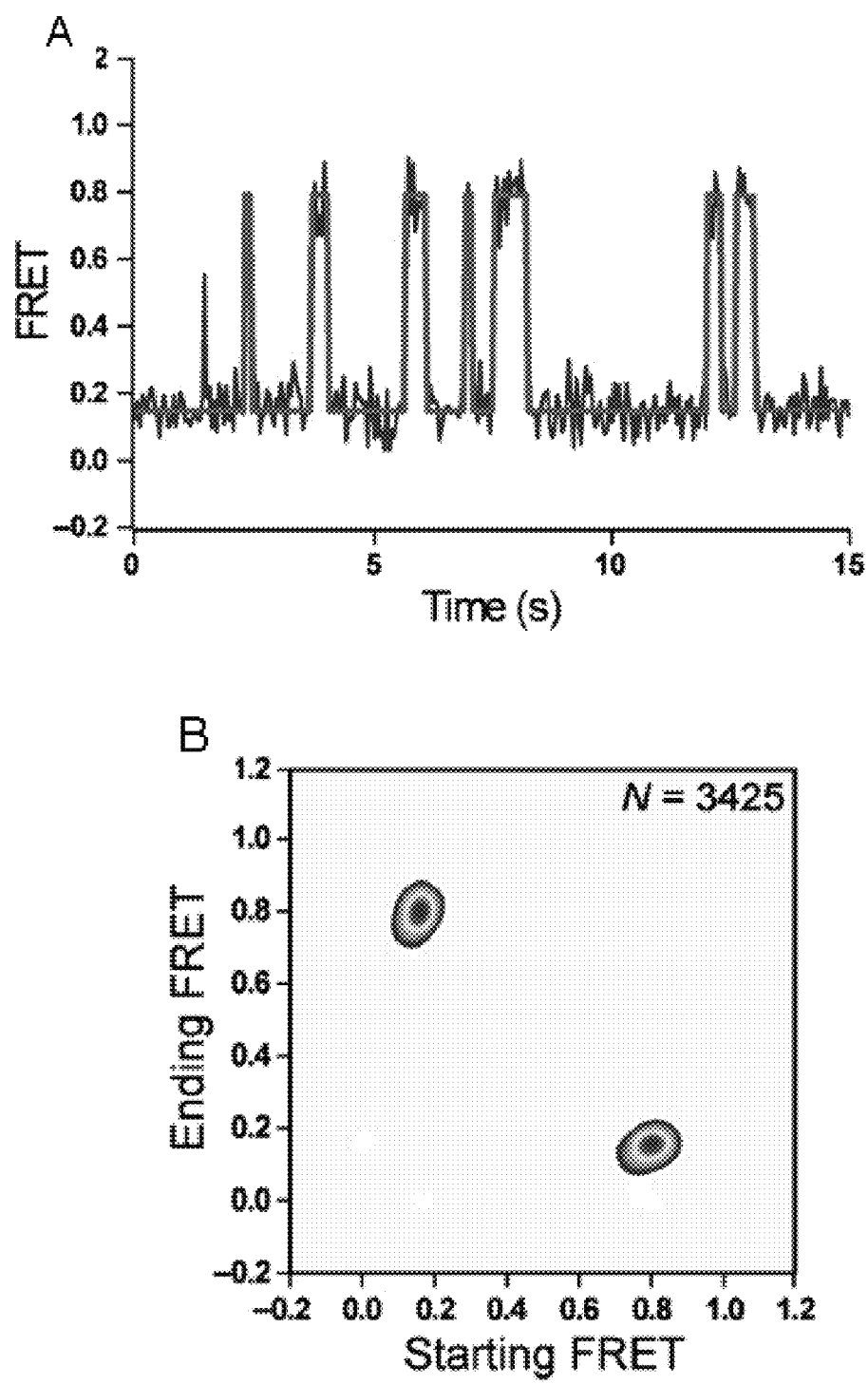
Figures 18A-B

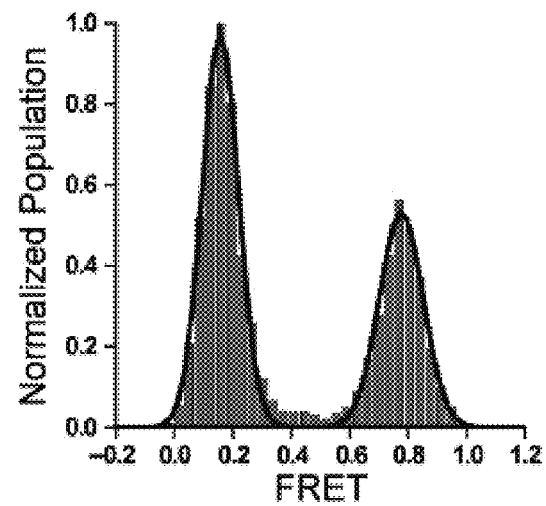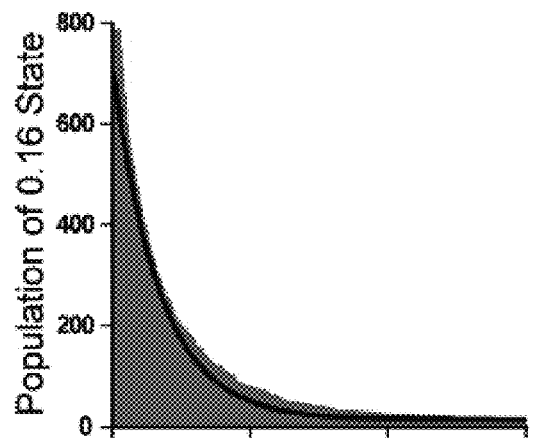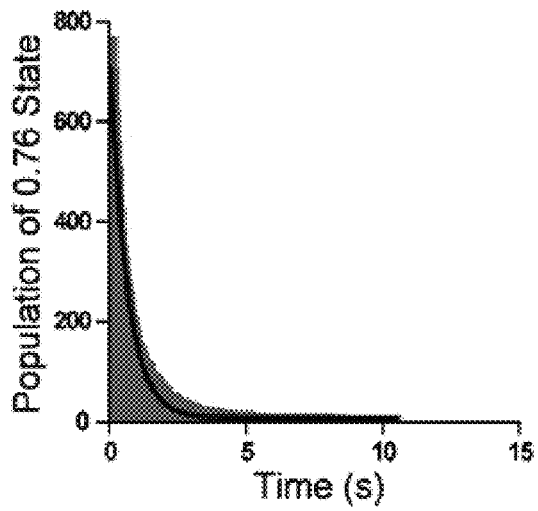
Figures 18C-E

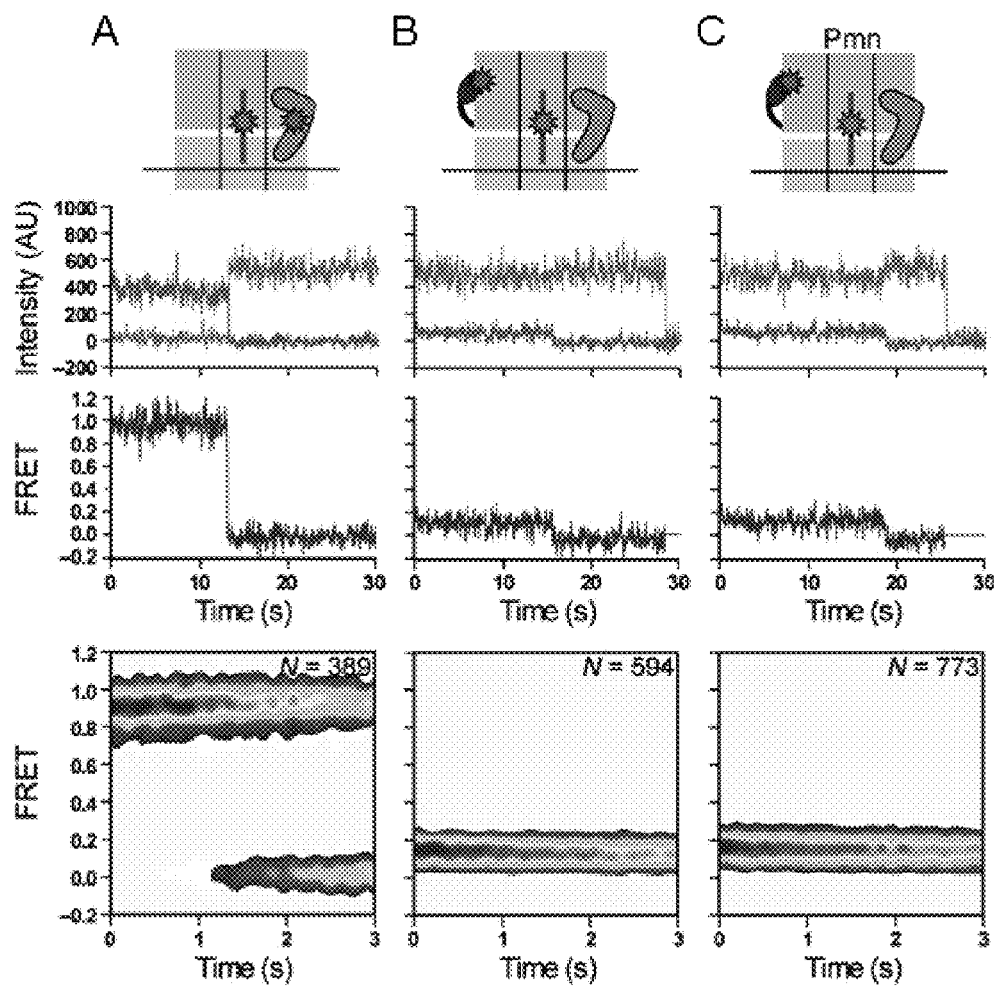
Figures 19A-C

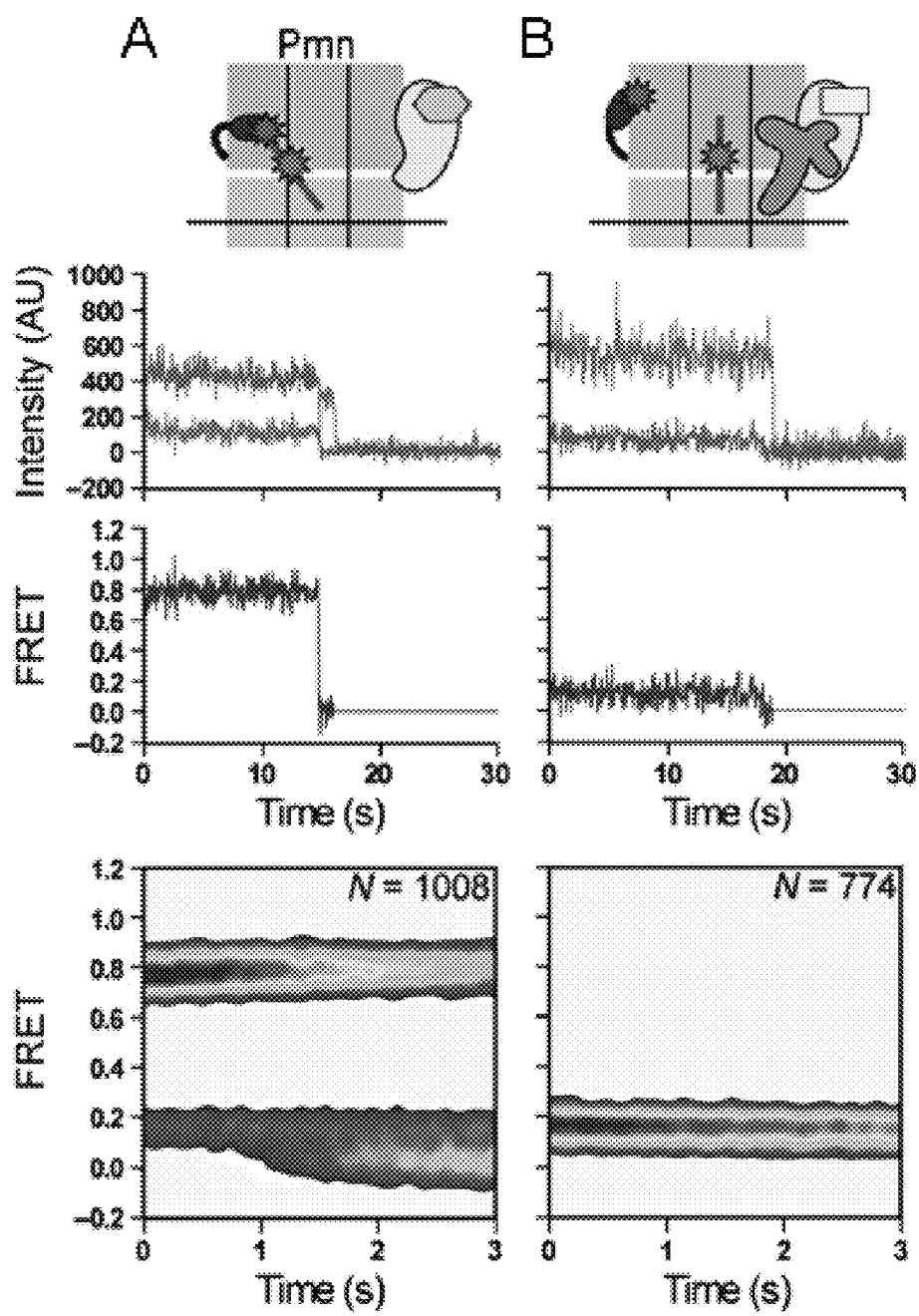
Figures 20A-B

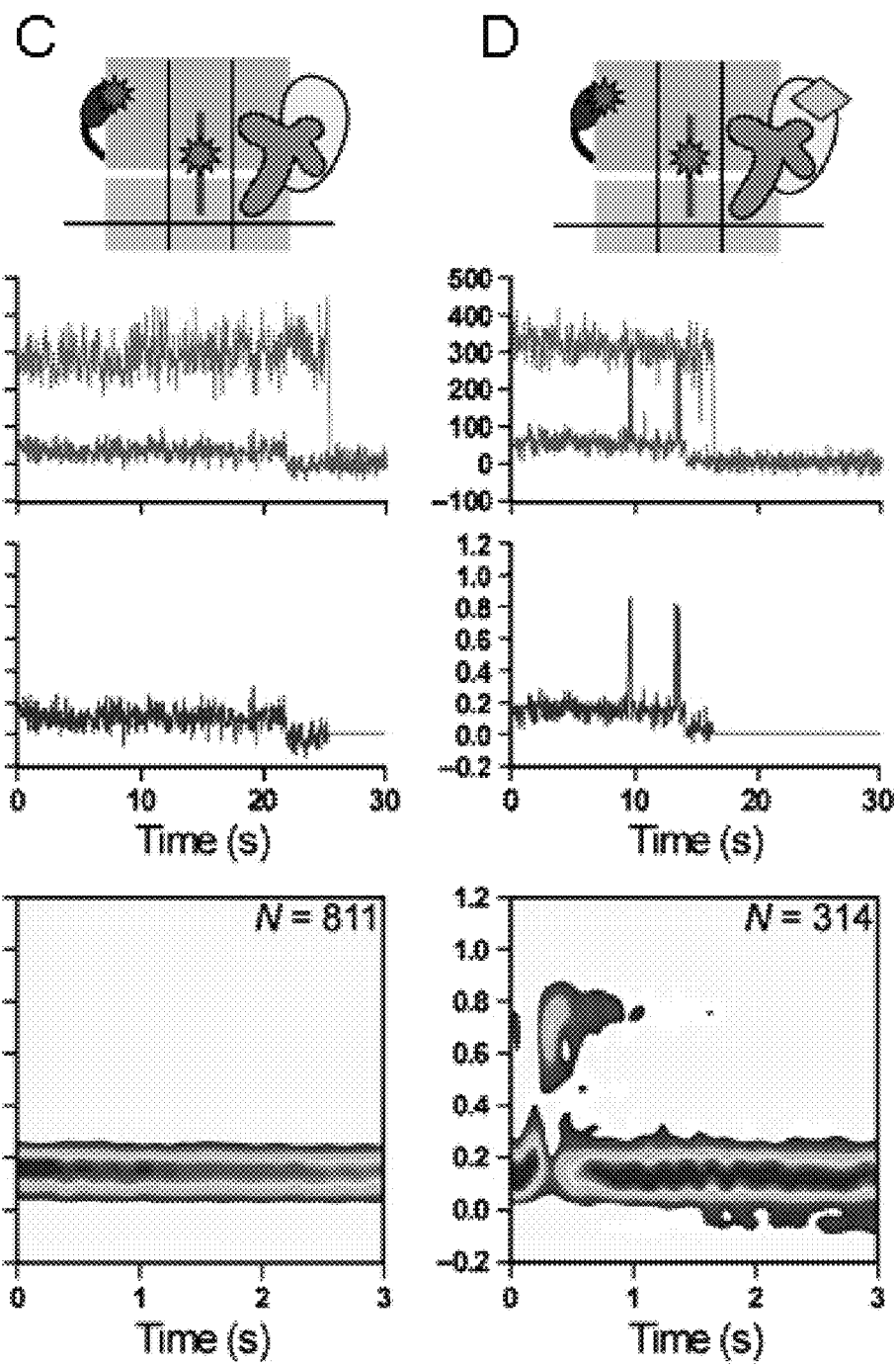
Figures 20C-D

Figures 23A-C

SDS-PAGE profile of various double Cys mutants of RF1

1. wild type RF1
2. 141/256 RF1
3. 167/192 RF1
4. 167/328 RF1
5. 192/256 RF1
6. 256/328 RF1
7. 256/315 RF1
8. 192/256/G299A/G310A RF1
9. 256/328G299A/G301A RF1

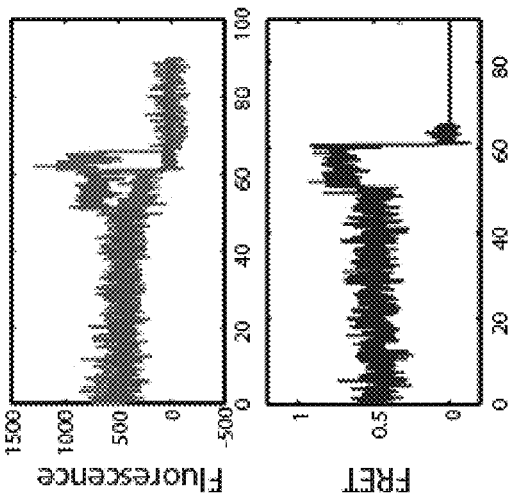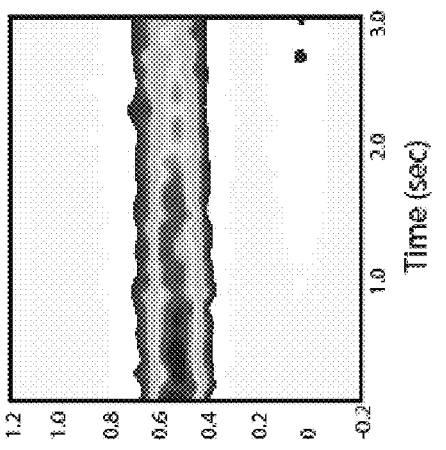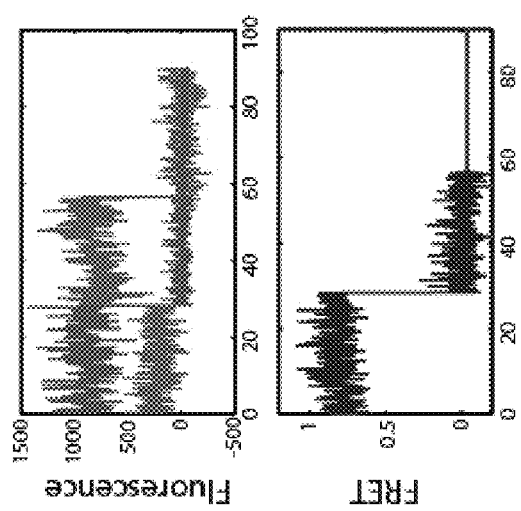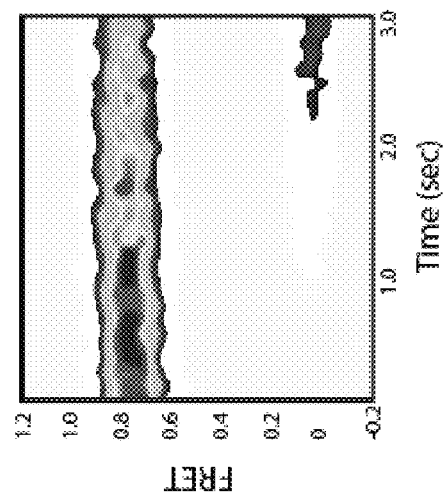
Figure 31

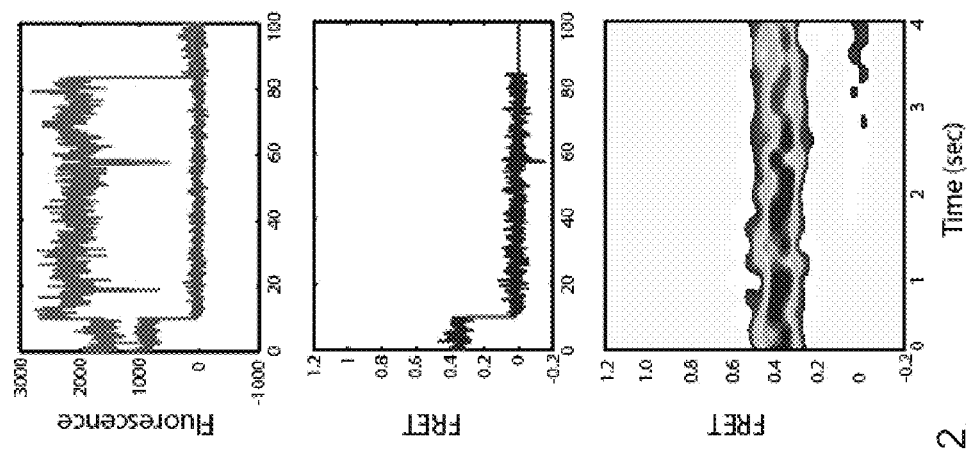
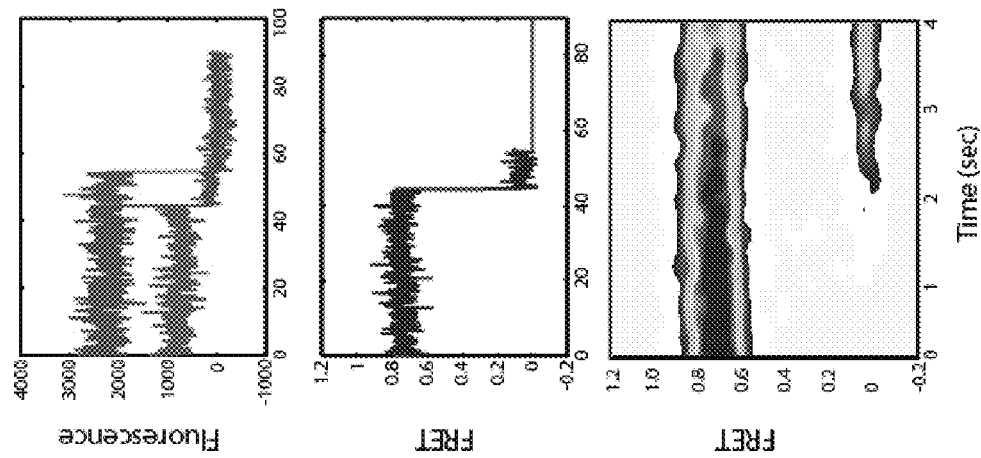
Figure 32

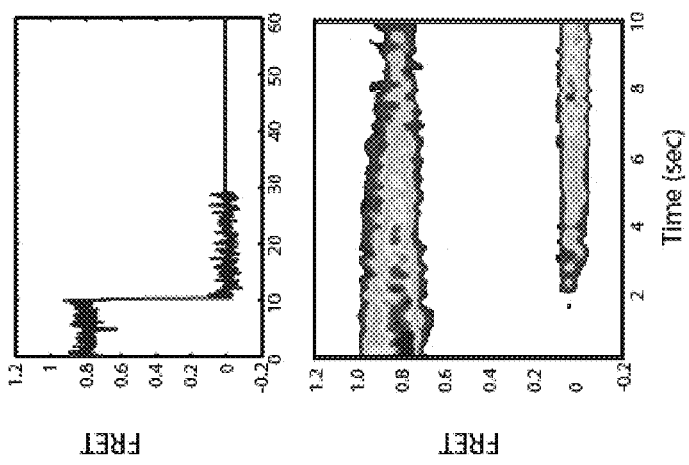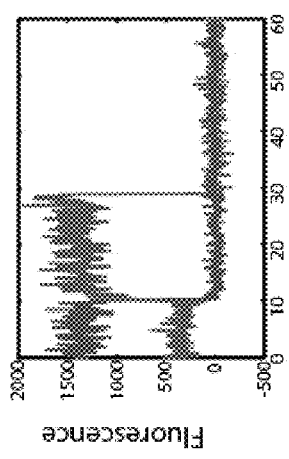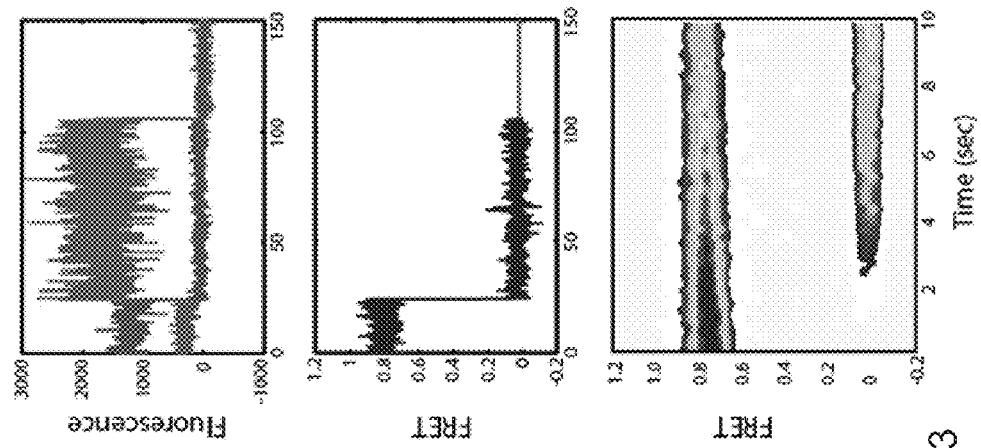
Figure 33

FLUORESCENCE-BASED APPROACH TO MONITOR RELEASE FACTOR-CATALYZED TERMINATION OF PROTEIN SYNTHESIS

This application claims the benefit of and priority to U.S. provisional patent application Ser. No. 61/447,646 filed Feb. 28, 2011, the disclosures of which is hereby incorporated by reference in its entirety for all purposes.

All publications, patent applications, patents, and other references mentioned herein are incorporated by reference in their entireties to the same extent as if each was specifically and individually indicated to be incorporated by reference. The patent and scientific literature referred to establishes knowledge available to those skilled in the art. In the case of inconsistencies, the present disclosure will prevail. The disclosures of U.S. Pat. No. 7,297,532 and U.S. Pub. No. 2004/0023256 are hereby incorporated by reference in their entireties.

SEQUENCE LISTING

The instant application contains a Sequence Listing which has been submitted in ASCII format via EFS-Web and is hereby incorporated by reference in its entirety. Said ASCII copy, created on Apr. 20, 2012, is named 19240837.txt and is 2,640 bytes in size.

BACKGROUND OF THE INVENTION

The mRNA quality-control mechanism known as nonsense mediated mRNA decay (NMD) degrades mRNAs having one or more premature stop codons within intragenic regions. Genetic mutations introducing such termination defects have been causally linked to a number of human genetic diseases, including Duchenne muscular dystrophy (caused by a premature stop codon mutation in the gene encoding dystrophin), nonsense mutation-mediated cystic fibrosis (caused by a premature stop codon mutation in the gene encoding the cystic fibrosis transmembrane conductance regulator), and numerous cancers. Of NMD-implicated cancers, the most prominent is a widespread form of breast cancer that is caused by a premature stop codon in the BRCA1 or BRCA2 tumor suppressor gene.

Previous small molecule based therapeutic efforts to inhibit termination events at premature stop codons have been limited by clinically significant side effects. Accordingly, there is a need to design and develop broadly applicable small-molecule therapeutic agents capable of specifically interfering with the recognition of premature stop codons, while leaving eRF1-catalyzed termination at naturally-occurring stop codons unperturbed. Such molecules can be used to abrogate the NMD pathway and rescue production of the protein encoded by the premature-stop codon-containing mRNA. The invention described herein addresses this need.

SUMMARY OF THE INVENTION

In one embodiment, the invention provides a probe comprising a class 1 release factor (RF) conjugated to a fluorescent label. The fluorescent label can comprise, for example, a fluorescein, a rhodamine, a cyanine, a coumarin, or a derivative thereof. The class 1 RF can be selected from the group consisting of RF1, RF2, and eRF1. In preferred embodiments, the class 1 RF is conjugated to one fluorescent label or two fluorescent labels. The two fluorescent labels can be a donor-acceptor pair. The donor-acceptor pair is preferably selected from the group consisting of coumarin 4/coumarin 343; 6-carboxyfluorescein/6-carboxy-X-rhodamine; 5,7-dimethyl-BODIPY/5-(4-phenyl-1,3-butadienyl) BODIPY; and Cy3/Cy5.

Also provided is a method of making a class 1 RF conjugated to one fluorescent label, the method comprising: identifying one or more phylogenetically-variable amino acids in a class 1 RF sequence; mapping the one or more phylogenetically-variable amino acids onto the three-dimensional structures of class 1 RFs; removing all wild type cysteine residues; replacing one phylogenetically-variable amino acid in an inactive region of the class 1 RF with a cysteine residue; and conjugating the fluorescent label to the cysteine residue; thereby making a class 1 RF conjugated to one fluorescent label.

The invention also provides a method of making a class 1 RF conjugated to two fluorescent labels, the method comprising: identifying at least two phylogenetically-variable amino acids in a class 1 RF sequence; mapping the phylogenetically-variable amino acids in the three-dimensional structure of the class 1 RF; removing all wildtype cysteine residues; replacing each of two phyologenetically-variable amino acids in an inactive region of the class 1 RF with a cysteine residue; and conjugating two fluorescent labels to the cysteine residues; thereby making a class 1 RF conjugated to two fluorescent labels. The two fluorescent labels can be a donor-acceptor pair. The method can further comprise the step of isolating class 1 RFs conjugated to a donor-acceptor pair, for example, by hydrophobic interaction chromatography.

Another aspect of the invention is a method of detecting a conformational change in a ribosome, the method comprising: providing a reaction mixture comprising an isolated, translationally-competent bacterial ribosome complex bound to a solid surface, wherein the ribosome complex comprises a first fluorescent label; adding to the reaction mixture a probe comprising a class 1 RF conjugated to a second fluorescent label, wherein the first fluorescent label and the second fluorescent label are a donor-acceptor pair; and measuring fluorescence resonance energy transfer (FRET) efficiency between the donor-acceptor pair; wherein a shift in FRET efficiency after adding the probe indicates a conformational change in the ribosome. In a preferred embodiment, solid surface is quartz. The first fluorescent label can be on a tRNA, an rRNA, an mRNA, or a ribosomal protein, which molecules can be directly labeled or indirectly labeled. For example, the rRNA can be genetically modified to comprise a peptide binding site, and wherein a fluorescently labeled peptide is bound to the modified rRNA. The fluorescently labeled peptide is selected from the group consisting of BIV Tat and HIV Rev. In another embodiment, the rRNA can be genetically modified to comprise a silent hybridization sequence, and wherein a fluorescently labeled oligonucleotide is bound to the silent hybridization sequence.

A further embodiment is a method of detecting a conformational change in a class 1 RF, the method comprising: providing a reaction mixture comprising an isolated, translationally-competent bacterial ribosome complex bound to a solid surface; adding to the reaction mixture a probe comprising a class 1 RF conjugated to a donor-acceptor pair of fluorescent labels; and measuring fluorescence resonance energy transfer (FRET) efficiency between the donor-acceptor pair; wherein a shift in FRET efficiency after adding the probe indicates a conformational change in the class 1 RF. The donor-acceptor pair is preferably Cy3/Cy5.

Another aspect of the invention is a method of assaying RF3 activity, the method comprising: providing a reaction mixture comprising an isolated, translationally-competent bacterial ribosome complex bound to a solid surface, wherein the ribosome complex comprises a first fluorescent label; adding to the reaction mixture a probe comprising a class 1 RF conjugated to a second fluorescent label, wherein the first fluorescent label and the second fluorescent label are a donor-acceptor pair; adding to the reaction mixture RF3; and measuring fluorescence resonance energy transfer (FRET) efficiency between the donor-acceptor pair; wherein a loss in FRET efficiency after adding the RF3 indicates RF3 activity by indicating release of the class 1 RF from the ribosome complex.

Another method of assaying RF3 activity comprises: providing a reaction mixture comprising an isolated, translationally-competent bacterial ribosome complex bound to a solid surface; adding to the reaction mixture a probe comprising a class 1 RF conjugated to a donor-acceptor pair of fluorescent labels; adding to the reaction mixture RF3; and measuring fluorescence resonance energy transfer (FRET) efficiency between the donor-acceptor pair by imaging the solid surface; wherein a loss in FRET efficiency after adding the RF3 indicates RF3 activity by indicating release of the class 1 RF from the ribosome complex.

A further method of assaying RF3 activity comprises: providing a reaction mixture comprising an isolated, translationally-competent bacterial ribosome complex bound to a solid surface; adding to the reaction mixture a probe comprising a class 1 RF conjugated to a donor-acceptor pair of fluorescent labels; adding to the reaction mixture RF3; and measuring fluorescence resonance energy transfer (FRET) efficiency between the donor-acceptor pair by imagining the reaction mixture; wherein high FRET efficiency after adding the RF3 indicates RF3 activity by indicating release of the class 1 RF from the ribosome complex.

Also provided is a method of identifying a compound for reducing nonsense-mediated decay of mRNA, the method comprising: providing a reaction mixture comprising an isolated, translationally-competent bacterial ribosome complex bound to a solid surface, wherein the ribosome complex comprises a first fluorescent label, and wherein the reaction mixture comprises an mRNA comprising a premature stop codon; adding to the reaction mixture a candidate compound; adding to the reaction mixture a probe comprising a class 1 RF conjugated to a second fluorescent label, wherein the first fluorescent label and the second fluorescent label are a donor-acceptor pair; and measuring fluorescence resonance energy transfer (FRET) efficiency between the donor-acceptor pair; wherein lack of FRET efficiency, low FRET efficiency, or transient FRET efficiency after adding the probe indicates that the candidate compound inhibits binding of the class 1 RF to the ribosome complex, thereby identifying a compound for reducing nonsense-mediated decay of mRNA.

Another method of the invention is a method of identifying a compound for inhibiting termination of protein synthesis at a premature stop codon, the method comprising: providing a reaction mixture comprising an isolated, translationally-competent bacterial ribosome complex bound to a solid surface, wherein the ribosome complex comprises a first fluorescent label, and wherein the reaction mixture comprises an mRNA comprising a premature stop codon; adding to the reaction mixture a candidate compound; adding to the reaction mixture a probe comprising a class 1 RF conjugated to a second fluorescent label, wherein the first fluorescent label and the second fluorescent label are a donor-acceptor pair; and measuring fluorescence resonance energy transfer (FRET) efficiency between the donor-acceptor pair; wherein lack of FRET efficiency, low FRET efficiency, or transient FRET efficiency after adding the probe indicates that the candidate compound inhibits binding of the class 1 RF to the ribosome complex, thereby identifying a compound for inhibiting termination of protein synthesis at a premature stop codon.

Additionally provided is a method of identifying a compound for reducing nonsense-mediated decay of mRNA, the method comprising: providing a reaction mixture comprising an isolated, translationally-competent bacterial ribosome complex bound to a solid surface, wherein the reaction mixture comprises an mRNA comprising a premature stop codon; adding to the reaction mixture a candidate compound; adding to the reaction mixture a probe comprising a class 1 RF conjugated to a donor-acceptor pair of fluorescent labels; and measuring fluorescence resonance energy transfer (FRET) efficiency between the donor-acceptor pair by imaging the reaction mixture; wherein high FRET efficiency after adding the probe indicates that the candidate compound inhibits binding of the class 1 RF to the ribosome complex, thereby identifying a compound for reducing nonsense-mediated decay of mRNA.

The invention also concerns a method of identifying a compound for reducing nonsense-mediated decay of mRNA, the method comprising: providing a reaction mixture comprising an isolated, translationally-competent bacterial ribosome complex bound to a solid surface, wherein the reaction mixture comprises an mRNA comprising a premature stop codon; adding to the reaction mixture a candidate compound; adding to the reaction mixture a probe comprising a class 1 RF conjugated to a donor-acceptor pair of fluorescent labels; and measuring fluorescence resonance energy transfer (FRET) efficiency between the donor-acceptor pair by imaging the solid surface; wherein lack of FRET efficiency or transient FRET efficiency after adding the probe indicates that the candidate compound inhibits binding of the class 1 RF to the ribosome complex, thereby identifying a compound for reducing nonsense-mediated decay of mRNA.

In another aspect, the invention provides a method of identifying a compound for inhibiting termination of protein synthesis at a premature stop codon, the method comprising: providing a reaction mixture comprising an isolated, translationally-competent bacterial ribosome complex bound to a solid surface, wherein the ribosome complex comprises a first fluorescent label, and wherein the reaction mixture comprises an mRNA comprising a premature stop codon; adding to the reaction mixture a candidate compound; adding to the reaction mixture a probe comprising a class 1 RF conjugated to a donor-acceptor pair of fluorescent labels; and measuring fluorescence resonance energy transfer (FRET) efficiency between the donor-acceptor pair by imaging the reaction mixture; wherein high FRET efficiency after adding the probe indicates that the candidate compound inhibits binding of the class 1 RF to the ribosome complex, thereby identifying a compound for inhibiting termination of protein synthesis at a premature stop codon.

The invention also provides a method of identifying a compound for inhibiting termination of protein synthesis at a premature stop codon, the method comprising: providing a reaction mixture comprising an isolated, translationally-competent bacterial ribosome complex bound to a solid surface, wherein the ribosome complex comprises a first fluorescent label, and wherein the reaction mixture comprises an mRNA comprising a premature stop codon; adding to the reaction mixture a candidate compound; adding to the reaction mixture a probe comprising a class 1 RF conjugated to a donor-acceptor pair of fluorescent labels; and measuring fluorescence resonance energy transfer (FRET) efficiency between the donor-acceptor pair by imaging the solid surface; wherein lack of FRET efficiency or transient FRET efficiency after adding the probe indicates that the candidate compound inhibits binding of the class 1 RF to the ribosome complex, thereby identifying a compound for inhibiting termination of protein synthesis at a premature stop codon.

BRIEF DESCRIPTION OF THE DRAWINGS

The patent or application as-filed contains at least one drawing executed in color. Copies of this patent or patent application publication with color drawing(s) will be provided by the United States Patent and Trademark Office upon request and payment of the necessary fee.

FIG. 1 shows termination and recycling in prokaryotic cells. The fundamental steps of stop-codon recognition and polypeptide release by RF1/2 (FIG. 1A), RF3-catalyzed dissociation of RF1/2 (FIG. 1B), and ribosome recycling by RRF, EFG and IF3 (FIG. 1C). Figure adapted from Horton et al. 2006.

FIG. 2 shows experimental model and reaction schemes for termination and recycling. FIG. 2A: smFRET signal between P-site (Cy3)tRNA$^{Phe}$ and L1(Cy5) demonstrated that during elongation, ribosomes exist in two global conformations: Global state 1 (GS1), encompassing a non-ratcheted ribosome, an open L1 stalk, and tRNAs bound in classical configurations; and global state 2 (GS2), encompassing a ratcheted ribosome, a closed L1 stalk, and tRNAs bound in hybrid configurations (Fei et al. 2008). FRET values for GS1 and GS2 are shown. FIG. 2B: Mechanistic model for termination. FIG. 2C: Mechanistic model for ribosome recycling. Later steps of recycling involving IF3 are not depicted. FIG. 2D: Cartoon diagrams of release complexes 1 (RC1) and 2 (RC2). Cartoon representations are defined in the legend.

FIG. 3 shows a mechanistic model for regulation of the GS1⇌GS2 dynamic equilibrium by Release Factor 1 (RF1), RF3, and Ribosome Recycling Factor (RRF). FIG. 3A: A post-hydrolysis release complex (RC) fluctuates stochastically between GS1 and GS2. FIG. 3B: RF1 specifically binds GS1 and prevents GS1→GS2 transitions of the RC, even after deacylation of P-site tRNA. FIG. 3C: RF3(GDP) initially interacts with an RF1-bound RC locked in GS1. GS1→GS2 transitions are suppressed until nucleotide-free RF3 binds GTP, which stabilizes the RC in GS2 and prevents GS2→GS1 transitions prior to GTP hydrolysis. FIG. 3D: A post-termination complex (PoTC), the natural substrate for RRF, fluctuates stochastically between GS1 and GS2. At concentrations near $K_{d,GS2}$, RRF preferentially binds GS2 and competes directly with the GS2→GS1 transition. At high RRF concentrations above $K_{d,GS1}$, RRF can also bind GS1 and actively promote the GS1→GS2 transition. Cartoon representations are shown as in FIG. 2.

FIG. 4 shows purification of RFs & RRF and fluorescent labeling of RF1. FIG. 4A: SDS-PAGE analysis of wild-type RF1, RF3, RRF, and RF1Δd1—cellular lysate after induced overexpression with 1 mM IPTG (lane 1), purified hexahistidine-tagged protein ('hexahistidine' disclosed as SEQ ID NO: 9) after one round of Ni2+-NTA chromatography (lane 2), and final protein preparations after affinity tag cleavage with TEV protease (lane 3). Overexpressed bands are boxed in red, and the asterisks in lane 1 for RF1 and RF1Δd1 denote the co-overexpressed methyltransferase (PrmC gene). FIG. 4B: Gel filtration analysis of Cy5 labeling of single-cysteine S167C RF1 (top) and cysteine-free RF1 (bottom). Only RF1 with an available cysteine residue is efficiently labeled.

FIG. 10 shows an experimental system. FIG. 10A: Fluorescently-labeled translation complexes are immobilized onto the surface of the flow cell via a biotin-streptavidin-biotin interaction that links the mRNA to the surface of a quartz microscope slide. FIG. 10B: Time-resolved fluorescence intensities are recorded using a lab-built total internal reflection fluorescence microscope capable of simultaneously recording single-fluorophore emission from approximately two hundred spatially localized single translation complexes at a real-time resolution of up to 20 msec/frame.

FIG. 11 shows steady-state smFRET between P-site (Cy3) tRNAPhe and three (Cy5)RF1 variants bound at the A site of a RC. Plots of Cy3 and Cy5 emission intensities vs. time are shown in green and red, respectively (first row), and their corresponding smFRET$_{ICy5/(ICy3+ICy5)}$ versus time traces are shown in blue (second row). Contour plots of the time evolution of population FRET are generated by superimposing the individual smFRET time traces (fourth row) and are plotted from tan (lowest population) to red (highest population). "N" indicates the number of traces that were used to construct each contour plot. (FIG. 11A) S167C, (FIG. 11B) S192C, (FIG. 11C) C257 (Cy5)RF1 variants. (FIGS. 11D-11F) Same as (FIG. 11A-11C), except in the presence of 100 μM paromomycin.

FIG. 15 shows a summary of smFRET data analysis. FIG. 15A shows smFRET plotted against time trajectory. FIG. 15B shows time evolution of population FRET. FIG. 15C shows a Markoc chain model as FRET plotted against time. FIG. 15D shows dwell time histograms.

FIG. 16 shows steady-state smFRET between L1(Cy5) ribosomes and deacylated P-site (Cy3)tRNAPhe. Cartoon representations of the RC depict the 30S and 50S subunits in tan and lavender, respectively, with the L1 stalk in dark blue, deacylated P-site tRNA as a brown line, RF1 and RF3 in light blue, and the Cy3 and Cy5 fluorophores as green and red stars, respectively (first row). The second through fourth rows are plotted as in FIG. 13. FIG. 16A shows puromycin-reacted RC. FIG. 16B shows binding of RF1 to puromycin-reacted RC. FIG. 16C shows binding of RF3(GDPNP) to puromycin-reacted RC.

FIG. 17 shows that RF1 blocks GS1→GS2 transitions and stabilizes GS1. FIG. 17A: RC2: lowered FRET values for GS1 and GS2 herein obscure the previously described broadened width of the FRET distribution caused by conformational heterogeneity of the L1 stalk in a post-translocation complex (Cornish et al. 2009; Fei et al. 2008). FIG. 17B: RC2 in the presence of 1 μM RF1. FIG. 17C: RC2$_{Pmn}$. 63% of smFRET vs. time trajectories fluctuate between 0.16 and 0.76 FRET. 24% remain stably centered at 0.16 FRET, and represent RCs that either failed to undergo the puromycin reaction or photobleached prior to undergoing the first GS1→GS2 transition. 13% sample only 0.76 FRET, and represent RCs whose fluorophore(s) photobleached prior to undergoing a GS2→GS1 transition. FIG. 17D: RC2$_{Pmn}$ in the presence of 1 μM RF1. 85% of trajectories remain stably centered at 0.16 FRET, corresponding to RF1-bound RCs. 9% fluctuate between 0.16 and 0.76 FRET, and represent RCs to which RF1 did not bind or dissociated from transiently. 6% sample only 0.76 FRET, and represent RCs to which RF1 did not bind and which failed to undergo a GS2→GS1 transition prior to fluorophore photobleaching. Data in all panels are displayed as in FIG. 13.

FIG. 18 shows representative kinetic analysis of RC2$_{Pmn}$ FIG. 18A: Using the HaMMy software suite (McKinney et al. 2006), raw smFRET data (blue) were converted into idealized smFRET data (red) with hidden Markov modeling. A representative smFRET trajectory is shown. FIG. 18B: A transition density plot was generated by plotting the "Starting FRET" vs. "Ending FRET" for each transition in a given dataset as contour plots of two-dimensional population histograms. Contours are shown from tan (lowest population) to red (highest population), with "A" indicating the number of transitions. FIG. 18C: One-dimensional smFRET histograms (red bars) were generated from the first 0.5 seconds of all traces. Thresholds for the 0.16 (0.10-0.22) and 0.76 (0.70-0.85) FRET states were defined by the full width at half height of each Gaussian fit (black line). FIGS. 18D, 18E: Population histograms of dwell time spent in the 0.16 (FIG. 18D) and 0.76 (FIG. 18E) FRET states (red bars) are well described by single exponential decays (black lines) of the form A×exp−(x/τ)+y$_0$. The following parameters from these two representative fits were obtained: y$_0$=4.5, A=703, τ=1.79±0.01 s (0.16 FRET state) and y$_0$=8.0, A=755, τ=0.615±0.009 s (0.76 FRET state), yielding k$_{GS1→GS2}$=0.492±0.003 s$^{-1}$ and k$_{GS2→GS1}$=1.32±0.02 s$^{-1}$ after correcting for photobleaching rates and the length of observation time. The R$^2$ of both fits was greater than 0.99. The final values of k$_{GS1→GS2}$=0.52±0.03 s$^{-1}$ and k$_{GS2→GS1}$=1.36±0.03 s$^{-1}$ are the averages and standard deviations of three independently recorded and equivalently analyzed datasets.

FIG. 19 shows that RF1 domain 1 is dispensable for RF1-mediated blocking of GS1→GS2 transitions. FIG. 19A: RC1 in the presence of 5 nM RF1Δd1(Cy5). FIG. 19B: RC2 in the presence of 1 μM RF1Δd1. 94% of trajectories remain stably centered at 0.16 FRET. 6% fluctuate between 0.16 and 0.76 FRET. FIG. 19C: RC2$_{Pmn}$ in the presence of 1 μM RF1Δd1. 86% of trajectories remain stably centered at 0.16 FRET. 10% fluctuate between 0.16 and 0.76 FRET. 4% sample only 0.76 FRET. Data in all panels are displayed as in FIG. 13.

FIG. 20 shows that RF3(GDP) interacts with an RF1-bound ribosome locked in GS1, and binding of GTP to RC-bound RF3 enables the GS1→GS2 transition. FIG. 20A: RC2$_{Pmn}$ in the presence of 1 μM RF3(GDPNP) (GDPNP is denoted as an orange hexagon). 73% of trajectories remain stably centered at 0.76 FRET, corresponding to RF3(GDPNP)-bound RCs. 5% sample only 0.16 FRET; 22% fluctuate between 0.16 and 0.76 FRET. The latter two subpopulations represent RCs that either failed to undergo the puromycin reaction or were photobleached prior to undergoing the first GS1→GS2 transition, or that did not bind RF3(GDPNP) and therefore spontaneously fluctuate between GS1 and GS2. This conclusion is confirmed by results from an RF3(GDPNP) titration (FIG. 21). FIG. 20B: RC2$_{RF1}$ in the presence of 1 μM RF1 and RF3(GDP). 98% of trajectories remain stably centered at 0.16 FRET. 2% fluctuate between 0.16 and 0.76 FRET. FIG. 20C: RC2$_{RF1}$ in the presence of 1 μM RF1 and nucleotide-free RF3. 99% of trajectories remain stably centered at 0.16 FRET. 1% fluctuate between 0.16 and 0.76 FRET. FIG. 20D: RC2$_{RF1}$ in the presence of 1 μM RF1, RF3(GDP) and 1 mM GTP. Only those trajectories exhibiting fluctuations between GS1 and GS2 (42%) make up the time-synchronized contour plot (fourth row), generated by post-synchronizing the onset of the first GS1→GS2 event in each trajectory to time=0.5 seconds. The remaining 58% of trajectories remain stably centered at 0.16 FRET. Data in all panels are displayed as in FIG. 13.

FIG. 23A: RC2$_{Pmn}$ in the presence of 1 μM RRF. 70% of trajectories fluctuate between 0.16 and 0.76 FRET. 23% remain stably centered at 0.76 FRET. 7% sample only 0.16 FRET. For RC2$_{Pmn}$ data analyzed similarly, 76% fluctuate between 0.16 and 0.76 FRET. 18% remain stably centered at 0.76 FRET. 6% sample only 0.16 FRET. The slight differences between these RC2$_{Pmn}$ subpopulations and those reported in FIG. 17C arise from automated, rather than manual, detection of strongly anti-correlated Cy3 and Cy5 intensity traces. Data are displayed as in FIG. 13. FIG. 23B: GS2/GS1 peak area ratio (K$_{eq}$) as a function of RRF concentration. The data was fit according to the equation in the text (red line), yielding the following parameters: C=0.6±0.1, K$_{d,GS1}$=12±2 μM and K$_{d,GS2}$=0.9±0.3 μM (R$^2$=0.99). FIG. 23C: k$_{GS1→GS2}$ and k$_{GS2→GS1}$ as a function of RRF concentration. Error bars represent the standard deviation from at least three independent experiments.

FIG. 31 shows the smFRET trajectory of 141/256-Cy3/Cy5 RF1, alone and bound to the RC.

FIG. 32 shows the smFRET trajectory of 328/256-Cy3/Cy5 RF1, alone and bound to the RC.

FIG. 33 shows the smFRET trajectory of 167/328-Cy3/Cy5 RF1, alone and bound to the RC.

DETAILED DESCRIPTION OF THE INVENTION

Figure 4C:
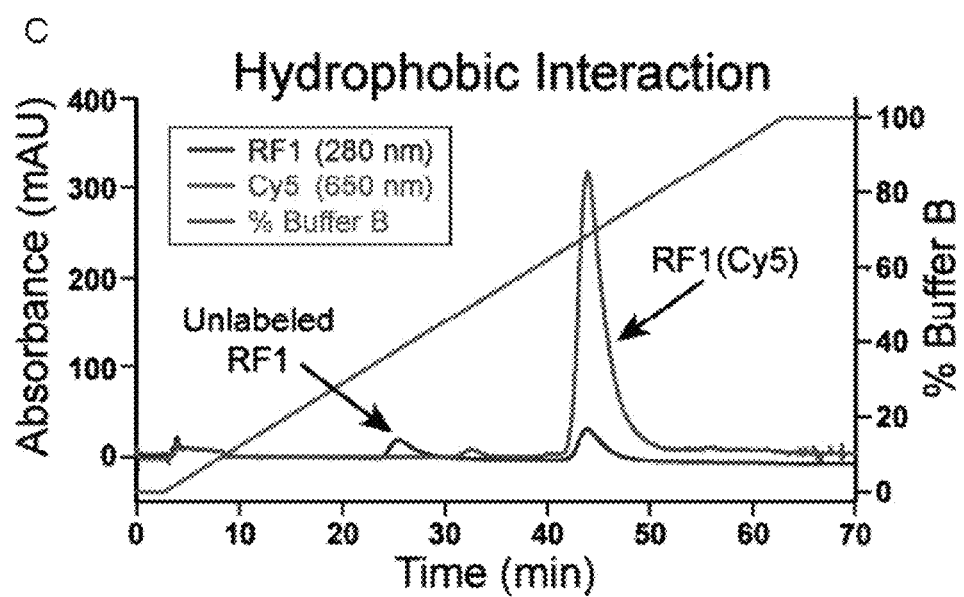
FIG. 4C: Separation of RF1(Cy5) from unlabeled RF1. Taking advantage of the added hydrophobicity from the Cy5 fluorophore, 100% homogenously-labeled RF1(Cy5) was purified away from unlabeled protein by injecting protein fractions from the previous gel filtration run onto a TSKgel Phenyl-5PW hydrophobic interaction column. RF1Δd1 (Cy5) was prepared in the same manner as RF1(Cy5).

The use of a purified, in vitro, *Escherichia coli*-based system for examining ribosome-catalyzed protein synthesis has previously been described. (See U.S. Pat. No. 7,297,532 and U.S. Pub. No. 2004/0023256.) The invention relates to a system and methods for measuring ribosomal dynamics during the termination reaction of protein synthesis. The present invention also relates to site specific labeling of ribosomes, tRNAs, and translation factors. The ability to immobilize the ribosomal complex and to detect single molecules provides unique insight into the termination of protein synthesis.

Using the methods of the invention, it is possible to examine the mechanism of class 1 RF interaction with the ribosome and high fidelity of stop codon recognition before, during, and after polypeptide hydrolysis. The methods described herein are also useful for examining the mode of action of inhibitors of translation termination. Some methods are particularly adapted for studying class 1 RF-catalyzed translation termination.

In one aspect, the invention provides methods for labeling one or more translation RFs with one or more fluorescent probes, such that the labeled RF retains an activity that is about the same as an unlabelled RF. Such labeled RFs can be used to measure translation termination according to the methods described herein. In a particular aspect, the invention relates to the use of fluorescently-labeled Release Factor 1 (RF1) constructs to probe RF1 conformational dynamics and substrate selection, using single-molecule fluorescence microscopy, preferably single molecule Förster (or fluorescence) resonance energy transfer (smFRET).

For example, the invention provides methods for measuring smFRET signals between RF1-tRNA and ribosome-tRNA, an intramolecular smFRET signal for RF1. Measurement of $smFRET_{RF1-tRNA}$, and optionally, $smFRET_{L1-tRNA}$ signals, can be used to determine how RF1, RF3, and RRF influence and regulate the GS1/GS2 equilibrium within the *Escherichia coli* ribosome. The smFRET measurements can be performed at a timescale corresponding to conformational changes that occur during translation termination and ribosome recycling.

Because the signal measured can be a fluorescence signal, the methods described herein can be used to obtain high sensitivity readings. The methods can be performed using small amounts of material, and can be easily used for high-throughput screens.

These methods and system are suitable for use in identifying compounds capable of inhibiting protein synthesis termination, particularly at one or more premature stop codons. For example, the methods for measuring ribosomal dynamics can be adapted to serve as a high-throughput platform for characterizing the efficacy of pharmacological drugs/agents designed to inhibit or perturb the termination reaction. Such methods can comprise monitoring fluorescently-labeled class 1 RF reporters as described herein. In some embodiments, the described methods can be used in a high-throughput manner to screen compounds capable of inhibiting peptide hydrolysis by class 1 RF.

Definitions

The singular forms "a," "an," and "the" include plural references unless the content clearly dictates otherwise.

A "class 1 release factor" includes prokaryotic RF1 and RF2 (RF1/2) and eukaryotic RF1 (eRF1).

A "fluorescent label" is a small molecule, such as a dye or peptide, that comprises a fluorophore. Examples of fluorescent labels suitable for use in the invention include, but are not limited to, fluorescein; rhodamine; cyanine; coumarin; and derivatives thereof.

Derivatives of fluorescein include, for example, fluorescein isothiocyanate (FITC), NHS-fluorescein, 5-carboxyfluorescein, 6-carboxyfluorescein, carboxy-naphthofluorescein, 5-maleimido-fluorescein, 5-iodoacetamidofluorescein, Oregon Green, Tokyo Green, DyLight 488, carboxy tetrachloro fluorescein (TET), NHS-fluorescein, 5 and/or 6-carboxy fluorescein (FAM), carboxyfluorescein succinimidyl ester, 5-(or 6-) iodoacetamidofluorescein, and 5-{[2(and 3)-5-(Acetylmercapto)-succinyl]amino}fluorescein (SAMSA-fluorescein).

Derivatives of rhodamine include, for example, sulforhodamine, tetramethylrhodamine (TMR), octadecylrhodamine, Lissamine rhodamine B sulfonyl chloride, Texas red sulfonyl chloride, 5- and/or 6-carboxy rhodamine (ROX).

Derivatives of cyanine include, for example, 1,1'-dioctadecyl-3-3,3,3',3'-tetramethyl-indocarbocyanine, 3,3'-ditetradecyloxacarbocyanine, carboxymethylindocyanine-N-hydroxysuccinimidyl ester, 3,3(')-diethyloxadicarbocyanine iodide (DODCI), merocyanine 540 (MC 540), and the Cy dyes, such as Cy3 and Cy5.

Derivatives of couramin include, for example, (7-(dimethylamino)coumarin-4-yl)-acetyl, 7-amino-methyl-coumarin, 7-Amino-4-methylcoumarin-3-acetic acid (AMCA), 3(4-isothiocyanatophenyl)7-diethyl-4-amino-4-methylcoumarin, and 7-diethylamino-3-(4'-maleimidylphenyl)-4-methylcoumarin.

Other dyes that can be useful in the invention include 2-anthracene N-acetylimidazole; B-phycoerythrin; 4-dimethylaminophenylazo-phenyl-4'-maleimide; dansylaziridine; N-(4-dimethylamino-3,5-dinitrophenyl)maleimide; dimethylamino-4-maleimidostilbene; N-(2,5'-dimethoxystilben-4-yl)-maleimide; 2,4-dinitrophenyl; 1,N.sup.6-ethenoadenosine; 5-(iodoacetetamido)eosin; eosin-5-isothiocyanate; eosin N-acETYLIMIDAZOLE; eosin maleimide; erythrosin-5'-isothiocyanate; eosin thiosemicarazide; 1,5-difluoro-2,4'-dinitrobenzene; 4,4'-difluoro-3,3'-dinitrophenylsulfone; fluorescein thiosemicarbazide; 2-(4'-iodoacetamido)anilino)napthalene-6-sulfonic acid; 5-(2-((iodoacetyl)amino)ethyl)amino)-napthlene-1-sulfonic acid; N-((2-(iodoacetoxy)ethyl)-N-methyl)amino-7-nitrobenz-2-oxa-1,3-diaz-ole; 4-(iodoacetamido)salicylic acid; lissaminerhodamine; Lucifer yellow; monobromobiamane; MNA, (2-methoxy-1-naphthyl)-methyl; 2-napthoxyacetic acid; 7-nirto-2,1,3-benzoxadiazol-4-yl; N-cyclohexyl-N'-(1-pyrenyl)carbodiimide; PM, N-(1-pyrene)-maleimide; trinitrophenyl; Texas Red and derivatives thereof. Alexa Fluor®-dyes, commercially available from Molecular Probes (Eugene, Oreg.) can be used, for example, Alexa Fluor®-350, Alexa Fluor®-430, Alexa Fluor®-488, Alexa Fluor®-532, Alexa Fluor®-546, Alexa Fluor®-568, Alexa Fluor®-594, Alexa Fluor®-633, Alexa Fluor®-647, Alexa Fluor®-660 and Alexa Fluor®-680. Other fluorophores suitable for use with the methods described herein are known to those of skill in the art. For a general listing of useful fluorophores, see Hermanson, G. T., Bioconjugate Techniques (Academic Press, San Diego, 1996).

A "donor-acceptor pair" is a pair of fluorescent molecules suitable for FRET. One molecule contains a donor fluorophore and the other molecule contains an acceptor fluorophore. The donor, in its electronic excited state, can transfer energy to the acceptor when the two are in close proximity, typically less than about 10 nm. The transfer of energy occurs through non-radiative dipole-dipole coupling. Examples of donor-acceptor pairs include coumarin 4/coumarin 343; 6-carboxyfluorescein/6-carboxy-X-rhodamine; 5,7-dimethyl-BODIPY/5-(4-phenyl-1,3-butadienyl)BODIPY; and Cy3/Cy5.

An "inactive region" of a protein is one that is not essential to the protein's structure or function. Regions that can be essential can include a binding domain, a regulatory domain, a catalytic domain, a recognition domain, etc. Amino acid substitutions in an inactive region of a protein do not affect the protein's biological activity. Inactive regions can be identified by one of ordinary skill in the art without undue experimentation by performing, for example, routine point mutation studies on proteins of interest.

The term "conformational change" refers to the physical transition in shape of a macromolecule or macromolecular complex in response to environmental factors. Such environmental factors can include changes in ligand binding or release, pH, temperature, ion concentration. A conformational change in RF1 refers to the transition between the "open" and the "closed" states of RF1. See FIG. 12. A conformational change in a ribosome refers to changes in the positions of ribosomal complex components in relation to one another. For example, a conformational change in a ribosome includes the movements of tRNAs from their classical to their hybrid ribosome binding configurations, movement of the ribosomal L1 stalk from an open to a closed conformation, and the counterclockwise rotation, or ratcheting, of the small (30S) ribosomal subunit relative to the large (50S) subunit.

For the purposes of the present invention, ribosomes may be prokaryotic or eukaryotic. The term "ribosome complex" is used herein to refer to a ribosome in association with one or more biomolecules associated with translation, including, without limitation, mRNA, tRNAs, nascent polypeptide, elongation and initiation factors.

Ribosomes are ribonucleoprotein particles that perform protein synthesis using a messenger RNA template. The ribosome, a 70S particle in prokaryotes, is composed of two sub-units. The small subunit (30S) mediates proper pairing between transfer RNA (tRNA) adaptors and the messenger RNA, whereas the large subunit (50S) orients the 3 ends of the aminoacyl (A-site) and peptidyl (P-site) tRNAs and catalyzes peptide bond formation. The ribosome translocates directionally along mRNA in 3 nucleotide steps to read the sequential codons.

As used herein, "translational competence" is the ability of a ribosome to catalyze at least one peptide bond formation where the tRNA and mRNA template are properly paired, and may include the ability to catalyze translation of a complete mRNA into the appropriate protein.

By "solid surface," "solid substrate" or "solid support" is meant any surface to which the ribosome or ribosome complexes are attached. Where the ribosome is to be fluorescently labeled, a preferred substrate is quartz. Other solid supports include glass, fused silica, acrylamide; plastics, e.g. polytetrafluoroethylene, polypropylene, polystyrene, polycarbonate, and blends thereof, and the like; metals, e.g. gold, platinum, silver, and the like; etc. The substrates can take a variety of configurations, including planar surfaces, beads, particles, dipsticks, sheets, rods, etc.

In one embodiment, the substrate comprises a planar surface, and ribosomes or ribosome complexes are attached to the surface, e.g. in a solid or uniform pattern, or in an array in a plurality of spots. The density of attached particles on the substrate will be such that a signal from a label can be detected. Where the complexes are spotted on the array, the spots can be arranged in any convenient pattern across or over the surface of the support, such as in rows and columns so as to form a grid, in a circular pattern, and the like, where generally the pattern of spots will be present in the form of a grid across the surface of the solid support. The total number of spots on the substrate will vary depending on the sample to be analyzed, as well as the number of control spots, calibrating spots and the like, as may be desired.

In another embodiment, the substrate is a collection of physically discrete solid substrates, e.g. a collection of beads, individual strands of fiber optic cable, and the like. Each discrete substrate can have complexes distributed across the surface or attached in one or more probe spots on the substrate. The collection of physically separable discrete substrates may be arranged in a predetermined pattern or may be separated in a series of physically discrete containers (e.g., wells of a multi-well plate).

Ribosome Attachment to Substrate

Translationally competent ribosomes or ribosome complexes are attached to a solid surface at a specific attachment site, where the attachment site is one of a specific binding pair. In one embodiment, the attachment site is other than the nascent polypeptide component that is being translated. The attachment site may be naturally occurring, or may be introduced through genetic engineering. Pre-formed ribosome complexes can be attached to the surface, or complexes can be assembled in situ on the substrate. The ribosome or ribosome complex is usually stably bound to the substrate surface for at least about 1 minute, and may be stably bound for at least about 30 minutes, 1 hour, or longer, where the dissociation rate of the complexes depends on solution conditions and ligand-bound state of the ribosome. Complexes are usually more stable at higher $Mg^{2+}$ concentrations and monovalent ion concentrations. The complex stability may also be increased at lower pH, by the presence of a P-site tRNA, and by addition of an acyl-aminoacid on the tRNA.

In one embodiment, the attachment site is a nucleic acid sequence present in one of the ribosomal RNAs or on the mRNA, where a polynucleotide having a sequence complementary to the attachment site acts a linker between the ribosome complex and the solid surface. A convenient nucleic acid attachment site is mRNA, usually at the 5' or 3'-end, where a complementary polynucleotide may hybridize, for example, to the untranslated region of the mRNA.

Alternative nucleic acid attachment sites include rRNA regions of conserved A-form helical secondary structure where the primary sequence of the helical region is not evolutionarily conserved. Examples include surface-accessible hairpin loops, particularly those regions that are not involved in tertiary structure formation. Such regions may be identified by a comparison of rRNA sequences to determine a lack of sequence similarity. Criteria include a helix of at least about 5 nt. in length, with a non-conserved nucleotide sequence.

The surface accessible loop may serve as an attachment site, or more preferably, the rRNA will be genetically modified to expand stem loop sequences by from about 6 to about 20 nucleotides, more usually from about 8 to about 18 nucleotides. Preferred rRNA suitable for such modification is the prokaryotic 16S rRNA or the corresponding eukaryotic 18S rRNA, although the 23S and 28S rRNA may also find use.

Specific sites of interest for the introduction of a stem loop expansion for an attachment site include, without limitation, the 16S rRNA H6, H10, H26, H33a, H39 and H44 loops (Wimberly et al. (2000) Nature 407(6802):327-39). In 23S rRNA, the H9, H68 and H101 may be selected (Ban et al. (2000) Science 289(5481): 905-20).

The polynucleotide having a sequence complementary to the attachment site may be indirectly coupled to the substrate through an affinity reagent comprising two binding partners. Examples of suitable affinity reagents include biotin/avidin or streptavidin; antibody/hapten; receptor/ligand pairs, as well as chemical affinity systems. For example, the substrate surface may be derivatized with avidin or streptavidin, and a ribosome complex comprising a biotin moiety present on a complementary polynucleotide is then contacted with the substrate surface, where specific attachment then occurs.

Where the polynucleotide having a sequence complementary to the attachment site is directly coupled to the substrate, various chemistries may be employed to provide a covalent bond, including homo- or heterobifunctional linkers having a group at one end capable of forming a stable linkage to the polynucleotide, and a group at the opposite end capable of forming a stable linkage to the substrate. Illustrative entities include: azidobenzoyl hydrazide, N-[4-

(p-azidosalicylamino)butyl]-3'-[2'-pyridyldithio]propionamide), bis-sulfosuccinimidyl suberate, dimethyladipimidate, disuccinimidyltartrate, N-.gamma.-maleimidobutyryloxysuccinimide ester, N-hydroxy sulfosuccinimidyl-4-azidobenzoate, N-succinimidyl [4-azidophenyl]-1,3'-dithiopropionate, N-succinimidyl [4-iodoacetyl]aminobenzoate, glutaraldehyde, NHS-PEG-MAL; succinimidyl 4-[Nmaleimidomethyl]cyclohexane-1-carboxylate; 3-(2-pyridyldithio)propionic acid N-hydroxysuccinimide ester (SPDP) or 4-(N-maleimidomethyl)-cyclohexane-1-carboxylic acid N-hydroxysuccinimide ester (SMCC). To improve the stability, the substrate may be functionalized to facilitate attachment. Modes of surface functionalization include silanization of glass-like surfaces by 3-aminopropyltriethoxysilane, 3-mercaptopropyltrimethoxysilane, 3-isocyanatopropyltriethoxysilane, 3-isothiocyanonatopropyltriethoxysilane, 2-(4-chlorosulfonylphenyl)ethyltrimethoxysilane, 3-bromopropyltrimethoxysilane, methacryloxymethyltrimethylsilane; and the like. Polymer coating may be achieved with polyvinyl alcohol, polyethyleneimine, polyacrolein, polyacrylic acid, etc.

An alternative attachment strategy utilizes ribosomal proteins, which may be modified to include a site for biotinylation, or other binding moieties. Translationally competent ribosomes or ribosome complexes can be attached to a solid surface at a specific attachment site, where the attachment site is one of a specific binding pair. The ribosomes or ribosome complexes may be fluorescently labeled. The attachment site can be other than the nascent polypeptide component that is being translated. The attachment site may be naturally occurring, or may be introduced through genetic engineering. Pre-formed ribosome complexes can be attached to the surface, or complexes can be assembled in situ on the substrate.

It will be understood by those of skill in the art that other components may be required for translation, including, for example, amino acids, nucleotide triphosphates, tRNAs and aminoacyl synthetases, or aminoacyl-loaded tRNAs; elongation factors and initiation factors.

In addition the reaction mixture may comprise enzymes involved in regenerating ATP and GTP, salts, polymeric compounds, inhibitors for protein or nucleic acid degrading enzymes, inhibitor or regulator of protein synthesis, oxidation/reduction adjuster, non-denaturing surfactant, buffer component, spermine, spermidine, etc. The reaction mixture may further comprise competitive tRNAs, agents such as antibiotics that affect translation, variations in reaction conditions, e.g. salt concentrations, concentration of factors, temperature, etc. Salts suitable for use in a reaction mixture, can include, but are not limited to, potassium, magnesium, ammonium and manganese salt of acetic acid or sulfuric acid, and some of these may have amino acids as a counter anion. Polymeric compounds suitable for use in a reaction mixture can include, but are not limited to, polyethylene glycol, dextran, diethyl aminoethyl, quaternary aminoethyl and aminoethyl. Oxidation/reduction adjuster suitable for use in a reaction mixture, can include, but are not limited to, dithiothreitol, ascorbic acid, glutathione and/or their oxides. Also, a non-denaturing surfactant, e.g. Triton X-100 may be used at a concentration of 0-0.5 M. Spermine and spermidine may be used for improving protein synthetic ability. Preferably, the reaction is maintained in the range of pH 5-10 and a temperature of 20° C. to 50° C., and more preferably, in the range of pH 6-9 and a temperature of 25° C. to 40° C.

Ribosome Function

Genes are expressed as proteins in the cell through a process termed translation. Translation occurs on the ribosome, a multicomponent enzyme that uses amino acid substrates in order to synthesize proteins, which are linear polymers of amino acids. The overall process of translation can be divided into four stages: (1) initiation, in which a protein synthesis reaction commences using the first amino acid, (2) elongation, in which amino acid substrates are linearly added to the protein, (3) termination, in which the fully synthesized protein is released from the ribosome, and (4) recycling, in which the ribosome is prepared for a new round of initiation. All of these stages of translation are highly regulated by the cell.

Termination is triggered when the ribosome encounters a stop codon at the end of a messenger RNA, signaling the end of the mRNA-encoded protein product. While sense codons are typically decoded by the ribosome using aminoacyl-transfer RNA substrates (one for each of the twenty naturally-occurring amino acids), stop codons are instead decoded by the ribosome using RFs. Recognition, selection, and binding of an RF to the ribosome in response to a stop codon results in the release (via a hydrolysis reaction catalyzed by the RF) of the fully-synthesized, mRNA-encoded protein product from the ribosome. Other features of ribosome function include high-accuracy stop codons decoding using RFs, the coupling of stop-codon recognition to the hydrolysis of the fully synthesized protein, and the hydrolysis reaction itself.

Ribosome, transfer RNA (tRNA), and translation factor structural rearrangements play important mechanistic roles throughout protein synthesis. Conformational changes of the translational machinery include the movements of tRNAs from their classical to their hybrid ribosome binding configurations, movement of the ribosomal L1 stalk from an open to a closed conformation, and the counterclockwise rotation, or ratcheting, of the small (30S) ribosomal subunit relative to the large (50S) subunit (Agirrezabala et al. 2008; Julian et al. 2008; Connell et al. 2007; Gao et al. 2007; Gao et al. 2005a; Valle et al. 2003; Frank et al. 2000).

FIGS. 1A and 1B delineate the fundamental biochemical steps in the termination pathway. In the early steps of termination, a class 1 release factor binds to the ribosome in response to a messenger RNA (mRNA) stop codon and catalyzes release of the nascent polypeptide from ribosome-bound peptidyl transfer RNA (pep-tRNA). In the later steps of termination, a class II release factor (RF3) binds to the ribosomal release complex (RC; also called the ribosomal termination complex) and catalyzes dissociation of RF1/2. Interpretation of recent biochemical (Zavialov et al. 2001) and structural (Gao et al. 2007a) studies suggest that RF3 drives conformational changes of RF1/2 and the ribosome that lead to dissociation of RF1/2, and ultimately RF3, from the RC. Ribosome recycling, which involves splitting apart of the ribosomal subunits and dissociation of the deacylated-tRNA(s) and the mRNA, is the final stage of translation. Although the exact mechanism and order of events is not known, ribosome recycling factor (RRF), elongation factor G (EFG), and initiation factor 3 (IF3) have all been shown to participate in this process; inference from structural comparisons suggests that conformational dynamics of these factors and the ribosome, including ribosome ratcheting, play important mechanistic roles in recycling.

Numerous conformational changes of the RFs and the ribosome are functionally important during this process. These include conformational changes of RF1/2 during stop-codon recognition at the DC, allosteric signaling of the recognition event from the decoding center (DC) to the ribosomal peptidyltransferase center (PTC), and subsequent hydrolysis of the ester bond between the nascent polypeptide and the tRNA at the peptidyltRNA binding (P) site of the PTC (Petry et al. 2005; Zavialov et al. 2002).

The ribosome ensures high fidelity in aminoacyl-tRNA (aa-tRNA) selection (error frequency of $10^{-4}$) by coupling mRNA codon/aa-tRNA anticodon base pairing with elongation factor Tu (EF-Tu)-catalyzed GTP hydrolysis in a kinetic discrimination mechanism (Rodnina et al. 2005; Pape et al. 1998). The ribosome achieves can achieve even higher accuracy of RF1/2 selection (error frequency of $10^{-5}$ to $10^{-6}$, depending on the stop codon) (Jorgensen et al. 1993), without the use of either base pairing between the stop-codon and RF1/2 or factor-catalyzed GTP hydrolysis. Genetic and biochemical experiments have shown that a bacterially-conserved tripeptide motif (P(V/A)T in RF1 and SPF in RF2) is responsible for specific discrimination of the three stop-codons by RF1/2 (Nakamura et al. 2002; Chavatte et al. 2001; Ito et al. 2000; Poole et al. 1998). Structural analysis has placed the tripeptide motifs of RF1 and RF2 in proximity (Petry et al. 2005; Rawat et al. 2003; Klaholz et al. 2003) to the corresponding mRNA stop codons at the DC.

Biochemical analysis shows that mRNA nucleotides both upstream and downstream of the stop codon (e.g. "codon context") can affect termination efficiency (Bjornsson et al. 1996; Bonetti et al. 1995; Poole et al. 1995) and that mutations in RF2 within the domain containing the tripeptide motif, but not within the tripeptide motif itself, can trigger nascent polypeptide release at non-cognate stop codons as well as at sense codons (Uno et al. 2002; Ito et al. 1998). With regard to polypeptide hydrolysis, a conserved RF1/2 domain containing a universally-conserved GGQ tripeptide motif is required for ester bond-hydrolysis (Zavialov et al. 2002; Frolova et al. 1999). In bacteria, the glutamine within the GGQ motif is post-translationally N5-methylated and this modification is required for efficient pep-tRNA hydrolysis (Dincbas-Renqvist et al. 2000). Structural studies of RF1/2 bound to a RC have localized the GGQ motif at the PTC. The process through which the stop-codon recognition signal is transmitted from the DC to the PTC remains unknown and may involve large-scale conformational changes in RF1/2 between a "closed" and an "open" conformation (Petry et al. 2005; Klaholz et al. 2003; Rawat et al. 2003).

In the next step of the termination pathway, RF3 catalyzes the dissociation of RF1/2 from the post-hydrolysis RC (Zaviolov et al. 2002; Zaviolov et al. 2001). Briefly, RF3 binds to the RC in the GDP form and undergoes GDP/GTP-exchange, with the post-hydrolysis, RF1/2-bound RC acting as its guanine nucleotide exchange factor. GDP/GTP-exchange leads to an RF3 conformational change that, likely coupled to ribosome and RF1/2 conformational changes, leads to dissociation of RF1/2. Subsequent GTP hydrolysis by RF3 is accompanied by an additional conformational change of RF3 that, again possibly coupled to ribosome conformational changes, leads to dissociation of RF3 from the RC. Structural evidence supporting these conformational changes comes exclusively from comparisons of low-resolution cryogenic electron microscopic (cryo-EM) structures imaged in the absence or presence of bound RF3.

Several large-scale conformational changes of the RC may accompany GDP/GTP-exchange of RF3 and mediate the dissociation of RF1/2. Such changes may include: (1) a transition of the newly deacylated-tRNA at the P site from a classical P/P tRNA configuration, in which the tRNA anticodon is bound at the P site of the small (30S) ribosomal subunit and the tRNA acceptor end is bound at the P site of the large (50S) ribosomal subunit, to an intermediate hybrid P/E tRNA configuration (this is an intermediate configuration because the tRNA anticodon is bound at the P site of the 30S and the tRNA acceptor end is bound at deacylated, or exit (E), tRNA binding site of the 50S subunit); (2) an ~20 Å movement of the ribosomal L1 stalk into the intersubunit space, where it is observed to directly contact the P/E tRNA; and (3) a counterclockwise rotation of the 30S relative to the SOS, termed ratcheting (Gao et al. 2007a; Klaholz et al. 2004). A similar conformational change of the ribosome may occur during the EFG-catalyzed translocation step of the elongation cycle (Connell et al. 2007; Valle et al. 2003; Frank et al. 2000).

Using an L1 stalk-tRNA single-molecule Förster (or fluorescence) resonance energy transfer ($smFRET_{L1\text{-}tRNA}$) signal, stochastic movements of the L1 stalk between open and closed conformations within a pre-translocation ribosomal elongation complex were shown to be coupled to the fluctuations of P-site tRNA between classical and hybrid configurations (Fei et al. 2008). Taken together with ensemble intersubunit FRET data correlating the classical and hybrid tRNA binding configurations with the non-ratcheted and ratcheted conformations of the ribosomal subunits (Ermolenko et al. 2007), respectively, $smFRET_{L1\text{-}tRNA}$ data shows that the entire pre-translocation complex spontaneously and reversibly fluctuates between two major conformational states: global state 1 (GS1) and global state 2 (GS2) (Fei et al. 2008) (FIG. 2A). Determining how the GS1/GS2 equilibrium is coupled to the activities of release and ribosome recycling factors is useful for understanding the role of conformational dynamics of the translational machinery in the termination and ribosome recycling. The results described herein show that the global state of the ribosome is a mechanistic feature of translation factors and a regulatory strategy that is used throughout protein synthesis.

The P/P-to-P/E tRNA transition, movement of the L1 stalk to contact the P/E tRNA, and ratcheting of the ribosome are all directly coupled during elongation, each representing a dynamic feature of the same global conformational change of the elongation complex. smFRET studies of pre-translocation complexes have reported spontaneous and reversible intersubunit rotation between two major conformations, non-ratcheted and ratcheted (Cornish et al. 2008), as well as fluctuations of the L1 stalk between open and closed conformations (Cornish et al. 2009). Collectively, these studies revealed that the equilibrium constants governing the non-ratcheted ratcheted ribosome and open closed L1 stalk equilibria are closely correlated (Cornish et al. 2009), and that these dynamic processes are coupled. Cryogenic electron microscopic (cryo-EM) analysis using classification methods has revealed the existence of both GS1- and GS2-like conformations within a single pretranslocation sample without any detectable intermediates (Agirrezabala et al. 2008; Julian et al. 2008). The ~2.5 MDa biomolecular machine can include additional dynamic complexity beyond the GS1 GS2 model. It is possible that short-lived and/or rarely-sampled intermediates have thus far eluded detection by smFRET experiments and cryo-EM reconstructions. Thus, the GS1 GS2 model provides a useful framework for investigating the dynamics of the translating ribosome.

Reversible transitions between GS1 and GS2 are prompted by peptidyltransfer to either an A-site aminoacyl-tRNA (aa-tRNA) or to the antibiotic puromycin (Fei et al. 2008). Puromycin mimics the 3'-terminal residue of aa-tRNA(Traut et al. 1964), but unlike a fully intact aa-tRNA, dissociates rapidly from the A site upon peptidyltransfer.

Therefore, deacylation of P-site peptidyl-tRNA alone, regardless of A-site occupancy, is necessary and sufficient to trigger GS1 GS2 fluctuations. Binding of the GTPase ribosomal translocase, elongation factor G (EF-G), stabilizes GS2 (Cornish et al. 2008; Fei et al. 2008), helping to control the directionality of tRNA movements during translocation. Thus, precise regulation of the GS1 GS2 equilibrium by EF-G is a fundamental feature of translation elongation.

Beyond elongation, a deacylated tRNA also occupies the P site during translation termination and ribosome recycling. Accordingly, regulation of the GS1 GS2 equilibrium may be mechanistically important throughout these additional stages of protein synthesis. During termination, a stop codon in the A site of a ribosomal RC promotes binding of a class I release factor (RF1 or RF2), which catalyzes hydrolysis of the nascent polypeptide, thereby deacylating the P-site peptidyl-tRNA. RF1/2 remains tightly bound to the post-hydrolysis RC, and a class II release factor (RF3, a GTPase) is required to catalyze RF1/2 dissociation (Freistroffer et al. 1997). RF3(GDP) binds to the RF1/2-bound RC, and rapid dissociation of GDP yields a high-affinity complex between nucleotide-free RF3 and the RF1/2-bound RC (Zavialov et al. 2001). Binding of GTP to RF3 then catalyzes RF1/2 dissociation, and subsequent GTP hydrolysis leads to RF3 (GDP) dissociation (Zavialov et al. 2001), yielding a ribosomal posttermination complex (PoTC) (FIG. 2B). During ribosome recycling, the PoTC is initially recognized by ribosome recycling factor (RRF) and dissociated into its component 30S and 50S subunits by the combined action of RRF and EF-G in a GTP-dependent reaction (Hirokawa et al. 2005; Peske et al. 2005; Zavialov et al. 2005) (FIG. 2C).

Cryo-EM analysis shows that ribosome and tRNA structural rearrangements analogous to those observed in pre-translocation complexes (e.g. between GS1 and GS2) occur during both termination and ribosome recycling (Barat et al. 2007; Gao et al. 2007a; Rawat et al. 2006; Gao et al. 2005; Klaholz et al. 2004). The GS1 GS2 dynamics of the post-hydrolysis RC and PoTC have not been directly investigated. The continuous presence of a deacylated P-site tRNA throughout termination and ribosome recycling indicates that these ribosomal complexes possess the intrinsic capability to undergo spontaneous GS1 GS2 fluctuations (Fei et al. 2008).

FIG. 1C outlines the fundamental biochemical steps in the recycling pathway. During recycling, RRF, EFG, and IF3 act to split the PoTC into its component 30S and 50S subunits and dissociate the remaining deacylated-tRNA(s) and mRNA from the 30S in preparation for a new round of translation initiation (Seshadri et al. 2006; Wilson et al. 2002).

Deregulation of Termination in Malignancies

The role of termination in regulating gene expression and the effect of deregulation in various malignancies. One feature of termination is the competition between RF1/2 and so-called nonsense suppressor tRNAs for binding to stop codons. Nonsense suppressor tRNAs are naturally occurring or mutant tRNAs that compete with RF1/2 for binding to ribosomes in response to a stop codon and lead to ribosomal frameshifting or stop-codon read through (nonsense suppression) events. Cellular levels of RFs and their efficiencies of termination at specific stop codons are important for regulating the competing processes of polypeptide release, ribosomal frame shifting, and nonsense suppression, a process that can be important in the expression of both host and viral pathogen-encoded gene products (Bertram et al. 2001; Tate et al. 1992). Depletion of eRF1 or eRF3 in human HeLa cells and eRF1 in *S. cerevisiae* results in an increase in nonsense suppression (Janzen et al. 2004; Stansfield et al. 1996). The simultaneous overexpression of eRF1 and eRF3 in yeast strains containing suppressor tRNAs produces a marked anti-suppressor phenotype (Stansfield et al. 1995). Furthermore, bioinformatic and in vivo studies have demonstrated that the translational stop signal in both prokaryotes and eukaryotes extends beyond the traditional three-nucleotide mRNA codon (Tate et al. 1996) and that the efficiencies of both polypeptide release and nonsense suppression depend on the relative strength of termination at specific stop codon contexts (Poole et al. 1995; Martin et al. 1989). Thus, inefficient termination due to depleted RF levels or poor stop codon contexts along with the competing processes of frameshifting and nonsense suppression enable careful regulation of gene expression at the level of translation termination (Tate et al. 1992).

Deletions, mutations, and other forms of eRF1 and eRF3 deregulation are associated with a variety of malignancies and cancers. For example, the region of human chromosome 5, which contains the functional copy of the human eRF1 gene is frequently deleted in malignant myeloid diseases, particularly myelodysplastic syndromes and acute myeloid leukemia (Dubourg et al. 2002; Guenet et al. 2000). Eukaryotic RF1 has also been identified as a component of Hedgehog signaling (Collins et al. 2005). Hedgehog proteins provide positional information during the development of many different morphological structures, including the forebrain, neural tube, eyes, and limbs. Deregulation of Hedgehog signaling has been correlated with numerous cancers including basal cell carcinomas, gliomas, and gastric and prostate cancers (Collins et al. 2005).

The histone deacetylase inhibitor sodium butyrate down-regulates transcriptional levels of the mRNA encoding eRF1 and this has been proposed as part of the mechanism leading to cell-cycle arrest and apoptosis in breast cancer cell lines (Goncalves et al. 2005). In addition to its role in translation termination, eRF3 has also been shown to function in cell-cycle regulation, cytoskeleton organization, and apoptosis. Deregulation of eRF3 levels and activities have been correlated with gastric cancers. Overexpression of eRF3 in gastric tumors may directly lead to increased translation efficiency, and overexpression, of specific oncogenic mRNA transcripts (Malta-Vacas et al. 2005. Likewise, polyglycine expansions of eRF3 have been associated with susceptibility to gastric cancer and, although it is possible that this mutation of eRF3 may affect its functional role in the other cellular processes in which it participates, it is likely that at least part of the effects of these polyglycine expansions are related to eRF3's functional role in translation termination (Brito et al. 2005).

Nonsense-Mediated Decay

In eukaryotes, another essential regulatory pathway resulting from inefficient termination at unnatural stop codon contexts is the process of nonsense-mediated mRNA decay (NMD). NMD is an mRNA quality control mechanism that efficiently and rapidly targets mRNAs containing premature termination codons (PTCs) for degradation. NMD effectively post-transcriptionally regulates gene expression by removing defective mRNAs from the cell prior to translation (Chang et al. 2007). PTCs arise from random nonsense or frameshift mutations in genomic DNA, programmed DNA rearrangements, or errors in mRNA splicing (Chang et al. 2007). Bioinformatic approaches have predicted that approximately 35% of all human genetic disorders and many forms of cancer (Frischmeyer et al. 1999).

In one aspect, the invention described herein provides methods for developing therapeutic compounds to control regulation at the translational level by manipulation of the protein synthesis center of the cell.

When healthy cells transform into cancerous cells, regulation of the translation process is altered and reprogrammed such that the identities and amounts of proteins synthesized by the ribosome change dramatically. Deregulation of the termination process in human cells has been correlated with malignant myeloid diseases, particularly myelodysplastic syndromes and acute myeloid leukemia, as well as with basal cell carcinomas, gliomas, and gastric, prostate, and breast cancers. Experimental methods combining inhibition of the NMD pathway with DNA microarray technology have revealed numerous examples of different tumor suppressor genes containing PTCs in prostate, colon, breast, and ovarian cancer cell lines (Anczukow et al. 2007; Ivanov et al. 2007; Ware et al. 2006; Rossi et al. 2005; Wolf et al. 2005; Ionov et al. 2004). Particular cancers in which PTC mutations have been shown to play an important role include the BRCA1 and BRCA2 breast cancer susceptibility genes. The large majority of deleterious mutations in BRCA2 introduce a PTC into the open reading frame (see Breast Cancer Information Core database) (Ware et al. 2006); these mRNAs are then believed to be targeted by the NMD pathway.

The first step in triggering NMD involves the recognition of a premature stop codon, a process that involves eRF1 (Chang et al. 2007). The ribosome and/or eRF1 may distinguish premature from natural stop codons by their codon context (e.g. by detecting nucleotides located downstream and upstream from the stop codon) (Chabelskaya et al. 2007; Ware et al. 2006 Keeling et al. 2002).

Small molecule aminoglycoside antibiotics of the neomycin class, which specifically bind the ribosome at the 30S decoding center (Ogle et al. 2001; Fourmy et al. 1996), have been shown to effectively inhibit termination specifically at PTCs in a codon context-dependent manner (Howard et al. 2000). The ribosomal DC and/or eRF1 act to distinguish premature from normal stop codons using their codon context and demonstrate the potential for selectively targeting this phenomenon with small molecule drugs (Keeling et al. 2002). Human clinical trials have demonstrated the effectiveness of the aminoglycoside gentamycin in treatment of two classic PTC diseases: Duchenne muscular dystrophy and nonsense mutation-mediated cystic fibrosis, diseases caused by mutations yielding PTCs within the dystrophin and cystic fibrosis transmembrane conductance regulator (CFTR) genes, respectively (Politano et al. 2003; Wilschanski et al. 2003; Clancy et al. 2001; Wagner et al. 2001; Barton-Davis et al. 1999).

PTC124, a nonaminoglycoside, acts analogously to gentamycin, selectively promoting readthrough of PTCs in a stop codon context-dependent manner. PTC124 is also being used to treat Duchenne muscular dystrophy and nonsense mutation-mediated cystic fibrosis (Du et al. 2008; Welch et al. 2007). Both gentamycin and PTC124 protect the PTC-containing dystrophin and CFTR mRNAs from NMD and rescue production of dystrophin and CFTR in mice models and in humans, demonstrating that these drugs act by specifically targeting the NMD pathway (Linde et al. 2007; Welch et al. 2007). If they can be properly targeted to malignant cells, compounds like PTC124 or gentamycin could potentially be used to promote stop-codon readthrough of PTC mutations in tumor suppressor genes where this type of mutation is prevalent, for example BRCA2.

In one aspect, the methods described herein can be used for selective manipulation of the NMD pathway and the development of new anti-cancer agents that target this novel pathway.

FRET

The methods described herein are suitable for measuring structural changes in macromolecular complexes using Förster (or fluorescence) resonance energy transfer (FRET). FRET is a physical process whereby energy is transferred non-radiatively from an excited donor fluorophore to an acceptor, which may be another fluorophore, through intramolecular long-range dipole-dipole coupling. One factor to consider in choosing the donor fluorophore/acceptor pair is the efficiency of FRET between the donor fluorophore and acceptor. The efficiency of FRET is dependent on the separation distance and the orientation of the donor fluorophore and acceptor as described by the Förster equation, as well as the fluorescent quantum yield of the donor fluorophore and the energetic overlap with the acceptor. In particular, the efficiency (E) of FRET can be determined as follows:

$$E = 1 - F_{DA}/F_D = 1/(1+(R/R_o)^6)$$

where $F_{DA}$ and $F_D$ are the fluorescence intensities of the donor fluorophore in the presence and absence of the acceptor, respectively, and R is the distance between the donor fluorophore and the acceptor.

The Förster radius ($R_o$) is the distance at which resonance energy transfer is 50% efficient, that is, 50% of excited donor fluorophores are deactivated by FRET. The magnitude of the Förster radius depends on the quantum yield of the donor fluorophore, the extinction coefficient of the acceptor, and the overlap between the donor fluorophore's emission spectrum and the acceptor's excitation spectrum. For effective transfer, the donor fluorophore and acceptor are in close proximity, separated, for example, by about 10 Å to about 100 Å. For effective transfer over 10 Å to 100 Å, the quantum yield of the donor fluorophore generally is at least 0.1, and the absorption coefficient of the acceptor generally is at least 1000 (see Clegg, Current Opinion in Biotech. 6:103-110 (1995); and Selvin, Nature Structural Biol. 7:730-734 (2000)). Typical Förster radius values for various donor fluorophore/acceptor pairs are known in the art (see, also, Wu and Brand, Analytical Biochem. 218:1-13 (1994)). Comprehensive lists of Förster radii also are also known in the art (see, for example, Berlman, Energy Transfer Parameters of Aromatic Compounds Academic Press, New York 1973). Furthermore, those skilled in the art recognize that component factors of the Förster radius ($R_o$) are dependent upon the environment such that the actual value observed can vary from the listed value.

The donor fluorophore and acceptor are selected so that the donor fluorophore and acceptor exhibit resonance energy transfer when the donor fluorophore is excited. Effective energy transfer is dependent on the spectral characteristics of the donor fluorophore and acceptor, as well as their relative orientation. A donor fluorophore generally can be selected such that there is substantial spectral overlap between the emission spectrum of the donor fluorophore and the excitation spectrum of the acceptor. In addition, a donor fluorophore can be selected, for example, to have an excitation maximum near a convenient laser frequency such as Helium-Cadmium 442 nm or argon 488 nm, since laser light serves as a convenient and effective means to excite the donor fluorophore.

Separated emission maxima allow altered acceptor emission to be detected without donor emission contamination. The wavelength maximum of the emission spectrum of the acceptor moiety is preferably at least 10 nm greater than the wavelength maximum of the excitation spectrum of the donor fluorophore. In particular examples, the acceptor is a fluorophore having an emission spectrum in the red portion of the visible spectrum, or in the infrared region of the spectrum.

A variety of donor fluorophore-acceptor pairs, and their Förster radii are known in the art and listed in Table 1. (See also, Haugland, Handbook of Fluorescent Probes and Research Chemicals 6th Edition, Molecular Probes, Inc., Eugene, Oreg. 1996.)

TABLE 1

Exemplary Donor Fluorophores and Acceptors

| Donor fluorophore | Acceptor | Ro (DELTA) | Reference |
|---|---|---|---|
| Fluorescein | TMR | 49-54 | Johnson et al.,*Biochemistry* 32: 6402-6410 (1993); Odom et al., *Biochemistry* 23: 5069-5076 (1984) |
| Fluorescein | QSY ®7 | 61 | — |
| EDANS | DABCYL | 33 | — |
| Napthalene | Dansyl | 22 | Haas et al., *Proc. Natl. Acad. Sci.* USA 72: 1807-1811 (1975) |
| IANBD | DDPM | 25 | Kasprzyk et al.,*Biochemistry* 22: 1877-1882 (1983) |
| IAEDANS | DDPM | 25-29 | Dalbey et al., *Biochemistry* 22: 4696-4706 (1983); Cheung et al.,*Biophys. Chem.* 40: 1-17 (1991) |
| DNSM | LY | 26-32 | Nalin et al., *Biochemistry* 28: 2318-2324 (1985) |
| IAEDANS | IANBD | 27-51 | Franzen et al., *Biochemistry* 19: 6080-6089 (1980); First et al.,*Biochemistry* 28: 3606-3613(1989) |
| ε-A | F2DNB | 29 | Perkins et al.,*J. Biol. Chem.* 259: 8786-8793 (1984) Pyrene Bimane 30 Borochov-Neori and Montal,*Biochemistry* 28: 1711-1718 (1989) |
| ANAI | IPM | 30 | Peerce and Wright,*Proc. Natl. Acad. Sci.* USA 83: 8092-8096 (1986) |
| IAANS | IAF | 31 | Grossman, *Biochim. Biophys. Acta* 1040: 276-280 (1990) |
| ε-A | F$_2$DPS | 31 | Perkins et al., supra, 1984 |
| ε-A | DDPM | 31 | Miki and Mihashi, *Biochim. Biophys. Acta* 533: 163-172 (1978) |
| IAEDANS | TNP | 31-40 | Takashi et al., *Biochemistry* 21: 5661-5668 (1982); dos Remedios and Cooke, *Biochim. Biophys. Acta* 788: 193-205 (1984) |
| MNA | DACM | 32 | Amir and Haas,*Biochemistry* 26: 2162-2175 (1987) |
| PM | NBD | 32 | Snyder and Hammes,*Biochemistry* 24: 2324-2331 (1985) |
| FITC | TNP-ATP | 32 | Amler et al.,*Biophys. J.* 61: 553-568 (1992) |
| DANZ | DABM | 34 | Albaugh and Steiner,*J. Phys. Chem.* 93: 8013-8016 (1989) |
| NCP | CPM | 34 | Mitra and Hammes,*Biochemistry* 28: 3063-3069 (1989) |
| NAA | DNP | 33-37 | McWherter et al.,*Biochemistry* 25: 1951-1963 (1986) |
| LY | TNP-ATP | 35 | Nalin, supra, 1985 |
| IAF | diI-C$_{18}$ | 35 | Shahrokh et al.,*J. Biol. Chem.* 266: 12082-12089 (1991) |
| IAF | TMR | 37 | Taylor et al., *J. Cell Biol.* 89: 362-367 (1981) |
| FMA | FMA | 37 | Dissing et al.,*Biochim. Biophys. Acta* 553: 66-83 (1979) |
| PM | DMAMS | 38 | Lin and Dowben, *J. Biol. Chem.* 258: 5142-5150 (1983) |
| mBBR | FITC | 38 | Tompa and Batke,*Biochem. Int.* 20: 487-494 (1990) |
| mBBR | DABM | 38 | Kasprzak et al.,*Biochemistry* 27: 4512-4523 (1988) |
| ε-A | NBD | 38 | Miki and Iio,*Biochim. Biophys. Acta* 790: 201-207 (1984) |
| Pyrene | Coumarin | 39 | Borochov-Neori and Montal, supra, 1989 |
| IPM | FNAI | 39 | Peerce and Wright, supra, 1986 |
| IAEDANS | DABM | 40 | Tao et al.*Biochemistry* 22: 3059-3066 (1983) |
| IAEDANS | TNP-ATP | 40 | Tao et al., supra, 1983 |
| ε-A | IANBD | 40 | Miki and Wahl,*Biochim. Biophys. Acta* 786: 188-196 (1984) |
| NBD | SRH | 40-74 | Wolf et al.,*Biochemistry* 31: 2865-2873 (1992) |
| ISA | TNP | 42 | Jacobson and Colman,*Biochemistry* 23: 3789-3799 (1984) |
| Dansyl | ODR | 43 | Lu et al.,*J. Biol. Chem.* 264: 12956-12962 (1989) |
| DANZ | IAF | 44-49 | Cheung et al.,*Biochemistry* 21: 5135-5142 (1983) |

TABLE 1-continued

Exemplary Donor Fluorophores and Acceptors

| Donor fluorophore | Acceptor | Ro (DELTA) | Reference |
|---|---|---|---|
| FNAI | EITC | 45 | Peerce and Wright, supra, 1986 |
| NBD | LRH | 45-70 | Wolf et al., supra, 1992 |
| IAF | EIA | 46 | Taylor et al., supra, 1981 |
| FITC | ENAI | 46 | Peerce and Wright, supra, 1986 |
| Proflavin | ETSC | 46 | Robbins et al., *Biochemistry* 20: 5301-5309 (1981) |
| CPM | TNP-ATP | 46 | Snyder and Hammes, supra, 1985 |
| IAEDANS | IAF | 46-56 | Franzen, supra, 1985; Grossman, supra, 1990 |
| CPM | Fluorescein | 47 | Thielen et al., *Biochemistry* 23: 6668-6674 (1984) |
| IAEDANS | FITC | 49 | Jona et al., *Biochim. Biophys. Acta* 1028: 183-199 (1990); Birmachu et al., *Biochemistry* 28: 3940-3947 (1989) |
| IAF | TMR | 50 | Shahrokh et al., *J. Biol. Chem.* 266: 12082-12089 (1991) |
| CF | TR | 51 | Johnson et al., supra, 1993 CPM TRS 51 Odom et al., supra, 1984 |
| ε-A | TNP-ATP | 51 | dos Remedios and Cooke, supra, 1984 |
| CPM | FM | 52 | Odom et al., supra, 1984 |
| LY | EM | 53 | Shapiro et al., *J. Biol. Chem.* 266: 17276-17285 (1991) |
| FITC | EITC | 54 | Carraway et al., *J. Biol. Chem.* 264: 8699-8707 (1989) |
| IAEDANS | DiO-$C_{14}$ | 57 | Shahrokh et al., supra, 1991 |
| IAF | ErITC | 58 | Amler et al., supra, 1992 |
| FITC | EM | 60 | Kosk-Kosicka et al., *J. Biol. Chem.* 264: 19495-19499 (1989) |
| FITC | ETSC | 61-64 | Robbins et al., supra, 1981 |
| FITC | ErITC | 62 | Amler et al., supra, 1992 |
| BPE | CY5 | 72 | Ozinskas et al., *Anal. Biochem.* 213: 264-270 (1993) |
| Fluorescein | Fluorescein | 44 | — |
| BODIBY FL .RTM. | BODIPY FL .RTM. | 57 | — |

ANAI: 2-anthracence N-acetylimidazole;
BPE: B-phycoerythrin;
CF: carboxyfluorescein succinimidyl ester;
CPM: 7-diethylamino-3-(4'-maleimidylphenyl)-4-methylcoumarin;
CY5: carboxymethylindocyanine-N-hydroxysuccinimidyl ester;
diI-$C_{18}$: 1,1'-dioctadecyl-3-3,3,3',3'-tetramethyl-indocarbocyanine;
diO-$C_{14}$: 3,3'-ditetradecyloxacarbocyanine;
DABM: 4-dimethylaminophenylazo-phenyl-4'-maleimide;
DACM: (7-(dimethylamino)coumarin-4-yl)-acetyl;
DANZ: dansylaziridine;
DDPM: N-(4-dimethylamino-3,5-dinitrophenyl)maleimide;
DMAMS: dimethylamino-4-maleimidostilbene;
DSMN: N-(2,5'-dimethoxystiben-4-yl)-maleimide;
DNP: 2,4-dinitrophneyl;
ε-A: 1,N.sup.6-ethenoadenosine;
EIA: 5-(iodoacetamido)eosin;
EITC: eosin-5-isothiocyanate;
ENAI: eosin N-acETYLIMIDAZOLE;
EM: eosin maleimide;
ErITC: erythrosin-5'-isothiocyanate;
ETSC: eosin thiosemicarazide;
$F_2DNB$: 1,5-difluro-2,4'-dinitrobenzene;
$F_2DPS$: 4,4'-difluoro-3,3'-dinitrophenylsulfone;
FITC: fluorescein thiosemicarbazide;
IAANS: 2-(4'-iodoacetamido)anilino)napthalene-6-sulfonic acid;
IAEDANS: 5-(2-((iodoacetyl)amino)ethyl)amino)-napthlene-1-sulfonic acid;
IAF: 5-iodoacetamidofluorescein;
IANBD: N-((2-(iodoacetoxy)ethyl)-N-methyl)amino-7-nitrobenz-2-oxa-1,3-diaz-ole;
IPM: 3(4-isothiocyanatophenyl)7-diethyl-4-amino-4-methylcoumarin;
ISA: 4-(iodoacetamido)salicylic acid;
LRH: lissaminerhodamine;
LY: Lucifer yellow;
mBBR: monobromobiamane; MNA, (2-methoxy-1-naphthyl)-methyl;
NAA: 2-napthoxyacetic acid;
NBD: 7-nitro-2,1,3-benzoxadiazol-4-yl;
NCP: N-cyclohexyl-N'-(1-pyrenyl)carbodiimide; PM, N-(1-pyrene)-maleimide;
ODR: octadecylrhodamine;
SRH: sulforhodamine;
TMR: tetramethylrhodamine;
TNP: trinitrophenyl; and
TR: Texas Red In other examples, the donor fluorophore can be fluorescein in combination with rhodamine; texas red; eosin; ROX (6-carboxy-X-rhodamine; Applied Biosystems Division of Perkin-Elmer Corporation; Foster City, Calif.); or TAMRA (N,N,N',N'-tetramethyl-6-carboxy-rhodamine; Applied Biosystems). In other examples, the donor fluorophore is cascade blue with fluorescein as an acceptor; the donor fluorophore is BODIPY® 530/550 (4,4-difluoro-5,7-diphenyl-4-bora-3a,4a-diaza-5-indacene) in combination with BODIPY® 542/563 (4,4-difluoro-5-p-methoxyphenyl-4-bora-3a,4a-diaza-5-indacene) as an acceptor; or the donor fluorophore is BODIPY® 542/563 in combination with BODIPY® 564/570 (4,4-difluoro-5-styryl-4-bora-3a,4a-diaza-5-indacene) as an acceptor. It is understood that the numbers following the name reflect the excitation and emission maxima of the molecule; BODIPY® compounds are commercially available from Molecular Probes (Eugene, Oreg.).

Detection of Ribosomal Dynamics

Comparisons of X-ray crystallographic and cryogenic electron microscopic structures of ribosomal complexes have show that conformational dynamics of the ribosome, its transfer RNA (tRNA) substrates, and associated translation factors play important mechanistic and regulatory roles throughout all stages of protein synthesis.

Structural changes of the translational machinery can be directly characterized using fluorescently-labeled components within a highly-purified in vitro translation system in real time using smFRET in order to elucidate the mechanisms through which these dynamics direct and regulate the individual steps of translation. New ribosome-ribosome, ribosome-tRNA, and tRNA-translation factor smFRET signals can be used to characterize the intrinsic conformational dynamics of a ribosomal domain, the L1 stalk, as well as the coupling between L1 stalk and tRNA dynamics, throughout protein synthesis. This analysis shows that the translating ribosome can spontaneously and reversibly fluctuate between two global conformational states, and that transitions between these two states involve coupled movements of the L1 stalk and ribosome-bound tRNAs, accompanied by ratcheting of the ribosomal subunits. Furthermore, elongation, release, and ribosome recycling factors recognize these global states of the ribosome and differentially affect transition rates between the two states. Thus, translation factor mediated recognition and control over intrinsic dynamics of the ribosome plays a major mechanistic role during the elongation, termination, and recycling stages of translation. Specific regulation of the global state of the ribosome is a fundamental characteristic of all translation factors and a unifying theme throughout protein synthesis.

FRET signals between fluorescently-labeled class 1 RF and various functional moieties on the ribosome can be measured to detect a structural change in the macromolecular complex. Functional moieties suitable for measuring a FRET signal with fluorescently-labeled class 1 RF include messenger RNA, transfer RNA substrates, and ribosomal proteins. In one embodiment, the invention relies on a tRNA, an rRNA, an mRNA, or a ribosomal protein in which, under optimal conditions, the efficiency of FRET between the donor fluorophore and acceptor is at least 10%, at least 20%, at least 30%, at least 40%, at least 50%, at least 60%, at least 70% or at least 80%.

A "shift in FRET efficiency" occurs when the FRET efficiency has increased or decreased by about 40% or 0.4. A "loss in FRET efficiency" is a shift in FRET efficiency from a measurable value to essentially no measurable value over background. A "lack of FRET efficiency" is no measurable value over background. "High FRET efficiency" is at least about 60% or 0.6, preferably at least about 70% or 0.7, and more preferably at least about 80% or 0.8. "Low FRET efficiency" is less than about 30% or 0.3, preferably less than about 20% or 0.2.

Labeling Strategies

Any of a number of donor fluorophores and acceptors in various combinations can be used. In one embodiment, the donor-acceptor pair can be located on the same tRNA, rRNA, mRNA, or ribosomal protein such that a conformational change in the tRNA, rRNA, mRNA, or ribosomal protein can be detected as a change in a FRET signal. In another embodiment, the donor-acceptor pair can be located on different RNA molecules or ribosomal proteins such that a the proximity of one to another can be detected as a change in a FRET signal.

One skilled in the art understands that there are several considerations in selecting and positioning a donor and an acceptor fluorophoreon a tRNA, an rRNA, an mRNA, or a ribosomal protein. The fluorophores should be positioned to minimize interference with the activity of the labeled molecule, and to minimize interference with the ability of the labeled molecule to form a complex with another tRNA, rRNA, mRNA, or ribosomal protein. Thus, fluorophores can be selected and positioned, for example, so as to minimize the disruption of bonded and non-bonded interactions that are important for binding, and to minimize steric hindrance. In addition, the spatial distance between the acceptor and donor fluorophore generally can be limited to achieve efficient energy transfer from the donor fluorophore to the acceptor.

A tRNA, rRNA, mRNA, or ribosomal protein can be designed to optimize the efficiency of FRET, as well as the protein or RNA activity. A donor fluorophore can be selected, if desired, with a high quantum yield, and an acceptor can be selected, if desired, with a high extinction coefficient to maximize the Förster distance. Fluorescence arising from direct excitation of an acceptor can be difficult to distinguish from fluorescence resulting from resonance energy transfer. Thus, it is recognized that a donor fluorophore and acceptor can be selected which have relatively little overlap of their excitation spectra such that the donor can be excited at a wavelength that does not result in direct excitation of the acceptor. Labeled molecules can be designed so that the emission spectra of the donor and acceptor overlap relatively little, such that the two emissions can be readily distinguished.

In addition to a donor and acceptor, a ribosomal protein useful in the invention optionally can include one or more additional components. As an example, a flexible spacer sequence, for example GSGGS (SEQ ID NO: 1), can be included in a ribosomal protein. A ribosomal protein further can include one or more of an affinity tag such as HIS6(SEQ ID NO: 9), biotin, or an epitope such as FLAG, hemaglutinin (HA), c-myc, or AU1; an immunoglobulin hinge region; an N-hydroxysuccinimide linker; a peptide or peptidomimetic hairpin turn; a hydrophilic sequence, or another component or sequence that promotes the solubility or stability of the ribosomal protein.

Sequence similarity or structural similarity can also be used identify a site suitable for labeling tRNA, rRNA, mRNA, or ribosomal protein of the invention. For example, E. coli RF1 can be used as a model for eRF1 due to the highly-conserved nature of the protein synthetic apparatus throughout evolutionary history because the mechanism of action of RF1 in E. coli is evolutionarily conserved from bacteria through humans.

Specific sites of interest for labeling include tRNA, which may be labeled on the RNA or the amino acid portion of the molecule. Body labeling of the RNA itself can be accomplished, for example by synthesizing the tRNA with an amino linker, which can be derivatized. Suitable sites include the anticodon stem loop, the elbow region and 3' acceptor arm. Alternatively, the amino acids used to charge the tRNA can be labeled and then used to charge the tRNA with the appropriate aminoacyl synthetase.

Direct fluorescent labeling of ribosomal RNA can utilize a complementary polynucleotide probe that is complementary to a target sequence, where a labeled polynucleotide specifically hybridizes to a rRNA sequence. Target sites on the rRNA for hybridization include regions of conserved A-form helical secondary structure where the primary sequence of the helical region is not evolutionarily conserved. Examples include surface-accessible hairpin loops, particularly those regions that are not involved in tertiary structure formation. Such regions may be identified by a comparison of rRNA sequences to determine a lack of sequence similarity. Criteria include a helix of at least about 5 nt. in length, with a non-conserved nucleotide sequence.

The native sequence may serve as a target site, or more preferably, the rRNA will be genetically modified to expand stem loop sequences by from about 6 to about 20 nucleotides, more usually from about 8 to about 18 nucleotides. Preferred rRNA suitable for such modification is the prokaryotic 16S rRNA or the corresponding eukaryotic 18S rRNA, although the 23S and 28S rRNA may also find use. Specific sites of interest for the introduction of a stem loop expansion for an attachment site include, without limitation, the 16S rRNA H6, H10, H16, H17, H26, H33a, H33b, H39 and H44 loops. In 23S rRNA, the H9, H38, H68 H69, H72, H84, H89, H91 and H101 may be selected.

Alternatively ribosomes may be labeled using a peptide tagging strategy. The BIV Tat protein binds to a specific sequence in the context of an A-form helix with a single-nucleotide bulge; the peptide binds with high affinity (Kd nM) and specificity within the major groove of the helix. See, for example, Campisi et al. (2001) EMBO J. 20(1-2): 178-86. Target sites, as described above for hybridization labels, can be genetically modified to contain a BIV Tat binding site, to which is bound fluorescently labeled BIV Tat. The recognition sequence for BIV Tat is 5' NUGNGC 3'(SEQ ID NO: 2); 5' GCNCN 3' (SEQ ID NO: 10), where the two strands pair to form a quasi A form paired helix with a single bulged uridine; and where the N-N pair must be a Watson-Crick pair for stability. The BIV Tat peptide generally comprises the amino acid sequence RGTRGKGRRI (SEQ ID NO: 3) for high binding affinity. An alternate peptide tag is the HIV Rev peptide, which binds to a purine-rich internal loop in an RNA helix. For double labeling of different subunits, the individual subunits can separated and labeled independently, using combinations of one or more peptide and/or hybridization tags.

Labeled peptide or polynucleotide probes can be synthesized and derivatized with a fluorescent tag. The labeled probes can then be incorporated into cell growth media, or bound to the ribosomes post-synthetically. When bound to the ribosome during synthesis the probes further provide a means investigating the in vivo process of ribosome assembly.

Another approach for rRNA labeling utilizes internal incorporation of dyes by ligation of 16S rRNA fragments that contain dyes at their 5' or 3' termini. For example, 16S rRNA can be transcribed as two pieces, with a dye-labeled dinucleotide as primer of transcription. The two strands are then ligated by DNA ligase and a DNA splint. The 30S subunit is then reconstituted from total 30S proteins using standard protocols.

In another embodiment, the mRNA is labeled. For example, a labeled oligonucleotide may be hybridized downstream on the mRNA of choice, and the hybridized mRNA then combined with a surface bound ribosome complex, where the ribosome complex comprises a label that is a complementary donor/acceptor to the oligonucleotide label. Translation elongation can measured by the interaction of the mRNA with a labeled ribosome. The dye label on the ribosome can be attached to the 30S subunit, near where the 3' end of the mRNA exits from the ribosome, e.g. the cleft near ribosomal protein S5 is the leading edge of the translating ribosome. An alternate labeling approach utilizes reconstituted 30S particles with labeled S5 protein; a number of single-cysteine mutants of S5 have been derivatized and successfully incorporated into 30S subunits.

In another embodiment, labeled DNA oligonucleotides of from about 6 to about 20, usually about 8 to 10 nucleotides are pre-hybridized to mRNA in the test sample, where the site for hybridization is downstream from the initiation codon. Similarly, two labeled oligonucleotides that each comprise one member of a donor acceptor fluorochrome pair may be hybridized successively downstream of the start codon. Alternatively, a labeled oligonucleotide is designed to be complementary to the region of mRNA occluded by the ribosome in the initiation complex.

An alternative method utilizes mRNA that comprises an epitope for which a high affinity antibody is available. Numerous such epitopes are known in the art, e.g. the sequence encoding the amino acid EQKLISEEDL (SEQ ID NO: 4), which is the epitope for high-affinity binding by anti-myc antibody. The epitope will be exposed to the antibody upon its emersion from the 50S subunit exit tunnel, which protects about 40-50 amino acids. Binding of labeled antibody will lead to localization of the label, which means at least about 40-50 amino acids have been synthesized. The epitope tag can be incorporated into any coding sequence of interest, and may be positioned at varying sites throughout the coding sequence. From the time lag before localization of fluorescence as a function of tag position, translation rates can be estimated. As an alternative to an epitope tag, peptide sequences that form fluorescent arsenate complexes can be inserted into the coding sequence. Translation of such modified mRNA is performed in the presence of the labeling arsenic compound.

Many proteins involved in the process of translation can be labeled, including ribosomal proteins, elongation and initiation factors, and the like. For example, the S21 protein sits in the tRNA exit site of the ribosome (E site), and can be dye labeled by any conventional method. The labeled protein is separated from the unbound dye, and then incubated with the suitable ribosomal subunit at a molar excess of protein to favor exchange of the native protein with the labeled protein.

Site Specific Labeling of Ribosomal Proteins

Binding and function of class 1 RF throughout a ribosomal termination reaction can be observed using fluorescently-labeled RFs within a protein synthesis system. Any protein synthesis system known in the art can be used to produce an class 1 RF protein. In one embodiment, the protein synthesis system is a purified *E. coli* protein synthesis system. In another aspect, the methods described herein relate to site-specific labeling of proteins. For example, *Escherichia coli* RF1 protein can be labeled at a number of unique positions with fluorescent probes. Standard biochemical assays can be used to demonstrate that these fluorescently-labeled RF1s retain their full biochemical activity relative to the wild type RFs.

Specific residues on a ribosomal protein, which can be mutated to allow site specific labeling of the protein without significantly altering its function in the ribosomal complex or in isolation, can be identified. For example, fluorophores can be conjugated to a class 1 RF such that the class 1 RF will exhibit characteristic photophysical changes upon ribosome binding and provide an observable output suitable for assaying the function of class 1 RF in biochemical experiments. In one embodiment, a fluorophore-labeled class 1 RF protein can be used to measure conformational changes of the class 1 RF which accompany its binding to the ribosome complex. In another embodiment, a fluorophore labeled class 1 RF protein can be used to measure conformational changes of class 1 RF during hydrolysis of the polypeptide product of protein synthesis.

Methods for conjugating proteins, peptides and peptidomimetics to a fluorophore or acceptor are well known in the art (Fairclough and Cantor, Methods Enzymol. 48:347-379 (1978); Glaser et al., Chemical Modification of Proteins Elsevier Biochemical Press, Amsterdam (1975); Haugland, Excited States of Biopolymers (Steiner Ed.) pp. 29-58, Plenum Press, New York (1983); Means and Feeney, Bioconjugate Chem. 1:2-12 (1990); Matthews et al., Methods Enzymol. 208:468-496 (1991); Lundblad, Chemical Reagents for Protein Modification 2nd Ed., CRC Press, Boca Ratan, Fla. (1991); Haugland, supra, 1996). A variety of groups can be used to couple a donor fluorophore or acceptor, for example, to a tRNA, rRNA, mRNA, or ribosomal protein. A thiol group, for example, can be used to couple a donor fluorophore or acceptor to the desired position in a tRNA, rRNA, mRNA, or ribosomal protein useful in the methods of the invention. Haloacetyl and maleimide labeling reagents also can be used to couple donor fluorophores or acceptors in preparing a tRNA, rRNA, mRNA, or ribosomal protein useful in the invention (see, for example, Wu and Brand, supra, 1994).

Single Molecule Measurements

The methods of the invention can be used to monitor binding and activity of class 1 RF at the single-molecule level. In one embodiment, single molecule measurements can be obtained using a combination of a surface-immobilized protein synthesis system with total internal reflection fluorescence microscopy. Therefore, where the fluorescently labeled molecule is immobilized either directly or indirectly, FRET efficiency is measured by imaging the solid surface. Alternatively, FRET efficiency can be measured where a fluorescently labeled molecule is not bound to a solid surface using, for example, confocal microscopy. In such instance, FRET efficiency is measured by imaging the reaction mixture, rather than the molecules bound to the solid surface.

Traditional bulk enzymology reports the average values of biochemical parameters. Single-molecule studies complement ensemble measurements by defining the ensemble itself, and can revealing heterogeneity in the behavior of individual molecules (English et al. 2006). Examination of individual reaction trajectories therefore eliminates the problem of population averaging associated with the asynchrony inherent in ensemble studies. Such asynchrony can obscure the existence of important, but short-lived or rare intermediates.

Single-molecule FRET combines the ability to monitor individual reaction trajectories with an observable signal that is exquisitely sensitive to conformational change. Measurement of smFRET efficiency via the dipolar coupling of a donor and acceptor fluorophore pair depends on the distance separating the two fluorophores (assuming both fluorophores are freely rotating and isotropically oriented during the excited state lifetime). Therefore, as described above, smFRET efficiency can be used to measure conformational changes by using the relationship $$E=1/[1+(R/Ro)6]$$

where E is the FRET efficiency, R is the distance between the donor and acceptor fluorophores, and Ro is the Förster distance (the separation distance for a specific donor-acceptor pair that yields a 50%, or 0.5, FRET efficiency). The Cy3 (donor) and Cy5 (acceptor) fluorophores used in the Examples have an Ro of 50 Å and are therefore sensitive to conformational changes within a distance range of 30-80 Å.

Amino Acid Modifications

According to certain embodiments of the invention, ribosomal proteins can be modified such that the activity of the protein is retained. In other embodiments, ribosomal proteins can be modified such the ability of the protein to enter into a complex with one or more proteins or nucleic acids is retained. Single or multiple amino acid substitutions (in certain embodiments, conservative amino acid substitutions) can be made in a naturally-occurring sequence (in certain embodiments, in the portion of the polypeptide outside the domain(s) forming intermolecular contacts). In certain embodiments, a conservative amino acid substitution may not substantially change the structural characteristics of the reference sequence (e.g., in certain embodiments, a replacement amino acid should not tend to break a helix that occurs in the reference sequence, or disrupt other types of secondary structure that characterizes the reference sequence). Examples of certain art-recognized polypeptide secondary and tertiary structures are described, for example, in Proteins, Structures and Molecular Principles (Creighton, Ed., W.H. Freeman and Company, New York (1984)); Introduction to Protein Structure (C. Branden and J. Tooze, eds., Garland Publishing, New York, N.Y. (1991)); and Thornton, J. M. et al. (1991) Nature 354:105-106.

In one embodiment, a amino acid substitution as described herein can be a conservative amino acid substitution. A conservative amino acid substitution refers to the substitution of an amino acid in a polypeptide with another amino acid having similar properties, such as size or charge. In certain embodiments, a polypeptide comprising a conservative amino acid substitution maintains at least one activity of the unsubstituted polypeptide. A conservative amino acid substitution can encompass non-naturally occurring amino acid residues, which are typically incorporated by chemical peptide synthesis rather than by synthesis in biological systems. These include, but are not limited to, peptidomimetics and other reversed or inverted forms of amino acid moieties.

Amino acids can be classified on the basis of similarity in polarity, charge, solubility, hydrophobicity, hydrophilicity, and/or the amphipathic nature of the residues (Table 2). Negatively charged amino acids include aspartic acid and glutamic acid; positively charged amino acids include lysine and arginine.

TABLE 2

| Amino Acid Classification | | |
|---|---|---|
| Aliphatic | Non-polar | Gly Ala Pro Ile Leu Val |
| | Polar, uncharged | Cys Ser Thr Met Asn Gln |
| | Polar, charged | Asp Glu Lys Arg |
| Aromatic | | His Phe Trp Tyr |

The amino acid sequences of cellular translational machinery are heavily conserved across species. It is possible, for example, to align all bacterial RF1 sequences and identify amino acid positions that are not identical among different bacterial species. These amino acids are "phylogenetically variable."

An amino acid position can be characterized as having low phylogenetic variability when amino acids at that position across species are selected from those within the same line in column 3 of Table 2. For example, in a comparison of a protein sequence from five different organisms, if the amino acids at position 20 for each of the five sequences were Ile, Ile, Val, Leu, Val, position 20 would have low phylogenetic variability.

An amino acid position can be characterized as having high phylogenetic variability when amino acids at that position are selected from those within different blocks in column 3 of Table 2. For example, in a comparison of a protein sequence from five different organisms, if the amino acids at position 20 for each of the five sequences were Arg, Gly, Val, Lys, Lys, position 20 would have high phylogenetic variability.

Non-conservative substitutions can involve the exchange of a member of one of these classes for a member from another class. Such substituted residues can be introduced into regions of a ribosomal protein that are homologous with non-human ribosomal proteins, or into the non-homologous regions of the molecule.

In making substitutions, according to certain embodiments, the hydropathic index of amino acids can be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). The importance of the hydropathic amino acid index in conferring interactive biological function on a protein, in certain instances, is understood in the art. Kyte et al., J. Mol. Biol., 157:105-131 (1982). It is known that in certain instances, certain amino acids can be substituted for other amino acids having a similar hydropathic index or score and still retain a similar biological activity. See Table 3.

TABLE 3

| Exemplary amino acid substitutions | |
|---|---|
| Ala | Val, Leu, Ile |
| Arg | Lys, Gln, Asn |
| Asn | Gln |
| Asp | Glu |
| Cys | Ser, Ala |
| Gln | Asn |
| Gly | Asp |
| His | Asn, Gln, Lys, Arg |
| Ile | Leu, Val, Met, Ala, Phe, Norleucine |
| Lys | Arg, 1,4 Diaminobutyric Acid, Gln, Asn |
| Met | Leu, Phe, Ile |
| Phe | Leu, Val, Ile, Ala, Tyr |
| Pro | Ala, Gly |
| Ser | Thr, Ala, Cys |
| Thr | Ser |
| Trp | Tyr, Phe |
| Tyr | Trp, Phe, Thr, Ser |
| Val | Ile, Met, Leu, Phe, Ala, Norleucine |

A skilled artisan will be able to determine suitable variants of a polypeptide as set forth herein using well-known techniques. One skilled in the art can identify suitable areas of the molecule that can be changed without destroying activity by targeting regions not believed to be important for activity. The skilled artisan can identify residues and portions of the molecules that are conserved among similar polypeptides. In certain embodiments, even areas that can be important for biological activity or for structure can be subject to conservative amino acid substitutions without destroying the biological activity or without adversely affecting the polypeptide structure.

Exemplary ribosomal protein variants include cysteine variants wherein one or more cysteine residues are deleted from or substituted for another amino acid (e.g., serine) relative to the amino acid sequence of the reference ribosomal protein. In certain embodiments, cysteine variants have fewer cysteine residues than the native or wild type polypeptide. A "wild type cyteine residue" is one that occurs in the native polypeptide sequence.

Additional guidance with respect to making and using nucleic acids and polypeptides is found in standard textbooks of molecular biology, protein science, and immunology (see, e.g., Davis et al., Basic Methods in Molecular Biology, Elsevier Sciences Publishing, Inc., New York, N.Y., 1986; Hames et al., Nucleic Acid Hybridization, IL Press, 1985; Molecular Cloning, Sambrook et al., Current Protocols in Molecular Biology, Eds. Ausubel et al., John Wiley and Sons; Current Protocols in Human Genetics, Eds. Dracopoli et al., John Wiley and Sons; Current Protocols in Protein Science, Eds. John E. Coligan et al., John Wiley and Sons; and Current Protocols in Immunology, Eds. John E. Coligan et al., John Wiley and Sons).

Additionally, in certain embodiments, one skilled in the art can review structure-function studies identifying residues in similar polypeptides that are important for activity or structure. In view of such a comparison, in certain embodiments, one can predict the importance of amino acid residues in a protein that correspond to amino acid residues which are important for activity or structure in similar proteins. In certain embodiments, one skilled in the art can opt for chemically similar amino acid substitutions for such predicted important amino acid residues.

While prokaryotic organisms utilize both RF1 and RF2 to specifically decode the three stop codons, eukaryotic organisms use a single homolog, eRF1, to recognize all three stop codons during eukaryotic termination. Despite a considerable lack of sequence homology, RF1, RF2, and eRF1 demonstrate universal conservation of the structure and function of class I release factors (Petry et al. 2005; Vestergaard et al. 2005). Likewise, there exists a eukaryotic class II GTPase release factor, eRF3. Although some differences in the details of RF3 and eRF3 function have been noted (Alkalaeva et al. 2006; Mitkevich et al. 2006; Pisareva et al. 2006), RF3 and eRF3 play similar functional roles in a universal termination mechanism (Zavialov et al. 2002; Zavialov et al. 2001). The GS2 state of the ribosome has been observed in cryo-EM studies of both prokaryotic (Connell et al. 2007; Valle et al. 2003) and eukaryotic (Taylor et al. 2007; Spahn et al. 2004) elongation complexes as well as in prokaryotic TCs (Gao et al. 2007a; Klaholz et al. 2004).

Thus, in certain embodiments, one skilled in the art can analyze the three-dimensional structure and amino acid sequence in relation to that structure in similar polypeptides. For example, the skilled artisan can compare three-dimensional structures between several RF1 molecules from different prokaryotes. In addition, the skilled artsian can compare three-dimensional structures of RF1 to eRF to guide design of labeled mutants. In view of such information, one skilled in the art can predict the alignment of amino acid residues of protein with respect to its three dimensional structure. In certain embodiments, one skilled in the art can choose not to make radical changes to amino acid residues predicted to be on the surface of the protein, since such residues can be involved in important interactions with other molecules. Moreover, in certain embodiments, one skilled in the art can generate test variants containing a single amino acid substitution at each desired amino acid residue. In certain embodiments, the variants can then be screened using activity assays known to those skilled in the art. In certain embodiments, such variants could be used to gather information about suitable variants. For example, in certain embodiments, if one discovered that a change to a particular amino acid residue resulted in destroyed, undesirably reduced, or unsuitable activity, variants with such a change can be avoided. In other words, in certain embodiments, based on information gathered from such routine experiments, one skilled in the art can readily determine the amino acids where further substitutions should be avoided either alone or in combination with other mutations.

A number of scientific publications have been devoted to the prediction of secondary structure. See, e.g., Moult J., Curr. Opin. Biotechnol. (1996) 7(4):422-427; Chou et al., (1974) Biochemistry, 13(2):222-245; Chou et al. (1974) Biochemistry 113(2):211-222; Chou et al. (1978); Adv. Enzymol. Relat. Areas Mol. Biol. 47:45-148; Chou et al. (1976) Ann. Rev. Biochem. 47:251-276; and Chou et al. (1979) Biophys. J. 26:367-384. Moreover, computer programs are currently available to assist with predicting secondary structure. One method of predicting secondary structure is based upon homology modeling. For example, two polypeptides or proteins which have a sequence identity of greater than 30%, or similarity greater than 40% often have similar structural topologies. The growth of the protein structural database (PDB) has provided enhanced predictability of secondary structure, including the potential number of folds within a polypeptide's structure. See, e.g., Holm et al. (1999) Nucl. Acid. Res. 27(1):244-247. It has been suggested (Brenner et al., (1997) Curr. Op. Struct. Biol. 7(3):369-376) that there are a limited number of folds in a given polypeptide or protein and that once a critical number of structures have been resolved, structural prediction will become dramatically more accurate.

Additional methods of predicting secondary structure include "threading" (see, e.g., Jones, D. (1:997) Curr. Opin. Struct. Biol. 7(3):377-387; Sippl et al. (1996) Structure 4(1):15-19), "profile analysis" (see, e.g., Bowie et al., (1991) Science 253:164-170; Gribskov et al., (1990) Meth. Enzym. 183:146-159; Gribskov et al. (1987) Proc. Nat. Acad. Sci. USA 84(13):4355-4358), and "evolutionary linkage" (see, e.g., Holm et al. (1999) Nucl. Acid. Res. 27(1):244-247; and Brenner et al. (1997) Curr. Op. Struct. Biol. 7(3):369-376 (1997)).

Ribosome Dynamics During Termination and Recycling

Determining how the GS1 GS2 equilibrium is coupled to the activities of release and ribosome recycling factors is useful for understanding the role of conformational dynamics of the translational machinery in the termination and ribosome recycling. The results described herein show that the global state of the ribosome is a mechanistic feature of translation factors and a regulatory strategy that is used throughout protein synthesis.

The tight binding of RF1 to a post-hydrolysis RC establishes intermolecular RF1-ribosome, and possibly intramolecular ribosome-ribosome interactions, which block GS1⇌GS2 fluctuations that are otherwise intrinsic to ribosomal complexes carrying a deacylated P-site tRNA (FIGS. 3A and 3B). Thus, without making extensive interactions with the P-site tRNA or any contacts with the L1 stalk, RF1 successfully blocks movements of P-site tRNA from the classical to the hybrid configuration, movements of the L1 stalk from the open to the closed conformation, and presumably, the accompanying intersubunit ratcheting of the ribosome. This result shows the tight coupling between ribosome and tRNA dynamics and that the interaction of translation factors with the ribosome can allosterically and specifically regulate the global state of the ribosome.

The finding that RF1 Δd1 can block GS1→GS2 transitions demonstrates that any potential intersubunit interactions mediated by domain 1 are not essential for blocking GS1→GS2 transitions. Because domain 1 is not required to block this transition, an alternative mechanism involve base-stacking interaction between A1913 from helix 69 of 23S rRNA and A1493 from helix 44 of 16S rRNA, which was observed in a recent X-ray crystal structure of RF1 bound to an RC (Laurberg et al. 2008). This contact physically connects the two subunits, is a distinctive feature of an RF1-bound RC, and might therefore play a role in preventing the GS1→GS2 transition. RF1, helix 69, and/or helix 44 mutations can be performed to test this possibility.

The smFRET data demonstrate that the target of RF3 (GDP) is a post-hydrolysis, RF1-bound RC locked in GS1, and that the intrinsic GS1→GS2 transition remains suppressed throughout the interaction of the RF1-bound RC with RF3(GDP) and nucleotide-free RF3. The GS1→GS2 transition occurs exclusively upon binding of GTP to RC-bound RF3, which leads to RF1 dissociation and stabilization of GS2 prior to GTP hydrolysis (FIG. 3C). The results described herein show that the characteristic fluctuations between GS1 and GS2 that are triggered by deacylation of the P-site tRNA are specifically regulated throughout the termination pathway. It is possible that binding of GTP to RC-bound RF3 actively drives the GS1→GS2 transition, indirectly leading to RF1 dissociation (Gao et al. 2007a). It is also possible that binding of GTP to RC-bound RF3 actively drives RF1 dissociation and enables GS1→GS2 transition spontaneously in the absence of RF1.

As is the case during elongation and termination, the GS1⇌GS2 equilibrium is specifically regulated, during ribosome recycling. The smFRET data described herein demonstrates the ability of RRF to shift the GS1⇌GS2 equilibrium towards an RRF-bound GS2 conformation as a function of increasing RRF concentration. This occurs through two mechanisms. At low concentrations, RRF preferentially and transiently binds to GS2, competing directly with the GS2→GS1 transition and inhibiting $k_{GS2→GS1}$ in a concentration-dependent manner (FIG. 3D). At high concentrations, RRF can also bind directly to GS1 and modestly increase $k_{GS1→GS2}$. Tunable shifting of the GS1⇌GS2 equilibrium towards an RRF-bound PoTC in GS2 sets important constraints for subsequent steps of ribosome recycling. For example, the RRF-bound PoTC in GS2, which can serve as the substrate for EF-G-catalyzed splitting of the ribosomal subunits, is a transient species whose fractional population is a sensitive function of RRF concentration. Accordingly, the efficiency of ribosome recycling can be dependent on RRF concentration, as has been demonstrated in vitro (Pavlov et al. 2008; Hirokawa et al. 2005). These results further show that cellular control of RRF concentrations can regulate the efficiency of ribosome recycling in vivo, which can be important for reactivating sequestered ribosomes (Janosi et al. 1998) and preventing unscheduled translation reinitiation events (Hirokawa et al. 2004).

The ribosome interacts with numerous translation factors throughout protein synthesis, many of which bind at partially overlapping sites and thus compete for ribosome binding. Biochemical studies have shown that the absence or presence of a peptide on P-site tRNA regulates the activities of the translational GTPases (Zavialov et al. 2003). As described herein, an additional level of organizational control exists in which the absence or presence of a peptide on the P-site tRNA controls a dynamic equilibrium involving coupled tRNA and ribosome dynamics. This dynamic equilibrium is recognized and manipulated by elongation, release, and ribosome recycling factors during the elongation, termination, and recycling stages of translation (FIG. 3). Thus, given the universally conserved two-subunit architecture of the ribosome, as well as the conserved ability of eukaryotic ribosomes to sample GS1- and GS2-like conformations(Taylor et al. 2007; Spahn et al. 2004), regulation of the GS1⇌GS2 equilibrium serves as a universal principle for organizing the binding and biochemical activities of translation factors throughout protein synthesis.

The following examples illustrate the present invention, and are set forth to aid in the understanding of the invention, and should not be construed to limit in any way the scope of the invention as defined in the claims which follow thereafter.

EXAMPLES

Example 1

General Methods

Protocols describing (1) the Tris-Polymix buffer system, (2) the purification of ribosomes, tRNA synthetases, formylmethionyl-tRNA formyltransferase, and translation factors, (3) the specific fluorescent-labeling of tRNAPhe as well as purification of fluorescently-labeled tRNAs, (4) the aminoacylation of tRNAs, preparation of the 10-formyltetrahydroformate formyl group donor and formylation of Met-tRNAfMet, (5) the formation of EFTu(GTP)aa-tRNA complexes, and (6) the preparation and purification of ribosomal complexes initiated on chemically synthesized mRNAs harboring a 5'-biotin modification, (7) extract and analyze ribosomal proteins, (8) generate ribosomal protein deletion strains, (9) clone, mutagenize, overexpress, purify, and fluorescently label ribosomal proteins, and (10) reconstitute ribosomes bearing single fluorescently-labeled ribosomal proteins are previously published (Fei et al. 2008; Gonzalez et al. 2007; Blanchard et al. 2004a; Blanchard et al. 2004b) and described in part below.

Example 2

Cloning and Purification of Release and Ribosome Recycling Factors

Genes encoding RF1, RF3, and RRF from *Escherichia coli* C600 genomic DNA were cloned into the pProEx-HTb vector (Invitrogen), which contains an ampicillin-resistance marker, using KasI (5') and KpnI (3') restriction sites, which places the gene under Trc promoter control and appends an N-terminal hexahistidine affinity tag (SEQ ID NO: 9) and downstream TEV protease cleavage site. Enzymatic cleavage of the affinity tag leaves an extraneous GA dipeptide at the N terminus of each protein factor.

The PrmC gene encoding the RF1-modifying glutamine-N-5-methyltransferase was cloned from *E. coli* genomic DNA into the pET-26b(+) vector (Novagen), containing a kanamycin-resistance marker and an IPTG-induced T7 promoter, using NdeI (5') and HindIII (3') restriction sites. Appendage of the optional C-terminal hexahistidine affinity tag (SEQ ID NO: 9)was avoided by placing a stop codon at the C terminus of the gene. The RF1Δd1 construct was generated by deleting the region of the PrfA gene encoding amino acids 1-89, as previously described (Mora et al. 2003).

Design of single-cysteine variants of RF1 was guided by crystal structures of RF1 bound to a RC (Petry et al. 2005) to identify a series of single-cysteine RF1 mutants that retain full RF1 function (Wilson et al. 2000). All clones were verified by DNA sequencing.

After cloning genes encoding RF1, RF1Δd1, RF3, and RRF, protein factors were overexpressed in BL21 cells, purified using Ni2+-nitrilotriacetic acid affinity chromatography, and TEV protease was used to cleaved their hexahistidine affinity tags (SEQ ID NO: 9). RF1 and RF1Δd1 were co-expressed with a plasmid-encoded copy of the PrmC gene, an N5-glutamine methyltransferase known to methylate RF1 at residue Gln235 (Heurgue-Hamard et al. 2002; Dincbas-Renqvist et al. 2000). All purified proteins were greater than 95% pure, as evidenced by SDS-PAGE (FIG. 4A), and their identities were confirmed by mass spectrometry. Final protein stocks were stored at −20° C. in Translation Factor Buffer (10 mM Tris-Cl pH4° C.=7.5, 50 mM KCl, 5 mM 2-mercaptoethanol, and 50% (v/v) glycerol). All translation factors were purified using Ni2+-NTA affinity purification chromatography followed by TeV protease cleavage of the hexa-histidine affinity tags (SEQ ID NO: 9) as described.

Example 3

Preparation of IFs, EFs, tRNAs, mRNA and L1(Cy5) Ribosomes

Initiation and elongation factors were purified as previously described (Blanchard et al. 2004b). tRNA$^{Phe}$ (Sigma-Aldrich) was labeled with Cy3—NHS ester (GE Healthcare) at the naturally occurring acp$^3$U modification at position 47, and purified using hydrophobic interaction chromatography (Blanchard et al. 2004b). tRNA$^{fMet}$ (MP Biomedicals), tRNA$^{Phe}$, and (Cy3)tRNA$^{Phe}$, and formylated Met-tRNA$^{fMet}$ was aminoacylated (Blanchard et al. 2004b). The mRNA used in this analysis is derived from the mRNA encoding gene product 32 from T4 bacteriophage. The sequence of this mRNA is:

(SEQ ID NO: 5)
GG<u>CAACCUAAAACUUACACAG</u>GGCCC<u>UAAGGA</u>AAUAAAA*AUGUUUUAAUG*

UAAA (SEQ ID NO: 6)
UCUACUGCUGAACUCGCUGCACAAAUGGCUAAACUGAAUGGCAAUUAAGG

AUC, where the nucleotides in bold are a 26 nucleotide spacer region containing an 18 nucleotide sequence (underlined in bold) to which a complementary 3'-biotinylated DNA oligonucleotide (IDT; TGTGTAAGTTTTAGGTTGATTTG-Biotin (SEQ ID NO: 7) was hybridized to enable surface immobilization. This was followed by a strong Shine-Dalgarno ribosomal binding site (underlined), an open reading frame encoding fMet-Phe-STOP within a strong stop codon context (Pavlov et al. 1998) (underlined in italics), and 58 additional downstream nucleotides. For control experiments with a sense codon, the mRNA was identical except for the beginning of the open reading frame sequence, which was mutated to AUG UUU AAA C (SEQ ID NO: 8). L1(Cy5) ribosomes were constructed as previously described (Fei et al. 2008).

Example 4

Preparation and Purification of TCs and PoTCs

A bacteriophage T4 gene product 32-derived mRNA (Blanchard et al. 2004b) as well as a variant having mutated the third codon, and the +1 downstream nucleotide from the wild-type AAA-C (coding for lysine) to UAA-U (the most efficient RF1 stop-codon in the most efficient codon context) was used. TCs were prepared by initiating ribosomes on a biotinylated mRNAs as previously described (Blanchard et al. 2004b). These initiated ribosomes were then in-vitro reacted through one full round of translation elongation using fully-purified EF-Tu(GTP)Phe-tRNAPhe and EFG (GTP). This method enables ~90-95% efficiency in this elongation step using a purified in vitro translation system (Fei et al. 2008; Blanchard et al. 2004b). This places a deacylated-tRNAfMet at the deacylatedtRNA (or exit (E)) site, an fMet-Phe-tRNAPhe at the P site, and the stop codon at the empty aa-tRNA binding (A) site (FIG. 1A). TCs prepared in this way were purified from free tRNAs and translation factors by ultracentrifugation through a sucrose density gradient as previously described (Blanchard et al. 2004b).

Example 5

Generation and Labeling of RF1 Mutants

In order to fluorescently label release factor 1 (RF1), maleimide-reactive fluorophores were conjugated with the thiol side group of unique cysteine residues, and introduced into the RF1 gene (prfA) using standard molecular biology tools. The generation of RF1 mutants involves: identifying high-interest regions for fluorophore placement, scoring amino acid residues within these regions for conservation and surface accessibility, consulting prior work to determine whether potential mutations have already been generated/characterized, and constructing the desired mutations by mutagenesis.

High-resolution structures of release factor 1 (RF1), either crystallized alone (PDB IDs 1RQ0 and IZBT) or bound to ribosomes (PDB IDs 2B64/6 and 3D5A/B), were analyzed using Pymol (http://www$_{13}$ pymol.org/) to identify regions of interest for conjugating a fluorophore(s). When designing FRET experiments, distances between potential points of attachment within these structures were measured to guide the construction of RF1 mutations. Otherwise, high-interest regions were generally identified based on prior studies and/or a targeted focus on specific RF1 domain movements inferred from previous structural and biochemical work.

After selecting regions where a fluorophore was desired, the *Escherichia coli* gene encoding RF1 was aligned with the sequences of ~250 other bacterial RF1 genes using BLAST (http://blast_ncbi.nlm.nih.gov/Blast.cgi). The resulting sequence alignment was analyzed with ClustalW (http://www ebi.ac.uk/clustalw/) and Jalview (http://www jalview.org/), and amino acid residues in close proximity to regions of interest were scored for conservation; residues with low levels of conservation were selected as potential candidates for mutational work. Crystal structures were again consulted in order to assess the solvent accessibility of amino acid residues identified through phylogenetic analysis, as fluorescent labeling efficiencies will ultimately be limited by the accessibility of the reactive thiol group. Those residues within high interest regions, showing low conservation and good solvent accessibility, were ultimately selected for introducing mutations. These selections were further filtered based on any prior studies that may have already generated and biochemically tested similar mutants. For example, Wilson et al. (*Nat Struct Biol* 7(10), 866-870 (2000)) generated 10 unique, active single-cysteine RF1 mutants, which was a useful starting point to guide the labeling strategy.

In order to place unique cysteines within the RF1 sequence, all three wild-type cysteines were first mutated to serines, generating a cysteine-free RF1 construct previously shown to retain activity. Subsequently, new mutations were introduced within the RF1 gene. In most cases, mutations were generated using the Quikchange Site-Directed Mutagenesis Kit (http://www stratagene.com). All mutations were verified by DNA sequencing.

Figure 5:
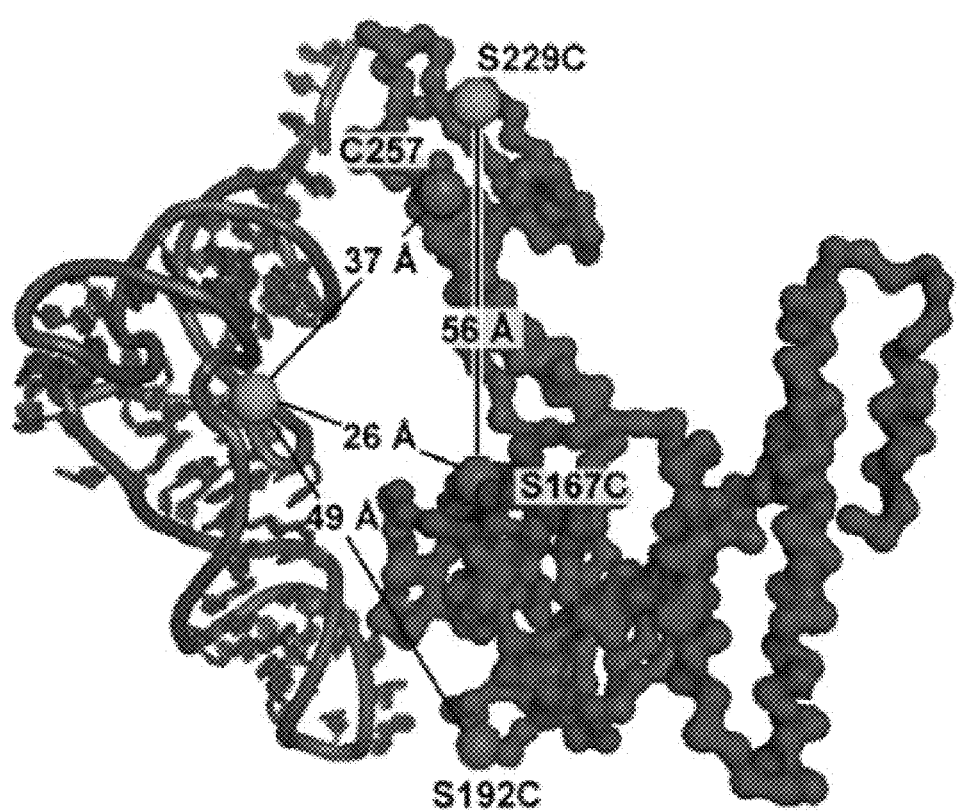
FIG. 5 shows relative distances between Psite (Cy3)tRNA and (Cy5)RF1 variants. Distances between P-site tRNA (left) and RF1 (right) are based on a low resolution structure of RF1 bound to the A site of a RC (Petry et al. 2005); the ribosome has been omitted for clarity. The relative distances between the Cy3 label on the P-site tRNA (green sphere) and each of the three single-Cy5 labeled RF1s (red spheres) are denoted. The two positions that have been constructed as a doubly-labeled RF1 mutant are denoted by a green sphere at S229C and a red sphere at S167C.

All wild-type cysteines (C51, C201, C257) were first mutated to serines to generate a cysteine-free RF1 construct, except where noted[†], before generating the following single/double cysteine constructs:
S167C
S192C
C201[†]
S229C
E256C
C257[†]
S167C/S229C
S192C/S229C
C201/C257[†]
S192C/E256C
S192C/E256C
141C/256C
328C/256C
256C/315C
192C/254C
328C/167C Three single-cysteine RF1 mutants predicted to yield RF1-tRNA smFRET signals emanating from the core domain (S167C), the PVT domain (S192C), and the GGQ domain (C257, a wild-type cysteine) of RF1 were identified and generated (FIG. 5). All translation factors were overexpressed as previously described (Blanchard et al. 2004b), with the exception of RF1 variants, all of which were co-overexpressed with PrmC in order to ensure methylation of the glutamine within the GGQ motif.

To enable site-specific Cy5-labeling of RF1 and RF1Δd1, a single-cysteine mutant previously shown to retain wild-type activity (Wilson et al. 2000) was generated by mutating all wild-type cysteines to serines (C51S C201S C257S) and engineering an additional S167C mutation into RF1 domain 2 using the Quikchange Mutagenesis Kit (Stratagene).

Other single-cyteine constructs, including A200C and T198C, can be generated in the manner described above. Other double-cysteine constructs can also be generated in the manner described above.

Example 6

Generation of eRF1 Mutants

Bacterial release factor 1 (RF1) and eukaryotic RF1 (eRF1), which share no overall sequence homology, have a similar L shape characteristic of tRNAs. This enabled structural alignment of RF1 and eRF1, as follows: for bacterial RF1, a recent structure of *Thermus thermophilus* RF1 bound to the 70S ribosome (PDB code 3D5A) (Laurberg et al. 2008); for eukaryotic RF1 was used, a recent structure of *Homo sapiens* eRF1 in complex with eRF3 (PDB code 3E1Y) (Cheng et al. 2009) was used. Using Swiss-Pdb Viewer (Guex et al. 1997), structural alignment of RF1 and eRF1 was guided by fitting the following three selected sequences (all mention of bacterial RF1 amino acid residues uses numbering from *Escherichia coli*; mention of eRF1 amino acid residues uses numbering from *H. sapiens* unless otherwise noted):
1) Universally conserved GGQ motifs (233-235 in RF1, 183-195 in eRF1);
2) Stop-codon recognition motifs (188PAT190 in RF1, 62IKS64 in eRF1);
3) A284 in RF1 and E269 in eRF1.

After modeling in the positions of mutations previously made to generate single-cysteine *E. coli* RF1 mutants, potential single-cysteine eRF1 constructs in *H. sapiens*, *Schizosaccharomyces pombe*, and *Saccharomyces cerevisiae* were selected by first identifying wild-type cysteine residues needing to be mutated out, and generating alignments of protein sequences for both *H. sapiens* eRF1 and *S. pombe/S. cerevisiae* with ~250 other related sequences using BLAST (Altschul et al. 1990). These alignments and the structural model were used to identify amino acid residues of interest for fluorophore conjugation, paying close attention to: proximity to previously identified high-interest regions in *E. coli* RF1; degree of conservation of target residues based on the sequence alignments; and extent of solvent accessibility according to the structural model.

The following mutations in eRF1 were identified on the basis of the above criteria. In cases where eRF1 mutations from separate species are listed together, they are presented in the order *H. sapiens/S. pombe/S. cerevisiae*.
Mutation of *H. sapiens* eRF1 Wild-Type Cysteine Residues:
  C97T (medium conservation)
  C127S (high/total conservation)
  C302V (medium/low conservation)
  C335N (low conservation)
Mutation of *S. pombe* (Chromosome I) eRF1 Wild-Type Cysteine Residues:
  C24A (medium conservation)
  C94T (medium conservation)
  C124S (high/total conservation)
  C299V (medium conservation)
  C319V (medium conservation)
Mutation of *S. cerevisiae* eRF1 Wild-Type Cysteine Residues:
  C94T (medium conservation)
  C124S (high/total conservation)
  C245A (low conservation)
  C299V (medium conservation)
Mutations to Mirror *E. coli* S229C Mutation (Vicinity of GGQ Motif):
  G181C/G178C/G178C
  L188C/L185C/L185C
  Mutations to Mirror *E. coli* C257/E256C Mutations (Vicinity of GGQ Motif):
  S229C/S226C/S226C
  G153C/G150C/G150C
  S154C/H151C/Q151C
Mutations to Mirror *E. coli* S167C Mutation ('Elbow' Region):
  N121C/N118C/N118C
  D9C/E6C/E6C
  T137C/A134C/S134C
Mutations to Mirror *E. coli* S192C Mutation (Vicinity of Stop Codon Recognition Motif):
  T58C/T55C/T55C
  V66C/V63C/V63C
  L69C/L66C/L66C
Mutations to Mirror *E. coli* C201/A200C/T198C Mutations (Vicinity of Stop Codon Recognition Motif):
  N129C/N126C/N126C
  L126C/L123C/L123C
  N30C/N27C/N27C Example 7

Fluorescent Labeling of Translation Factors Involved in Termination and Recycling Single-cysteine S167C RF1 and RF1Δd1 mutants were reacted with a ~20-fold molar excess of Cy5-maleimide (GE Healthcare) overnight at 4° C. in Protein Labeling Buffer (100 mM Tris-OAc, $pH_{25°\ C.}$=7.0, 50 mM KCl, 1 mM tris(2-carboxyethyl)phosphine hydrochloride). The reaction was subsequently injected onto a 60 cm HiLoad Superdex 75 gel filtration column (GE Healthcare) pre-equilibrated against Gel Filtration Buffer (20 mM Tris-Cl, $pH_{4°\ C.}$=7.5, 100 mM KCl, 10 mM 2-mercaptoethanol), and separated RF1/RF1Δd1 from unreacted dye by elution with 1.5 column volumes of Gel Filtration Buffer running at a flow rate of 1 ml min$^{-1}$ (FIG. 4B). RF1, RF1Δd1, and unreacted dye was eluted at 59, 65, and 113 minutes, respectively. Protein fractions were concentrated and exchanged into Buffer A (100 mM Na$_2$HPO$_4$, $pH_{25°\ C.}$=7.0, 1 M (NH$_4$)$_2$SO$_4$), and the sample was subsequently injected onto a TSKgel Phenyl-5PW hydrophobic interaction column (Tosoh Bioscience) pre-equilibrated against Buffer A. Cy5-labeled RF1/RF1Δd1 was separated from unlabeled RF1/RF1Δd1 by elution with a Buffer B (100 mM Na$_2$HPO$_4$, $pH_{25°\ C.}$=7.0) gradient extending from 0% to 100% over 60 minutes running at a flow rate of 1 ml min$^{-1}$ (FIG. 4C). RF1, RF1Δd1, RF1(Cy5), and RF1Δd1(Cy5) eluted at 38%, 35%, 68%, and 70%

Buffer B, respectively. This purification procedure yields 100% homogenously-labeled RF1(Cy5)/RF1Δd1(Cy5).

L1(Cy5) ribosomes and Phe-(Cy3)tRNAPhe were prepared as described in Example 3. Fluorescent release factor was prepared as described herein, by mutagenizing E. coli RF1 to contain a single cysteine at position 167 within domain 2. This mutant RF1 demonstrates peptide release activity comparable to wild-type RF1 (Wilson et al. 2000). Purified single-cysteine RF1 was reacted with Cy5-maleimide and separated from unreacted dye by gel filtration; further separation of unlabeled RF1 using hydrophobic interaction chromatography generated 100% homogeneously-labeled RF1(Cy5) (FIG. 4). Purified translation factors were shown to be greater than 95% pure as assayed by 10% SDS-polyacrylamide gel electrophoresis (FIG. 4A). The thiol groups on purified single-cysteine RF1 mutants and on wild-type RRF, which contains a single cysteine residue, were then labeled with a malemide-derivatized Cy5 fluorescent dye according to the manufacturer's directions (GE Biosciences, Inc.). (Cy5)RF1s and (Cy5)RRF were then separated from unreacted Cy5-maleimide by gel filtration chromatography and further purified from unlabeled RF1 or RRF by hydrophobic interaction chromatography (FIG. 4C). The procedure yields site-specifically 100% Cy5-labeled RF1s and RRF.

In addition to the single-cysteine RF1 mutants, a comparison of the closed (Blanchard et al. 2004a; Shin et al. 2004) and open (Petry et al. 2005) forms of RF1 was used to generate a double-cysteine RF1 mutant, S192C/S229C (FIG. 5). This double-cysteine RF1 mutant was reacted with equal amounts of Cy3- and Cy5-maleimide, free dyes were separated from RF1 using gel filtration chromatography, and doubly-labeled RF1 was separated from unreacted and singly-labeled RF1 using hydrophobic interaction chromatography.

Example 8

RF1 and RF3 Activity Assays

Figure 6:
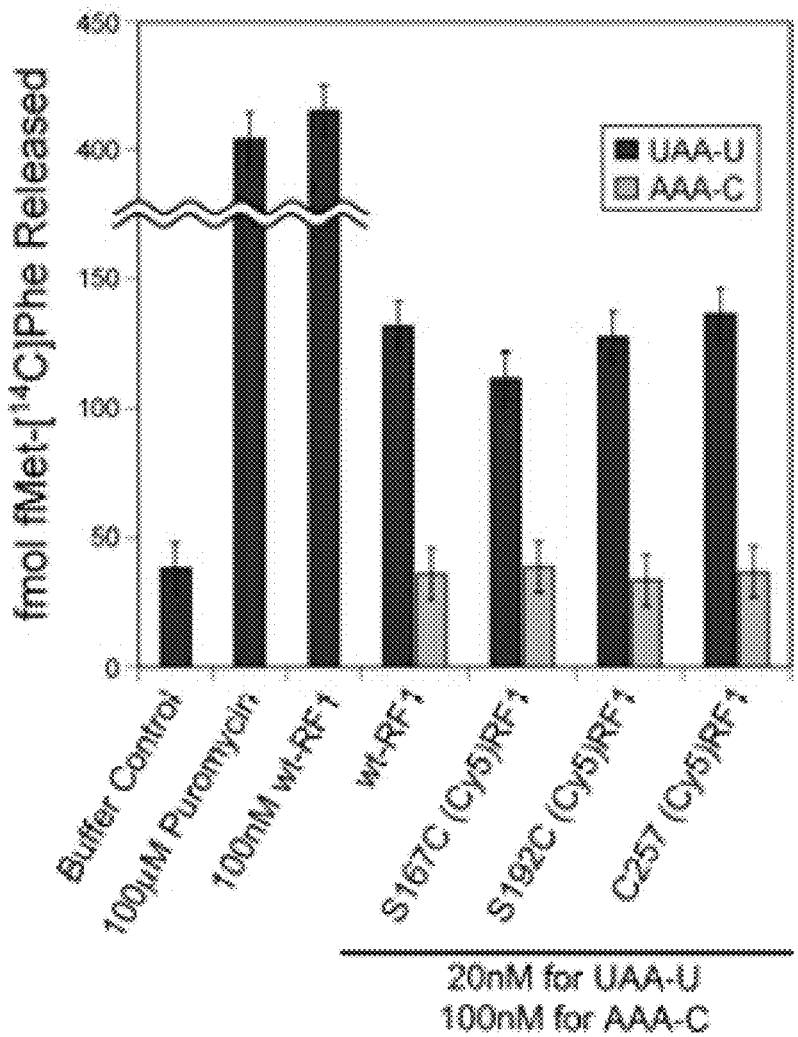
FIG. 6 shows a bulk biochemical assay for RF1 function. Ribosomal TCs carrying a [14C]-labeled dipeptide (~50 nM) and either buffer, puromycin or RF1 (at indicated concentrations) were reacted at 37° C. for 1 minute. An equal volume of 25% formic acid was added to each reaction to precipitate ribosomes, and after a 30 minute centrifugation step, the radioactivity in both the supernatant and pellet was quantified using scintillation counting. The fmol of [14C]-labeled dipeptide released into the supernatant in each reaction is depicted in the bar graph.

Standard peptide release assay was used to show that RF1(Cy5) demonstrates stop codon-dependent peptide release activity that is indistinguishable from wild-type RF1 (FIG. 6). Radioactive RCs were formed following a similar protocol as with RC1 but using [14C]Phe-tRNAPhe during the elongation step rather than Phe-(Cy3)tRNAPhe. The resulting complexes contain an [14C]-labeled dipeptide at the P site. Additionally, instead of sucrose density gradient ultracentrifugation, RCs were separated from free GTP and GDP by buffer exchange into fresh Tris-polymix buffer, 5 mM Mg(OAc)$_2$ using two successive Micro Bio-Spin 30 chromatography columns (Bio-Rad Laboratories). RCs were then aliquoted and frozen in liquid nitrogen, and stored at −80° C. RCs were ~85% active in peptide bond formation, as determined by the efficiency of deacylating P-site fMet-[14C]Phe-tRNAPhe with the antibiotic puromycin.

Wild-type RF1, RF1(Cy5), RF1Δd1, and RF1Δd1(Cy5) were tested for peptide release activity (Freistroffer et al. 1997), and the proportion of active RF1 was estimated for each individual construct by single-round dipeptide release in the presence of excess RF3 without guanine nucleotide (Zavialov et al. 2001). Briefly, RCs and RF1 (with RF3) were pre-incubated separately for 1 minute at 37° C., and then mixed and reacted at 37° C. for 1 minute. Reactions were quenched by adding an equal volume of ice-cold 25% formic acid, and after a 15 minute incubation on ice. The [14C]-labeled dipeptide released into solution can be separated from unreacted, (i.e. ribosome associated) [14C]-labeled dipeptide by pelleting the ribosome with formic acid. Precipitated components were separated from any released dipeptide by microcentrifugation at 14,000×g. The extent of peptide hydrolysis was determined by measuring the radioactivity in both the pellet and supernatant with scintillation counting, subtracting the amount of background peptide release from a buffer reaction control, and using a calibration curve to deduce the molar amount of dipeptide released based on the counts per minute (cpm). A negative control, addition of buffer in place of RF1, yields very little 14C associated with the supernatant whereas a positive control, addition of the antibiotic puromycin in place of RF1, yields almost quantitative release of 14C into the supernatant.

Percent activities, calculated as the amount of dipeptide released divided by the amount of RF1 in the reaction, were 30-40% for wild-type RF1 and RF1(Cy5), and ~10% for RF1 Δd1 and RF1Δd1(Cy5). The stop-codon dependence of RF1-catalyzed peptide release was tested by reacting RF1 with RCs stalled on a lysine codon (AAA) at position three instead of a stop codon (UAA). No dipeptide release was detected above background for any of the RF1 constructs. RF1 concentrations given in captions for FIG. 7 and FIG. 8 correspond to active concentrations. The release activities of wild-type and all (Cy5)RF1 variants is dependent on the presence of a stop-codon at the A site (FIG. 6). This biochemical assay can also be used to test the activity of doubly-labeled RF1.

Figure 8:
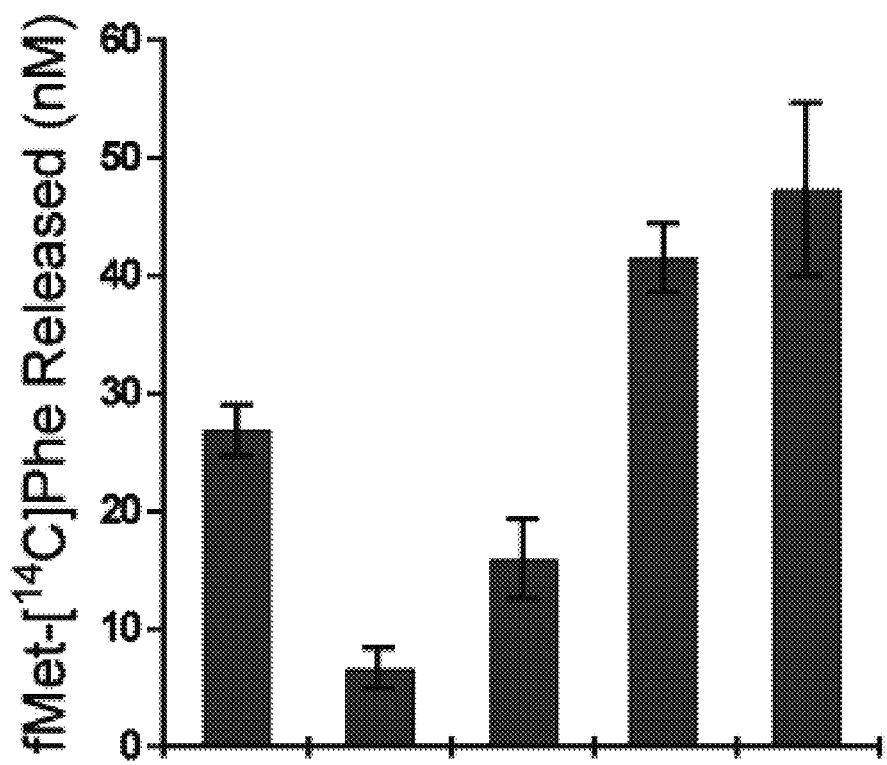
FIG. 8 shows a RF3 activity assay. RCs (~58 nM) carrying a stop codon (UAA) at the A site and fMet-[$^{14}$C] Phe-tRNA$^{Phe}$ in the P site were reacted with substoichiometric wild-type RF1 (5 nM) and, when present, RF3 (200 nM) and the nucleotide shown (0.2 mM) for 10 minutes at 37° C. The nucleotide dependency of RF3-catalyzed RF1 recycling is consistent with previous results (Zavialov et al. 2001). Error bars represent the standard deviation from three independent experiments.

RF3 activity was tested by following the extent of peptide release in cases where RF1 was limiting and RF3 was required to actively recycle RF1, thereby enabling multiple turnover (Zavialov et al. 2001). Reactions were performed as described, with two exceptions: when present, GDP, GTP, or GDPNP was added to the RF1/RF3 mix during the 1 minute pre-incubation, and upon adding the RF1/RF3/nucleotide mix to RCs, reactions were incubated for 10 minutes. FIG. 8 demonstrates that RF3 exhibits the proper nucleotide dependence in recycling RF1.

Example 9

RRF Activity Assay

Figure 9:
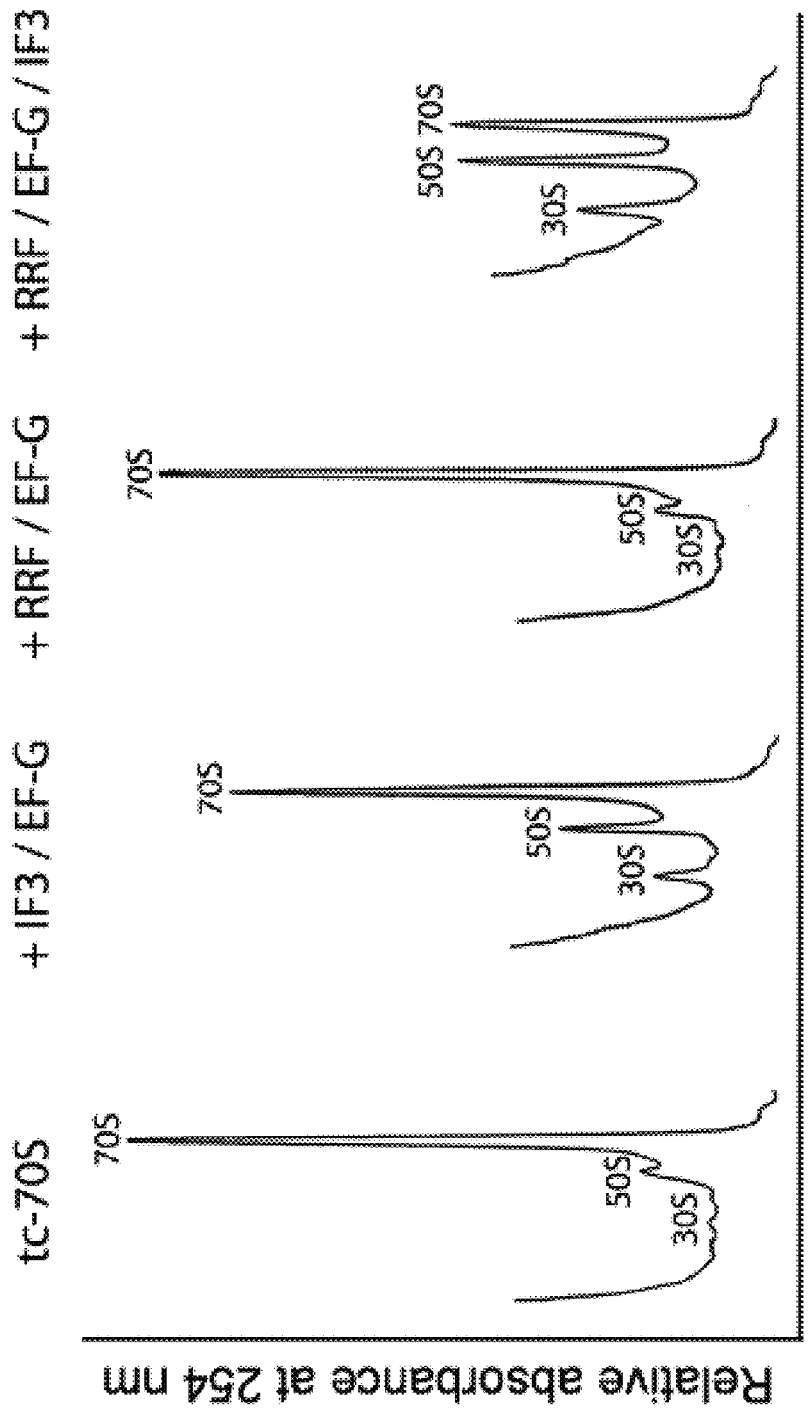
FIG. 9 shows a RRF activity assay. Tightly-coupled 70S ribosomes (0.2 μM) (alone or with 0.5 mM GTP) and the proteins shown ([IF3]=5 μM, [EF-G]=20 μM, [RRF]=20 μM) were incubated for 20 minutes at 37° C. in Tris-polymix buffer, 6 mM Mg(OAc)$_2$. Reactions were loaded onto sucrose gradients and analyzed them as described herein. Sedimentation is from left to right, and peaks for 30S, 50S, and 70S ribosomes are indicated. Each experiment was performed at least twice. Data from representative sucrose gradients are shown.

RRF was tested for its ability to split 70S ribosomes into 30S and 50S subunits, as detected by sucrose density gradient ultracentrifugation (Hirokawa et al. 2005). Briefly, reaction mixtures consisting of 0.2 μM tightly-coupled 70S ribosomes and a combination of 20 μM RRF, 20 μM EF-G, 5 μM IF3 and 0.5 mM GTP, were reacted for 20 minutes at 37° C. in Tris-polymix buffer, 6 mM Mg(OAc)$_2$. After a brief incubation on ice, reaction mixtures were subsequently onto a 10%-40% sucrose density gradient in the same Tris-polymix buffer, followed by ultracentrifugation in an SW40 rotor (Beckman Coulter) at 25,000 rpm for 12 hours at 4° C. Gradients were analyzed by monitoring the absorbance at 254 nm with a gradient analyzer (Brandel). The extent of 70S dissociation under the conditions described herein is shown in FIG. 9 (Hirokawa et al. 2005).

Example 10

Ribosomal Release Complex Formation and Purification

Two RCs were enzymatically prepared using the fluorescent reagents (see Example 7) in a highly-purified in vitro translation system (FIG. 2D). RC1 comprises a wild-type ribosome, 5'-biotinylated mRNA, fMet-Phe-(Cy3)tRNA$^{Phe}$ in the P site, and an empty A site programmed with a UAA stop codon. RC2 was prepared identically to RC1 with the exception that L1(Cy5) ribosomes were used in place of wild-type ribosomes.

Release complexes 1 and 2 (RC1 and RC2) were prepared in Tris-polymix buffer (50 mM Tris-OAc, pH$_{25°C}$=7.0, 100 mM KCl, 5 mM NH$_4$OAc, 0.5 mM Ca(OAc)$_2$, 0.1 mM EDTA, 10 mM 2-mercaptoethanol, 5 mM putrescine, and 1 mM spermidine), 5 mM Mg(OAc)$_2$, in three steps. In the first step, wild-type (RC1) or L1(Cy5) (RC2) ribosomes were incubated with initiation factors, fMet-tRNA$^{fMet}$ and an mRNA containing a 3'-biotinylated DNA oligonucleotide pre-annealed to its 5' end to enzymatically form an initiation complex. This initiation complex was then put through one elongation cycle by adding EF-Tu(GTP)Phe-(Cy3)tRNA$^{Phe}$ and EF-G(GTP), at which point ribosomes became stalled at the stop codon residing at the third codon position within the mRNA. The efficiency of this elongation step is approximately 95%, as deduced from a standard primer extension inhibition assay (Fei et al. 2008). Finally, the resulting ribosomal RCs were separated from free mRNA, translation factors, and aa-tRNAs by sucrose density gradient ultracentrifugation in Tris-polymix buffer at 20 mM Mg(OAc)$_2$, as previously described (Blanchard et al. 2004b).

Example 11

Single-Molecule Experiments

RCs assembled on a biotinylated mRNA were immobilized on the surface of a streptavidin-derivatized quartz flow cell and visualized with single-molecule resolution using a total internal reflection fluorescence microscope. RC surface immobilization strategy and lab-built total internal reflection fluorescence (TIRF) microscope are described in FIG. 10. Experiments were performed at room temperature in Tris-polymix buffer at 15 mM Mg(OAc)$_2$, supplemented with an oxygen-scavenging system (300 µg ml$^{-1}$ glucose oxidase, 40 µg ml$^{-1}$ catalase and 1% (w/v)(β-D-glucose). In addition, 1 mM 1,3,5,7-cyclooctatetraene (Aldrich) and p-nitrobenzyl alcohol (Fluka) was added to all buffers in order to quench a long-lived, non-fluorescent triplet state sampled by the Cy5 fluorophore. The oxygen-scavenging and triplet state quencher systems have no effect on the in vitro translation system used herein (Gonzalez et al. 2007; Blanchard et al. 2004b).

Quartz microscope slides were cleaned and subsequently derivatized with a mixture of polyethyleneglycol (PEG) and PEG-biotin in order to passivate the surface (Blanchard et al. 2004b). Just prior to data acquisition, slides were treated with streptavidin, allowing immobilization of ribosomal RCs bound to an mRNA with a 3'-biotinylated DNA oligonucleotide pre-annealed to its 5' end. smFRET data was collected with a wide-field, prism-based total internal reflection fluorescence microscope utilizing a 150 mW diode-pumped 532 nm laser (CrystaLaser) operating at 24 mW for Cy3 excitation, a 25 mW diode-pumped 643 nm laser (CrystaLaser) operating at 19 mW for direct Cy5 excitation, a Dual-View multi-channel imaging system (MAG Biosystems) for separation of Cy3 and Cy5 fluorescence emissions, and a back-thinned charge-coupled device camera (Cascade II, Princeton Instruments) with 2-pixel binning and 50 ms exposure time for detection. Single ribosomal RCs were identified by characteristic single-fluorophore fluorescence intensities as well as single-step fluorophore photobleaching.

Example 12

Selection of Single-Molecule FRET Trajectories

Raw intensity data was analyzed with the Metamorph software suite (Molecular Devices). For RF1-tRNA smFRET experiments with RC1, molecules exhibiting Cy5 fluorescence via FRET above a minimum threshold of 1000 Arbitrary Units in frame one of each steady-state movie, denoting an RF1-bound RC, were selected for further analysis. For L1-tRNA smFRET experiments with RC2, excited Cy5 was directly with the 643 nm laser in frame one, followed by excitation with the 532 nm laser in order to generate FRET. All molecules that exhibited Cy5 fluorescence via direct excitation in frame one were selected for further analysis. Acquired trajectories composed of a pair of Cy3 and Cy5 intensity versus time trajectories from single ribosomes, were then visually inspected. Trajectories exhibiting characteristic single-fluorophore fluorescence intensities and single-step fluorophore photobleaching were kept for further analysis. For all RRF and RF3(GDPNP) datasets, an automated selection algorithm was first utilized before visual inspection of the trajectories. This algorithm averages each trajectory over three data points, differentiates intensity with respect to time, and calculates the correlation coefficient for each Cy3/Cy5 pair. Trajectories with a negative correlation coefficient (anti-correlated) were kept for further analysis. Finally, all trajectories were required to last at least 0.5 seconds (i.e. 10 frames) before photobleaching of either fluorophore.

Cy3 and Cy5 fluorescence intensities were baseline corrected in each trajectory by generating one-dimensional Cy3 and Cy5 fluorescence intensity histograms from trajectories within each dataset, determining the intensity value of the most populated bin (which represents background noise intensity after fluorophore photobleaching), and then subtracting this value from all Cy3 and Cy5 intensity data points within every trajectory. Due to the imperfect performance of emission filters, the Cy3 signal bleed-through into the Cy5 channel was experimentally determined to be ~9%. The Cy5 intensity of each trajectory was corrected using this bleed-through coefficient. smFRET values for each Cy3/Cy5 data point were calculated using $I_{Cy5}/(I_{Cy3}+I_{Cy5})$, where $I_{Cy3}$ and $I_{Cy5}$ are the intensities of Cy3 and Cy5, respectively.

Example 13

RF1 and tRNA Conformational Dynamics During Stop-Codon Recognition and Polypeptide Release smFRET data on (Cy5)RF1 binding to TCs harboring fMet-Phe-(Cy3)tRNAPhe at the P site and either a UAA-U stop codon or an AAA-C sense codon at the A site was collected. Binding of the S167C, S192C and C257 (Cy5) RF1 variants to the RC generates steady state smFRET signals centered at 0.92, 0.78, and 0.78 FRET, respectively (FIGS. 11A-11C). The distances represented by these FRET values, 33 Å (S167C), 41 Å (S192C), and 41 Å (C257) are in accord with distances measured from the low-resolution (~6 Å) crystal structure of RF1 bound to a RC (26 Å, 49 Å, and 37 Å, respectively (FIG. 5). These smFRET signals are dependent on the presence of the UAA-U stop codon. Analogous experiments using the AAA-C sense codon yielded no observable smFRET signal for any of the three (Cy5)RF1 variants. Inspection of the individual smFRET versus time trajectories (FIGS. 11A-11C, second row) shows that the smFRET signal in all three (Cy5)RF1 variants is stable, limited only by photobleaching of the Cy3 or Cy5 fluorophores. This indicates that once pep-tRNA is deacylated by RF1, neither RF1 nor P-site tRNA undergo large-scale fluctuations in their relative orientations or their ribosome-bound conformations. This situation is in contrast to deacylation of pep-tRNA by peptidyl transfer to either aa-tRNA during elongation or puromycin; in these cases the tRNAs undergo large-scale conformational fluctuations between their classical and hybrid configurations (Kim et al. 2007; Munro et al. 2007; Blanchard et al. 2004b). Polypeptide release by RF1 is therefore the only deacylation event in protein synthesis that does not result in large-scale conformational fluctuations of the newly deacylated-tRNA at the P site.

Analogous experiments were performed in the presence of paromomycin, a neomycin-class aminoglycoside antibiotic that very strongly inhibits polypeptide release at a stop codon (Youngman et al. 2007; Youngman et al. 2006; Brown et al. 1993). Delivery of (Cy5)RF1 to TCs carrying a UAA-U stop codon in the A site in the presence of paromomycin yielded differential effects for the three (Cy5)RF1 variants (FIGS. 11D-11F). The S167C variant, reporting on the core domain of RF1, yielded a typical number of smFRET traces per field-of-view on the microscope. These traces predominantly sample a 0 FRET state with multiple transient excursions per trace to a FRET value centered at 0.86 FRET. This result is in agreement with that measured in the absence of paromomycin (0.92 FRET).

Dwell time analysis of the 0.86 FRET state yields an average lifetime of 0.59±0.09 sec. The C257 variant, reporting on the GGQ domain, yielded fewer smFRET traces per field-of-view. These traces predominantly sample a 0 FRET state, with much fewer transient excursions per trace to a FRET value centered at 0.73 FRET. This result is in agreement with that measured in the absence of paromomycin (0.78 FRET). Dwell time analysis of the 0.73 FRET state yields a lifetime of 0.38±0.02 sec, approximately twice as short as the lifetime of the S167C variant. The S192C variant, reporting on the PVT domain, yielded a very low number of smFRET traces, indicating that this is a rare event. The rare traces that are observed almost exclusively sample a 0 FRET state, with only single transient excursions per trace to a higher FRET value. Although the number of events is too low to accurately report an average FRET value or lifetime, the FRET values observed are consistent with the 0.78 FRET measured in the absence of paromomycin and the lifetime of these events is significantly shorter than 0.38±0.02 sec lifetime measured for the C257 variant. Analogous experiments using the AAA-C sense codon in the presence of paromomycin yielded no detectable smFRET signals for any of the three (Cy5)RF1 variants.

The stop-codon dependent observation of smFRET signals in the presence of paromomycin demonstrates that the ribosome and/or RF1 can recognize the presence of the highly efficient UAA-U stop codon at the A site even in the presence of paromomycin. These results demonstrate that the 0/0.86 FRET transitions of S167C report on the overall binding (0.86 FRET) and dissociation (0 FRET) of RF1 to the RC. In contrast, the 0/0.73 FRET and 0/0.78 FRET transitions of C257 and S192C report on docking (0.73 and 0.78 FRET) and undocking (0 FRET) of the GGQ and PVT domains of RF1 into the PTC and the DC, respectively.

Figure 12:
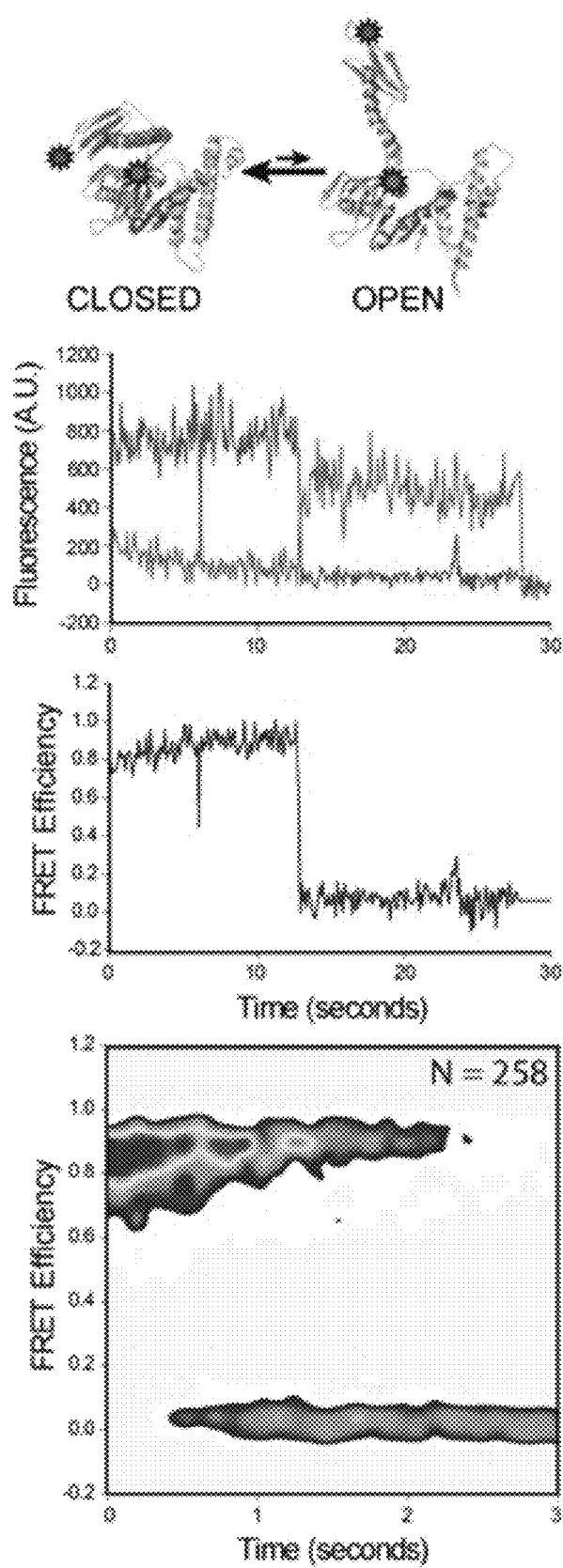
FIG. 12 shows steady-state intramolecular smFRET for free RF1. Representation of RF1 transitioning between the closed and open conformational states showing the approximate position of the fluorophores (Cy3 as a green star and Cy5 as a red star) (first row). The second-fourth rows are plotted as in FIG. 13.

Given that experiments using identically mutated and similarly derivatized RF1 variants have equal binding efficiencies of all three (Cy5)RF1 variants to the RC (Wilson et al. 2000), the relative lifetimes of the three domains (PVT<GGQ<core) of RF1 are consistent with a model in which paromomycin allows recognition of the stop codon by the ribosome and/or RF1, but blocks the PVT domain of RF1 from making the full set of interactions at the DC. While the ribosome and/or RF1 is able to undergo the necessary conformational changes that lead to placement of the GGQ domain of RF1 into the PTC, the full set of interactions between the GGQ domain and the PTC are also not made. This is direct evidence for allosteric coupling of stop codon-dependent RF1 interactions at the DC and stable docking of RF1 at PTC during termination. As the conformational change depicted in FIG. 12 is a candidate for allosteric signaling, this model will be tested by making mutations at the "hinge" within the core domain of RF1.

Failure of RF1 to make these stabilizing contacts at the PTC inhibits polypeptide release and ultimately leads to dissociation of RF1 from the RC (with most of the stabilizing contacts having been made only by the core domain of RF1). Further experiments using different stop codons, near-stop codons, and stop-codon contexts in the absence and presence of paromomycin can also be performed. Similar experiments can be performed to determine how paromomycin, and similar drugs, confer the ability of RF1 to distinguish between premature stop codons and natural stop codons using stop-codon context.

For example, steady-state smFRET experiments using mRNAs where the UAA-U stop codon (the highest efficiency stop codon in the highest efficiency stop-codon context) is mutated to UAG-C (the most inefficient RF1 stop codon in the most inefficient codon context) and UAU-C (the near-stop codon with the highest efficiency of RF1 misreading and premature termination) can be performed. These studies are performed in the presence and absence of paromomycin and the lifetimes of all three (Cy5)RF1 variants are measured under all conditions. This analysis produces a complete data set of lifetimes reporting the stabilities of the various domains of RF1 within these various stop codons and stop-codon contexts. This analysis will also demonstrate the effect paromomycin has on each of these lifetimes. These data will further develop the mechanistic model for stop codon recognition by the RC and/or RF1 and allosteric communication between the DC and the PTC during termination.

Eight mRNAs encoding both RF1 stop codons: UAA-X and UAG-X, where X is varied to all four nucleotide possibilities will be constructed to directly observe the effect of stop-codon context on paromomycin inhibition of peptide release. This analysis will demonstrate the mechanism through which paromomycin, and other aminoglycosides and small molecule drugs, inhibit polypeptide release specifically at premature stop codons.

Example 14

RF1 Remains Bound to RC post-Hydrolysis

Figure 13:
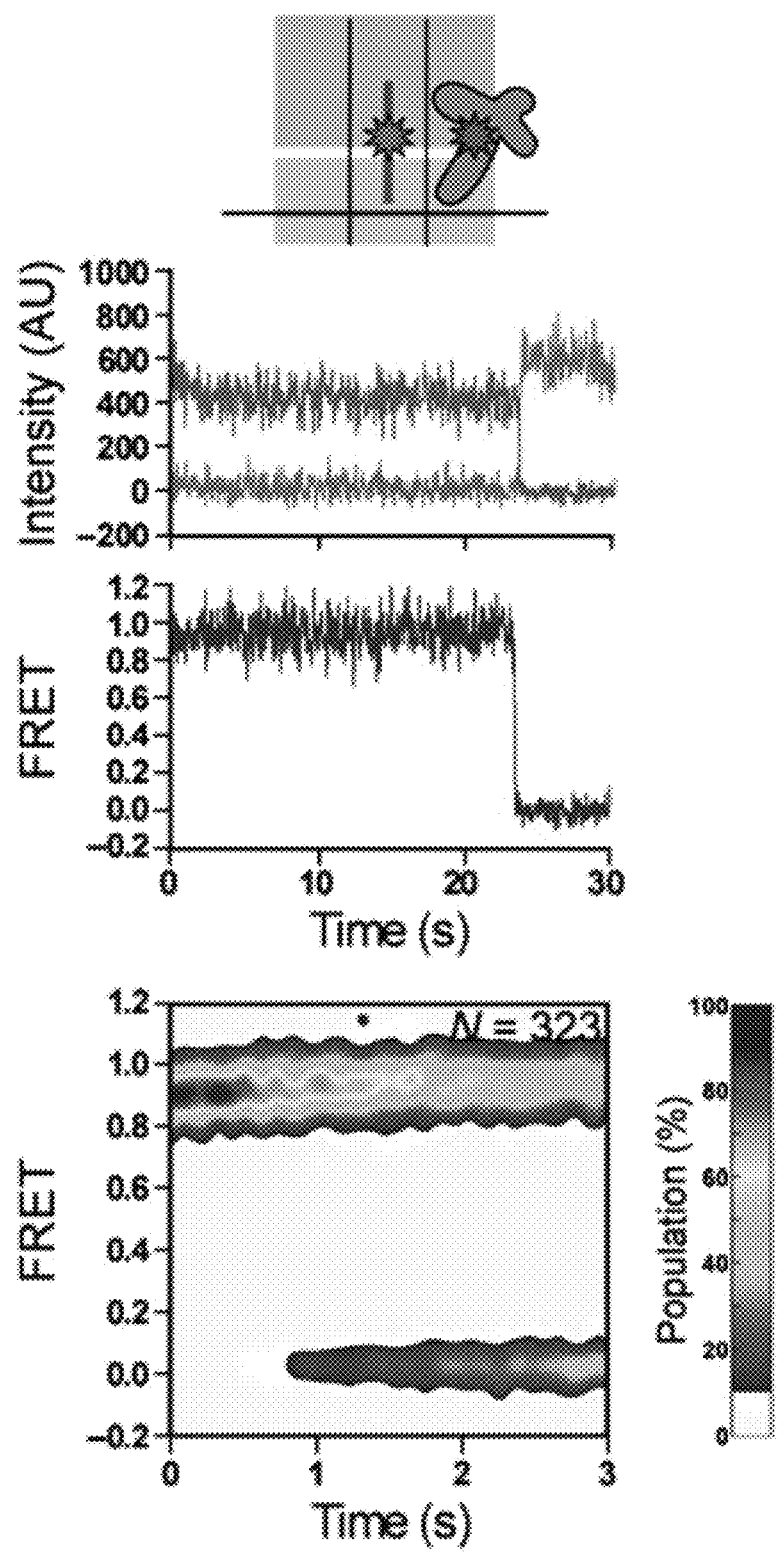
FIG. 13 shows that RF1 binds stably to a RC and prevents tRNA fluctuations. RC1 in the presence of 5 nM RF1(Cy5). A cartoon representation of RF1(Cy5) bound to RC1 is shown (first row). Representative Cy3 and Cy5 emission intensities are shown in green and red, respectively (second row). The corresponding smFRET trace, $I_{Cy5}/(I_{Cy3}+I_{Cy5})$, is shown in blue (third row). Contour plots of the time evolution of population FRET (fourth row) are generated by superimposing the first three seconds of individual smFRET time trajectories, binning the data into 20 FRET bins and 30 time bins, normalizing the resulting data to the most populated bin in the plot, and scaling the z-axis as shown in the color bar. "N" indicates the number of traces making up the contour plot.

Incubation of surface-immobilized RC1 with 5 nM RF1 (Cy5) generates steady-state smFRET versus time trajectories that sample a single FRET state centered at 0.94±0.01 FRET (FIG. 13). Although the smFRET studies described herein focus on relative distance changes, the observed 0.94 FRET value, corresponding to a distance of ~32-38 Å (assuming $R_0$=50-60 Å) (Holing et al. 2004; Bastiaens et al.

Figure 14:
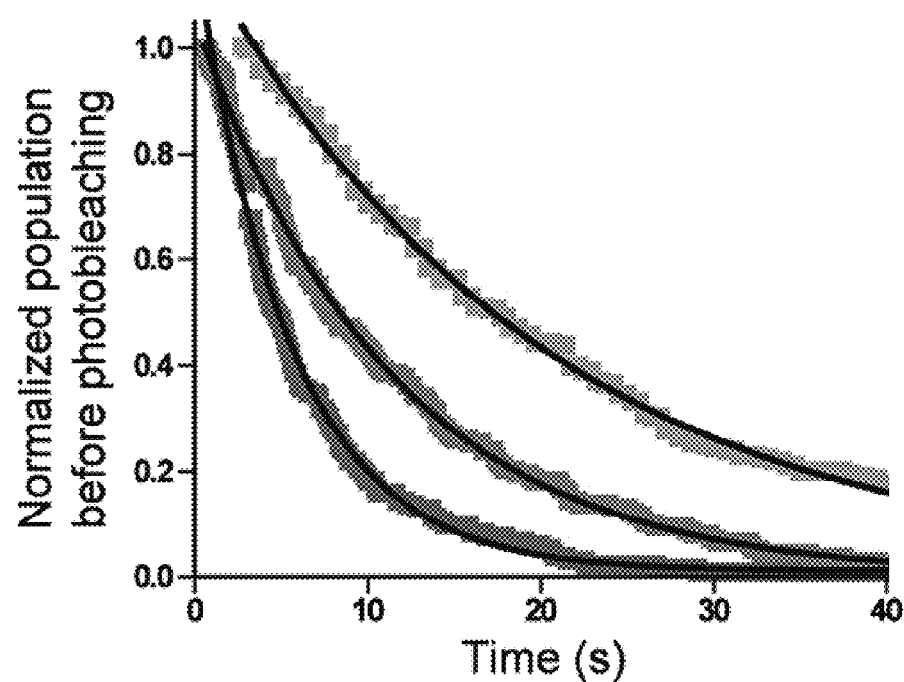
FIG. 14 shows an analysis of photobleaching rate for smFRET$_{RF1-tRNA}$ signal. Data was recorded using 532 nm laser excitation powers of 24 mW (red), 12 mW (green), or 24 mW chopped laser pulses which illuminated the sample for 50 ms every 250 ms (blue). After manually determining the length of every smFRET trajectory before photobleaching of either Cy3 or Cy5, one-dimensional histograms of trajectory length were plotted. Because all analyzed smFRET trajectories were required to last longer than 10 frames, the first 10 frames of data from the histograms were removed before fitting the data to single exponential decays (black lines) of the form A×exp−(x−x$_0$/τ)+y$_0$, with x$_0$ manually set to 0.55 seconds (24 mW and 12 mW) or 2.68 seconds (24 mW with laser chopping). The following parameters were obtained: y$_0$=0.0097, A=1.061, τ=5.51±0.02 s (24 mW, red); y$_0$=−0.001, A=1.005, τ=11.22±0.05 s (12 mW, green); and y$_0$=0.0063, A=1.032, τ=19.46±0.07 s (24 mW with laser chopping, blue). Taking the inverse of each lifetime yielded the following rates for the loss of fluorescence signal: 0.1814±0.0008 s$^{-1}$, 0.0892±0.0004 s$^{-1}$, and 0.0514±0.0002 s$^{-1}$, respectively. The R$^2$ of all fits was greater than 0.99. The dependence of the rate of loss of the fluorescence signal on laser excitation power and excitation time demonstrates that loss of fluorescence is due to photobleaching rather than dissociation of RF1(Cy5) from RC1.

1996), is in agreement with the about 23 Å distance measured between the points of attachment of the fluorophores in an X-ray crystal structure of RF1 bound to an RC (Laurberg et al. 2008). As a control, incubation of 5 nM RF1(Cy5) with an analogous complex containing a sense codon (AAA) at the A site yielded no detectable smFRET signal. Inspection of individual trajectories (FIG. 13) shows that the 0.94 FRET state is long-lived, with a lifetime limited only by fluorophore photobleaching (FIG. 14). This result demonstrates that after hydrolysis, RF1 remains stably bound to RC1. This result is consistent with previous biochemical studies (Zavialov et al. 2002). The 0.94 FRET state undergoes no detectable fluctuations to additional FRET states within the time resolution use din this analysis (20 frames s$^{-1}$). Given the large displacement (~40 Å) of the central-fold domain, or elbow, of the P-site tRNA during the classical→hybrid transition (Agirrezabala et al. 2008), this shows that deacylation of P-site tRNA by RF1 does not result in tRNA movements between the classical and hybrid binding configurations. This result is in contrast to the analogous situation in a pretranslocation elongation complex (Kim et al. 2007; Munro et al. 2007; Blanchard et al. 2004b). This result does not exclude the possibility that tRNA movements are not result in an observable FRET change.

Example 15

Dwell-Time Analyses

Standard procedures for data analysis are schematized in FIG. 15. Individual smFRET traces can be analyzed to obtain the dwell times prior to undergoing a transition. For example, the cartoon smFRET trace shown in FIG. 15A depicts a number of dwell times encompassing RF1 binding (t1), establishment of the RF1-tRNA interaction (t2), a number of sampled intermediate states (t3, t4), steady-state fluctuations between smFRET states (t5, t6), and, assuming RF1 dissociation is faster than dye photobleaching, possibly a dwell time for dissociation of the RF1 (t7). As an example, t5 and t6 would correspond to the GS1-GS2 dynamic equilibrium, which is modulated by RF1, RF3, and RRF during termination and recycling (FIG. 16). Initial analysis of the number of FRET states and populations sampled in the individual traces is obtained by plotting a 1D FRET population histogram or the time evolution of the population FRET (FIG. 15B). A key feature of the time evolution of the population FRET plot is that the data has been post-synchronized.

Individual RF1s will bind a RC with a unique dwell time (t1); this leads to a marked heterogeneity in the onset of FRET among all the traces. By post-synchronizing the data to the first detected FRET value, the heterogeneity in t1 can be eliminated and the time evolution of the population FRET upon RF1 binding, as shown in the idealized plot in FIG. 15B, can be analyzed. This ability to post-synchronize the data set to any FRET value of interest is an attribute of single-molecule analysis and is a powerful way of synchronizing a population of molecules to a particular state and directly observing their behavior upon transitioning out of that state.

Hidden Markov analysis can then be used to generate idealized smFRET traces from the raw smFRET traces (Fei et al. 2008; Qin et al. 2000a; Qin et al. 2000b) (FIG. 15C). Hidden Markov analysis eliminates user bias in the data analysis by providing a statistically-based method for determining the number of FRET states that is best represented by the raw traces. The idealized traces output by the hidden Markov analysis are then used to generate histograms of dwell times of individual FRET states which are exponentially fit in order to determine the lifetime of each state (FIG. 15D). Alternatively, hidden Markov analysis can also be used to directly provide a complete model, reporting not just the number of states, but also the average transition frequencies and transition rates that best describe the acquired data. Regardless, the data analysis collectively provides the number of conformational states reported by the recorded smFRET signal as well as the transition frequencies and transition rates between these conformational states. Specific examples of the successful application of all of the above general data analysis methods to studies of the conformational dynamics of protein synthesis can be found in previously published literature (Fei et al. 2008; Gonzalez et al. 2007; Dorywalska et al. 2005; Blanchard et al. 2000a; Blanchard et al. 2000b).

The rates of GS1→GS2 ($k_{GS1 \to GS2}$) and GS2→GS1 ($k_{GS2 \to GS1}$) transitions for each dataset were determined as follows. Individual, fluctuating smFRET$_{L1-tRNA}$ trajectories were fitted to a hidden Markov model using the HaMMy software suite (McKinney et al. 2006) with an initial guess of 5 states. The resulting idealized trajectories were filtered such that transitions occurring with either a change in FRET of less than 0.1 or lasting only a single frame were discarded. Dwell times spent in GS1 were then extracted before undergoing a transition to GS2 and dwell times spent in GS2 before undergoing a transition to GS1 from the idealized smFRET trajectories as follows.

For each dataset, one-dimensional smFRET histograms were plotted from the first 0.5 seconds (i.e. 10 frames) of all traces and fit with two Gaussian distributions, centered at 0.16 for GS1 and 0.76 for GS2, using Origin 7.0. Thresholds corresponding to the GS1 and GS2 FRET states were then set using the full width at half height of the Gaussian distributions. One-dimensional histograms of the time spent in GS1 and GS2 before undergoing a transition were plotted, and the corresponding GS1 and GS2 lifetimes were determined by fitting each histogram to a single-exponential decay. Dwell times resulting from the first and last transitions within each trajectory were not included in this analysis due to the arbitrary onset of data collection and the stochastic nature of the photobleaching event. The thresholds were subsequently increased and then decreased by 0.03 FRET (Fei et al. 2008), and the analyses were repeated in order to test the sensitivity of the calculated lifetimes to the choice of thresholds. The sensitivity to threshold values were found to be minimal, and the average lifetime value for each dataset was determined using the data obtained from these three sets of thresholds. Finally, $k_{GS1 \to GS2}$ and $k_{GS2 \to GS1}$ were calculated by taking the inverse of the GS1 and GS2 lifetimes, respectively, and applying corrections to account for premature truncation of fluctuating trajectories caused by photobleaching and the finite nature of the observation time.

Example 16

Corrections to $k_{GS1 \to GS2}$ and $k_{GS2 \to GS1}$

Measured rates for GS1→GS2 ($k_{GS1 \to GS2}$) and GS2→GS1 ($k_{GS2 \to GS1}$) transitions are systematically overestimated because all fluctuating smFRET trajectories for L1 stalk-tRNA FRET signal were prematurely truncated by either Cy3 or Cy5 photobleaching or, more rarely, by the length of observation time (60 seconds) (Bartley et al. 2003).

To account for the rates of photobleaching and the limited observation time, a uniform correction was applied to all observed values for $k_{GS1 \to GS2,obs}$ and $k_{GS2 \to GS1,obs}$ using the following equations (Bartley et al. 2003):

$$k_{GS1 \to GS2} = k_{GS1 \to GS2,obs} - k_{photobleach,GS1} - 1/T$$

$$k_{GS2 \to GS1} = k_{GS2 \to GS1,obs} - k_{photobleach,GS2} - 1/T$$

where $k_{photobleach,GS1}$ and $k_{photobleach,GS2}$ are the photobleaching rates from the FRET states corresponding to GS1 and GS2, respectively, and T is the observation time (60 seconds). $k_{photobleach,GS1}$ was measured by averaging the rate of photobleaching for stable 0.16 smFRET trajectories from the following datasets: $RC2_{Pmn}$+RF1, $RC2_{RF1}$, $RC2_{RF1}$+RF3(nucleotide free), and $RC2_{RF1}$+RF3(GDP). $k_{photobleach,GS2}$ was measured by averaging the rate of photobleaching for stable 0.76 FRET trajectories from the following datasets: $RC2_{Pmn}$+50 µM RRF, $RC2_{Pmn}$+ 1 µM RF3(GDPNP), and RC2p.+5 µM RF3(GDPNP). $k_{photobleach,GS1}$ and $k_{photobleach,GS2}$ was determined to be 0.05±0.01 s$^{-1}$ and 0.29±0.03 s$^{-1}$, respectively. All values for $k_{GS1 \to GS2}$ and $k_{GS2 \to GS1}$ given in the text and figures correspond to corrected rates.

Example 17

RF1 and RF3 Direct the GS1-GS2 Equilibrium During Termination

As described herein, RF1-tRNA smFRET signals reveal stable FRET states, indicating that neither the newly deacylated-tRNA nor RF1 undergo large-scale fluctuations in their relative orientations or ribosome-bound conformations. Classical-hybrid tRNA equilibrium is directly coupled to the GS1-GS2 equilibrium during elongation (Fei et al. 2008). To determine whether RF1 also has an effect on the GS1-GS2 equilibrium, TCs were prepared using Cy5-labeled ribosomes (labeled at ribosomal protein L1 within the L1 stalk of the 50S subunit) (Fei et al. 2008) and fMet-Phe-(Cy3) tRNAPhe, in order to test the effect of RF1 on the GS1-GS2 equilibrium. In accord with the RF1-tRNA smFRET data, deacylation of pep-tRNA by RF1 blocks the GS1-to-GS2 transition that is typically observed upon deacylation of pep-tRNA by aa-tRNA or puromycin (FIGS. 16A and 16B) (Fei et al. 2008). Binding of RF1 to TCs that have been deacylated with puromycin and have established the GS1-GS2 equilibrium leads to RF1-dependent stabilization of GS1 and block the GS1-to-GS2 transition. Because the GS1-to-GS2 transition is a spontaneous property of the ribosome that is triggered upon deacylation of P-site pep-tRNA and driven solely by thermal fluctuations (Fei et al. 2008), blocking of the intrinsic GS1-to-GS2 transition by RF1 can be an important mechanistic feature of RF3-catalyzed dissociation of RF1 from the RC. To this end, the effect of RF3 binding to a post-hydrolysis RC in the presence of a GDP as well as a non-hydrolyzable GTP analog, GDPNP was examined. RF3 binding to a post-hydrolysis RF1-containing RC in the presence of GDP yields data that is indistinguishable from that observed for RF1 alone (FIG. 16B).

Relative to RF1 binding, RF3 binding in the presence of GDPNP has an orthogonal effect on the GS1-GS2 equilibrium, strongly stabilizing the GS2 and blocking the GS2-to-GS1 transition (FIG. 16C). These results show that RF3 in the GDP form binds to GS1 carrying a deacylated-tRNA at the P site and RF1 at the A site. Upon GDP/GTP exchange, RF3 destabilizes the binding of RF1 to the A site enough such that the GS1-to-GS2 transition is no longer effectively blocked by RF1 and is allowed to proceed. The GS1-to-GS2 transition further destabilizes RF1 binding to the ribosome and leads to its dissociation. Upon GTP hydrolysis RF3 (GDP) has low affinity for GS2 and dissociates from the ribosome thereby establishing the GS1-GS2 equilibrium in the PoTC substrate that will now be recognized by RRF.

Example 18

RF1 Blocks GS1→GS2 Transitions within a Post-Hydrolysis RC

To directly investigate the effect of RF1 on conformational dynamics of both the P-site tRNA and L1 stalk, the GS1⇌GS2 equilibrium was monitored using the smFRET$_{L1-tRNA}$ signal within RC2. Prior to RF1-catalyzed peptide release, the majority of RC2 trajectories (~87%) sample a single FRET state centered at 0.16±0.01 FRET (FIG. 17A). This result is consistent with results observed in posttranslocation elongation complexes (Fei et al. 2008), which also carry a peptidyl-tRNA at the P site and an empty A site. Of the remaining trajectories, 1% sample a single FRET state centered at 0.76±0.01 FRET, reporting on GS2, and 12% exhibit fluctuations between 0.16 and 0.76 FRET; these latter two subpopulations represent ribosomes whose P-site peptidyl-tRNA was prematurely deacylated during RC2 preparation, thereby enabling transitions to GS2.

Addition of 1 µM RF1 to surface-immobilized RC2 generates no substantial change in the smFRET$_{L1-tRNA}$ signal (FIG. 17B), demonstrating that RF1-catalyzed deacylation of P-site peptidyl-tRNA via hydrolysis does not result in GS1→GS2 transitions. This result is in agreement with smFRET$_{RF1-tRNA}$ data. A slight shift in the relative occupancies of smFRET subpopulations was observed such that 98% of the trajectories now sample stable 0.16 FRET, compared to 87% in the absence of RF1 (the remaining 2% of trajectories show rare fluctuations to 0.76 FRET). Thus, even fluctuating smFRET trajectories resulting from the premature deacylation of peptidyl-tRNA during RC2 preparation were converted to stable 0.16 smFRET trajectories in the presence of RF1. This result shows that RF1 binding alone can block GS1→GS2 transitions independently of the actual deacylation event.

To confirm these results, peptidyl-tRNA was deacetylated by pre-treating RC2 with puromycin (RC2$_{Pmn}$). The majority of RC2$_{Pmn}$ trajectories (~63%) fluctuate between 0.16 and 0.76 FRET (FIG. 17C), reporting on spontaneous and reversible transitions between GS1 and GS2. The remaining trajectories either failed to undergo the puromycin reaction or exhibited fluorophore photobleaching directly from 0.16 or 0.76 FRET before undergoing a fluctuation. The latter observation indicates that GS1→GS2 and GS2→GS1 transition rates extracted from dwell-time analysis of these data will be slightly overestimated due to the premature truncation of the trajectories. After correcting for photobleaching kinetics and the finite experimental observation time (Munro et al. 2007), dwell-time analysis of RC2$_{Pmn}$ data yielded GS1→GS2 and GS2→GS1 transition rates ($k_{GS1 \to GS2}$ and $k_{GS2 \to GS1}$) of 0.52±0.03 s$^{-1}$ and 1.36±0.03 s$^{-1}$, respectively (FIG. 18).

Addition of 1 µM RF1 to surface-immobilized RC2$_{Pmn}$ strongly perturbs the GS1⇌GS2 equilibrium (FIG. 17D), such that the majority (85%) of the trajectories now exhibit stable 0.16 FRET. Addition of RF1 to RC2$_{Pmn}$ generates an smFRET$_{L1-tRNA}$ signal that is virtually indistinguishable from that observed for non-puromycin reacted RC2 in the absence or presence of RF1 (compare FIG. 17D to FIGS. 17A, 17B). In all three cases, measurement of the actual lifetime spent in the 0.16 FRET state is limited by fluorophore photobleaching, demonstrating that intermolecular RF1-ribosome and/or intramolecular ribosome-ribosome interactions, established upon tight binding of RF1 to the post-hydrolysis RC, block the GS1→GS2 transitions that would otherwise occur spontaneously in a ribosomal complex carrying a deacylated tRNA at the P site. Thus, whereas deacylation of P-site tRNA via peptidyltransfer to A-site aa-tRNA shifts the GS1⇋GS2 equilibrium towards GS2 in anticipation of EF-G (Fei et al. 2008), deacylation of P-site tRNA via RF1-mediated hydrolysis locks the RC in GS1 in anticipation of RF3.

Example 19

RF1 Domain 1 is Expendable for Blocking GS1→GS2 Transitions

Figure 7:
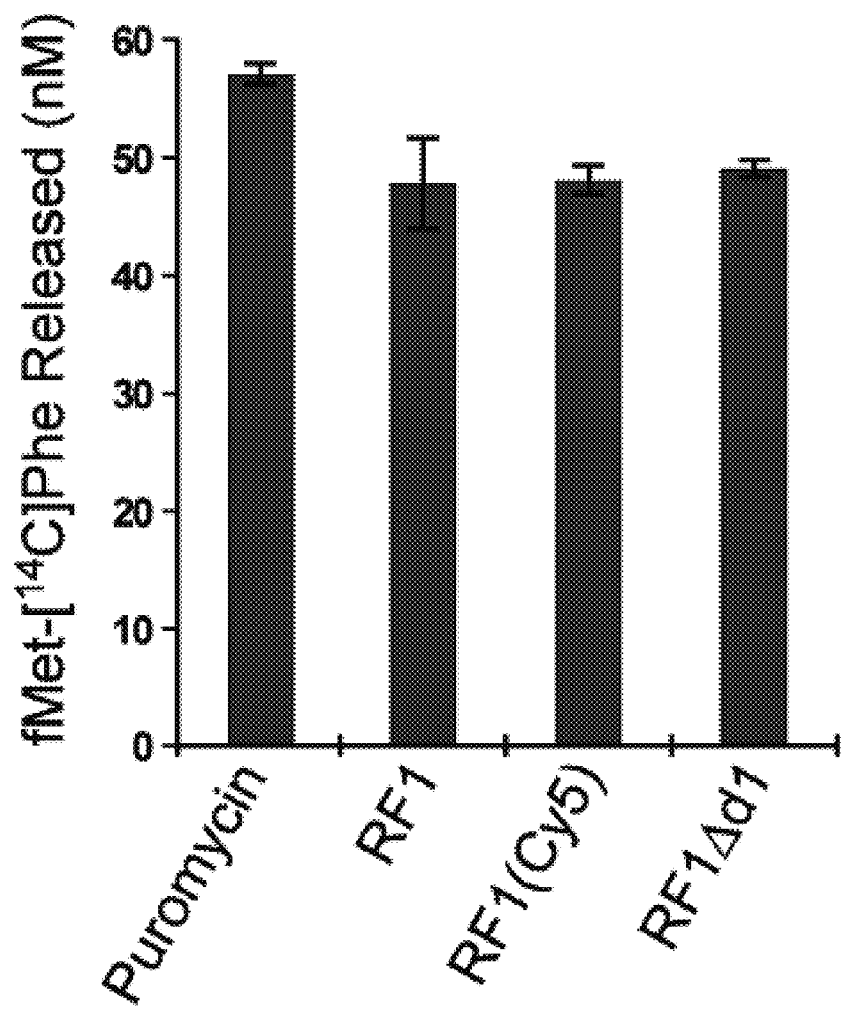
FIG. 7 shows a RF1 activity assay. RCs (~58 nM) carrying a stop codon (UAA) at the A site and fMet-[$^{14}$C] Phe-tRNA$^{Phe}$ in the P site were reacted with puromycin (100 μM) or the RF1 construct shown (100 nM) for 1 minute at 37° C. No RF1-catalyzed peptide release was detected in identical experiments using a RC with a sense codon (AAA) at the A site. Error bars represent the standard deviation from three independent experiments.

RF1 domains 2-4 occupy the A site in a manner that is spatially analogous to a classically-bound tRNA (Laurberg et al. 2008; Rawat et al. 2006; Petry et al. 2005), whereas domain 1 protrudes out of the A site, spanning the gap between the "beak" domain of the 30S subunit and the L11 region of the 50S subunit (Laurberg et al. 2008). Direct contacts between RF1 domain 1 and both the 30S and 50S subunit have been observed crystallographically (Laurberg et al. 2008; Petry et al. 2005). To determine whether domain 1-ribosome interactions provide the molecular basis for RF1's ability to block GS1→GS2 transitions, an RF1 domain 1 deletion mutant (RF1Δd1) was prepared (Mora et al. 2003). RF1Δd1(Cy5) was generated in the same manner as full-length RF1(Cy5). Biochemical testing confirmed that RF1 Δd1 and RF1Δd1(Cy5) can catalyze stop codon-dependent peptide release. This activity was albeit slightly lower activity relative to full-length RF1 (Mora et al. 2003) (FIG. 7).

Shown in FIG. 19 are results of RC1, RC2, and $RC2_{Pmn}$ experiments analogous to those reported in FIG. 13 and FIG. 17, but with RF1Δd1 in place of full-length RF1. The results are virtually indistinguishable. The $smFRET_{RF1\Delta d1-tRNA}$ signal, centered at 0.93±0.02 FRET, is stable and shows no evidence of fluctuations (FIG. 19A), showing that, like full-length RF1, RF1Δd1 remains stably bound to the post-hydrolysis RC and prevents tRNA movements. Despite the absence of domain 1-ribosome interactions, RF1Δd1 blocks GS1→G52 transitions upon hydrolysis (FIG. 19B) and independently of the origin of the deacylation event (FIG. 19C). These results show that RF1's ability to lock the RC in GS1 does not require domain 1.

Example 20

GTP Binding to RC-Bound RF3 Triggers the GS1→GS2 Transition

Figure 21:
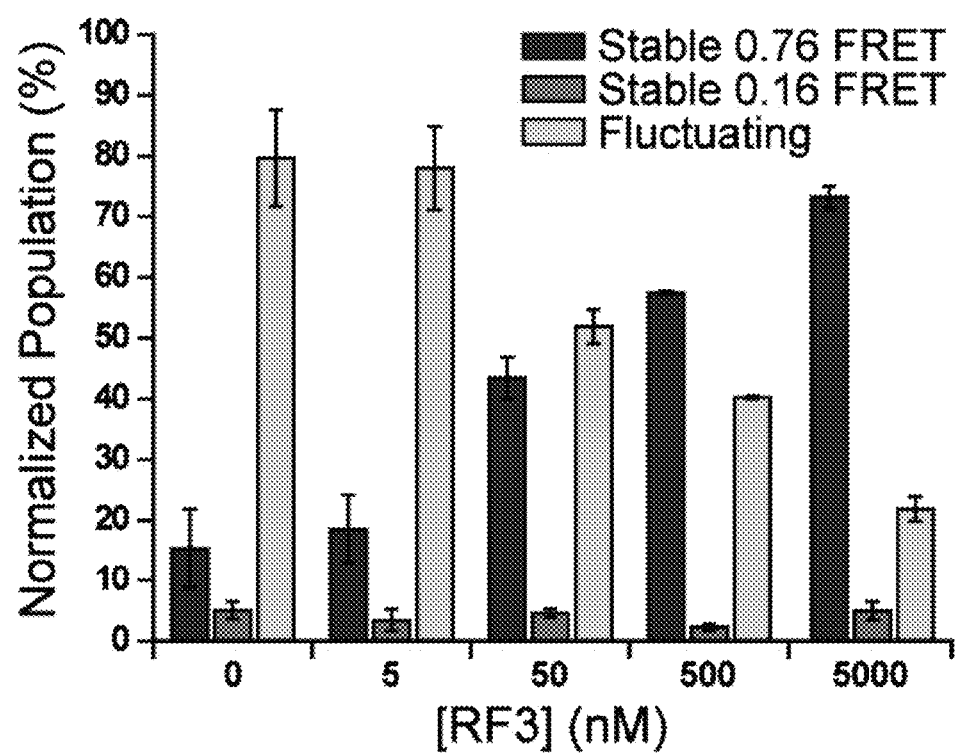
FIG. 21 shows subpopulation analysis of RC2$_{Pmn}$+RF3 (GDPNP) titration. Data from RC2$_{Pmn}$ alone or RC2$_{Pmn}$ was collected in the presence of 1 mM GDPNP and the concentration of RF3 shown, and grouped resulting smFRET trajectories into one of three subpopulations: stable 0.76 FRET (GS2; dark blue), stable 0.16 FRET (GS1; medium blue), or fluctuating trajectories showing transitions between 0.76 and 0.16 FRET (light blue). As RF3 concentration increases, the relative occupancy of the fluctuating subpopulation decreases as progressively more trajectories exhibit stable 0.76 FRET, corresponding to RF3(GDPNP)-bound RCs. Error bars represent the standard deviation from multiple datasets (0 nM RF3) or after splitting each dataset into three equal parts and analyzing subpopulations for each part separately.

Puromycin-reacted RC bound to RF3(GDPNP, a non-hydrolyzable GTP analog) was a GS2-like conformation (Gao et al. 2007a). This structure provides a snapshot of the post-hydrolysis RC after RF1 dissociation but before GTP hydrolysis by RF3. The RF1 results described herein show that the target for RF3-mediated RF1 dissociation is a post-hydrolysis, RF1-bound RC locked in GS1. Prior to investigating the dynamics of an analogously prepared RC, purified RF3 was confirmed to exhibit guanine nucleotide-dependent biochemical activity (Zavialov et al. 2001) (FIG. 8) and 1 μM RF3(GDPNP) was added to surface-immobilized $RC2_{Pmn}$ The results show that RF3(GDPNP) alters the relative occupancies of subpopulations observed with $RC2_{Pmn}$ such that the majority (73%) of smFRET trajectories remain stably centered at 0.76 FRET (FIG. 20A). Unlike RF1, the GTP-bound form of RF3 locks a post-hydrolysis RC into GS2. Dwell-time analysis of the fluctuating subpopulation of smFRET trajectories (22%) revealed kinetics that were consistent with those of isolated $RC2_{Pmn}$ indicating that this subpopulation of $RC2_{Pmn}$ does not bind RF3 (GDPNP) under the conditions used in this analysis. Consistent with these results, increasing the RF3(GDPNP) concentration causes a decrease in the occupancy of the fluctuating subpopulation while $k_{GS1\rightarrow GS2}$ and $k_{GS2\rightarrow GS1}$ remain relatively constant (FIG. 21).

The smFRET data show that the GS1→GS2 transition occurs at a point during or after binding of RF3(GDP) to the post-hydrolysis, RF1-bound RC, but before hydrolysis of GTP by RF3. To determine the GS1→GS2 transition within the termination pathway, steady-state smFRET experiments were performed by incubating surface-immobilized RC2 with 1 μM RF1 to generate $RC2_{RF1}$ and subsequently incubating $RC2_{RF1}$ with 1 μM RF3 in the absence or presence of the specified guanine nucleotide and 1 μM RF1. Biochemical data show that nucleotide-free RF3 forms a high-affinity complex with the RF1-bound RC (Zavialov et al. 2001) (FIG. 8), and the ability of binding of RF3(GDP) or nucleotide-free RF3 to $RC2_{RF1}$ to activate the GS1→GS2 transition was examined. Both of these experiments generate steady-state smFRET data that is indistinguishable from data collected with $RC2_{RF1}$ alone (compare FIG. 20B, 20C with FIG. 17B), indicating that neither binding of RF3(GDP) to $RC2_{RF1}$, $RC2_{RF1}$-catalyzed exchange of GDP for exogenous GDP on RF3, nor the nucleotide-free RF3 intermediate elicit or involve the GS1→GS2 transition.

Figure 22:
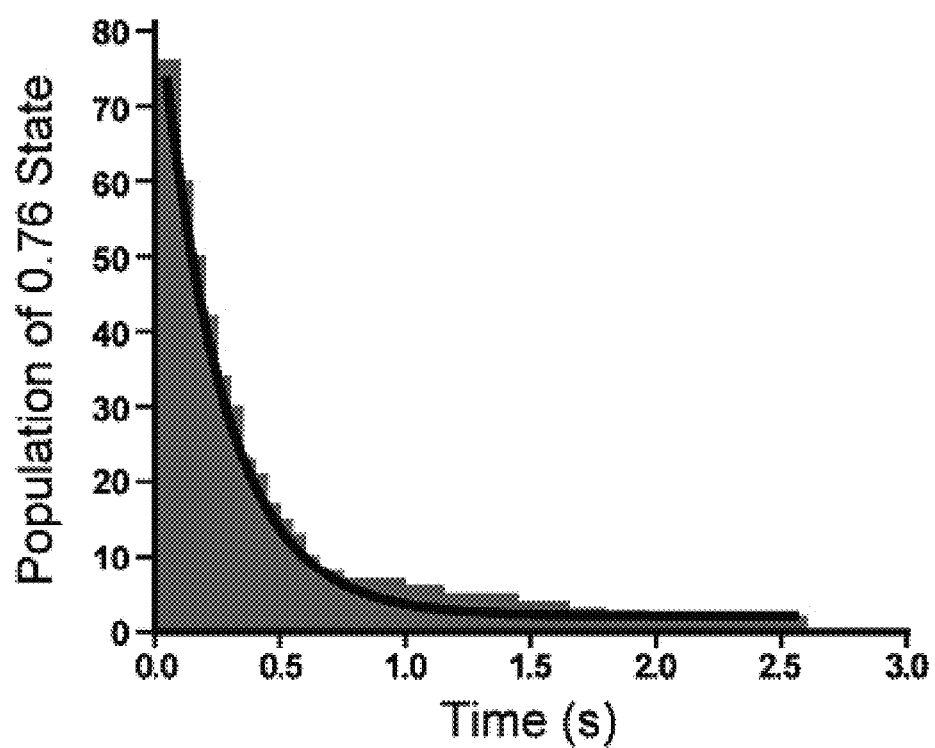
FIG. 22 shows kinetic analysis of k$_{GS2→GS1}$ for RC2$_{RF1}$+RF3(GDP)+GTP. The dataset was split into three equal parts, and independently fit one-dimensional histograms of time spent in GS2 for each third of the dataset with a single-exponential decay (black line) of the form A×exp−(x/τ)+y$_0$. The following parameters were obtained from a representative third: y$_0$=2.1, A=87, τ=0.249±0.005 s (R$^2$=0.99), yielding k$_{GS2→GS1}$=3.71±0.08 s$^{-1}$ after correcting for photobleaching rate and the length of observation time. The final value of k$_{GS2→GS1}$=3.7±0.6 s$^{-1}$ is the average and standard deviation of independent fitting and analysis of each third of the dataset.

The addition of RF3(GDP) to surface-immobilized $RC2_{RF1}$ was examined in the presence of a mixture of 10 μM GDP and 1 mM GTP. Because it was performed with saturating 1 μM RF1, this experiment is expected to yield a continuously recycling termination reaction (FIG. 2B), in which binding of GTP to RC-bound RF3 catalyzes RF1 dissociation and subsequent GTP hydrolysis leads to RF3 (GDP) dissociation (Zavialov et al. 2001), thereby enabling RF1 rebinding and a new round of RF3-mediated RF1 dissociation. Individual smFRET trajectories exhibit clear evidence of one or more excursions to GS2 (FIG. 20D), demonstrating that the GS1→GS2 transition occurs exclusively upon binding of GTP to RC-bound RF3. Because the transitions to GS2 are short-lived, events may be missed (for example, excursions to GS2 that are much shorter than the time resolution used herein). Thus, dwell-time analysis provides a lower limit of $k_{GS2\rightarrow GS1} \geq 3.7\pm0.6$ $s^{-1}$ (FIG. 22), which is almost 3-fold faster than $k_{GS2\rightarrow GS1}$ for $RC2_{Pmn}$ in the absence of RF1, RF3, and guanine nucleotide (1.36±0.03 $s^{-1}$). This result shows that hydrolysis of GTP, dissociation of RF3(GDP), and/or rebinding of RF1 can promote the GS2→GS1 transition.

Example 21

RRF Fine-Tunes the GS1⇋GS2 Equilibrium within a PoTC

Figure 23:
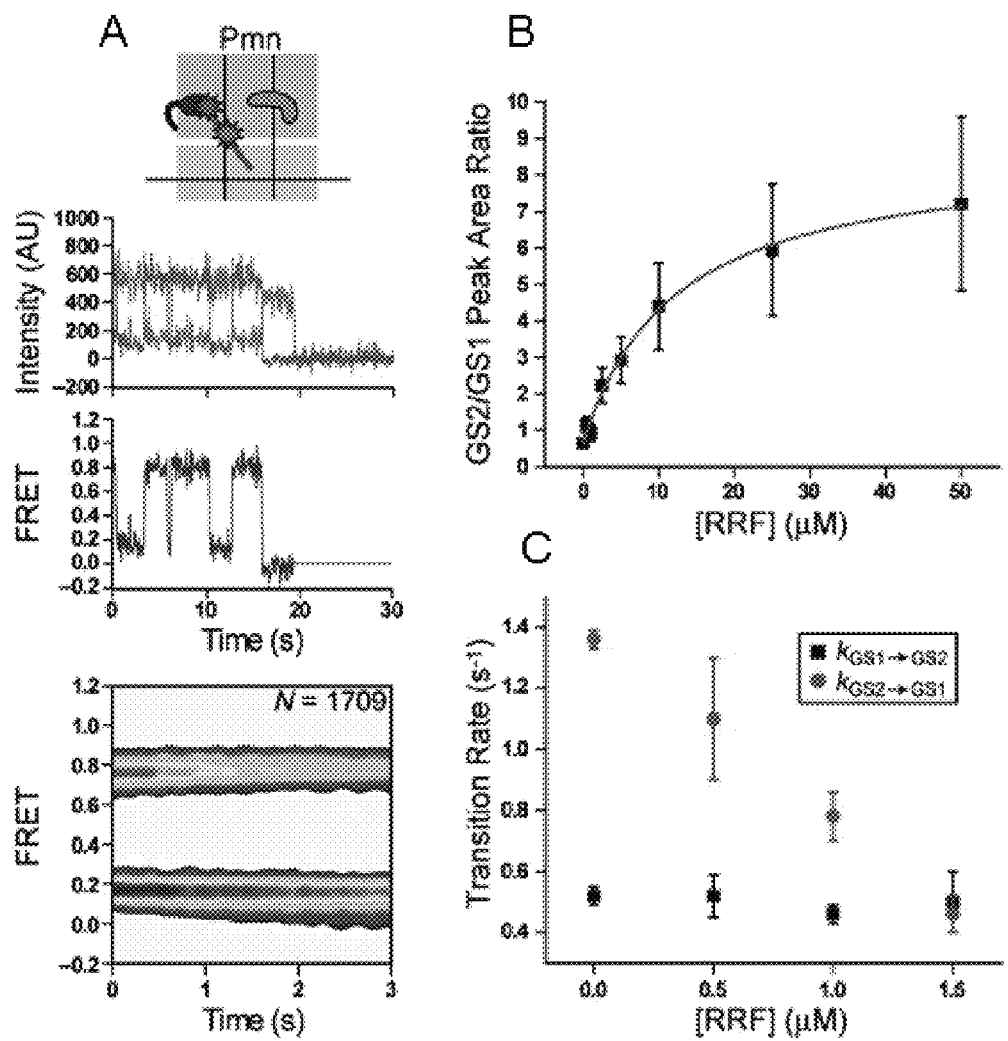
FIG. 23 shows that RRF preferentially binds GS2 and competes with GS2→GS1 transitions within a fluctuating PoTC.

Puromycin-reacted RCs yield PoTCs serve as natural substrates for RRF- and EF-G-catalyzed ribosome recycling (Karimi et al. 1999). After confirming the activity of purified RRF in a standard ribosome splitting assay (FIG. 9), RC2$_{Pmn}$ was used as a model PoTC with which to investigate the effect of RRF binding on the GS1⇆GS2 equilibrium. In contrast to RF1 and RF3, RRF was observed to have only modest effects on the GS1⇆GS2 equilibrium and slightly stabilizing GS2 (FIG. 23A). Even with a large excess of RRF over surface-immobilized RC2$_{Pmn}$, the relative occupancies of smFRET subpopulations remained almost unchanged relative to RC2$_{Pmn}$ As the RRF concentration was increased, the dwell time spent in the 0.76 FRET state was extended, ultimately leading to a decrease in the occupancy of the fluctuating subpopulation and an increase in occupancy of the stable 0.76 FRET subpopulation as the rate of photobleaching from the 0.76 FRET state began to limit observations of fluctuations to 0.16 FRET. However, even at concentrations as high as 50 µM RRF, individual smFRET trajectories still exhibited rare fluctuations to 0.16 FRET.

Figure 24:
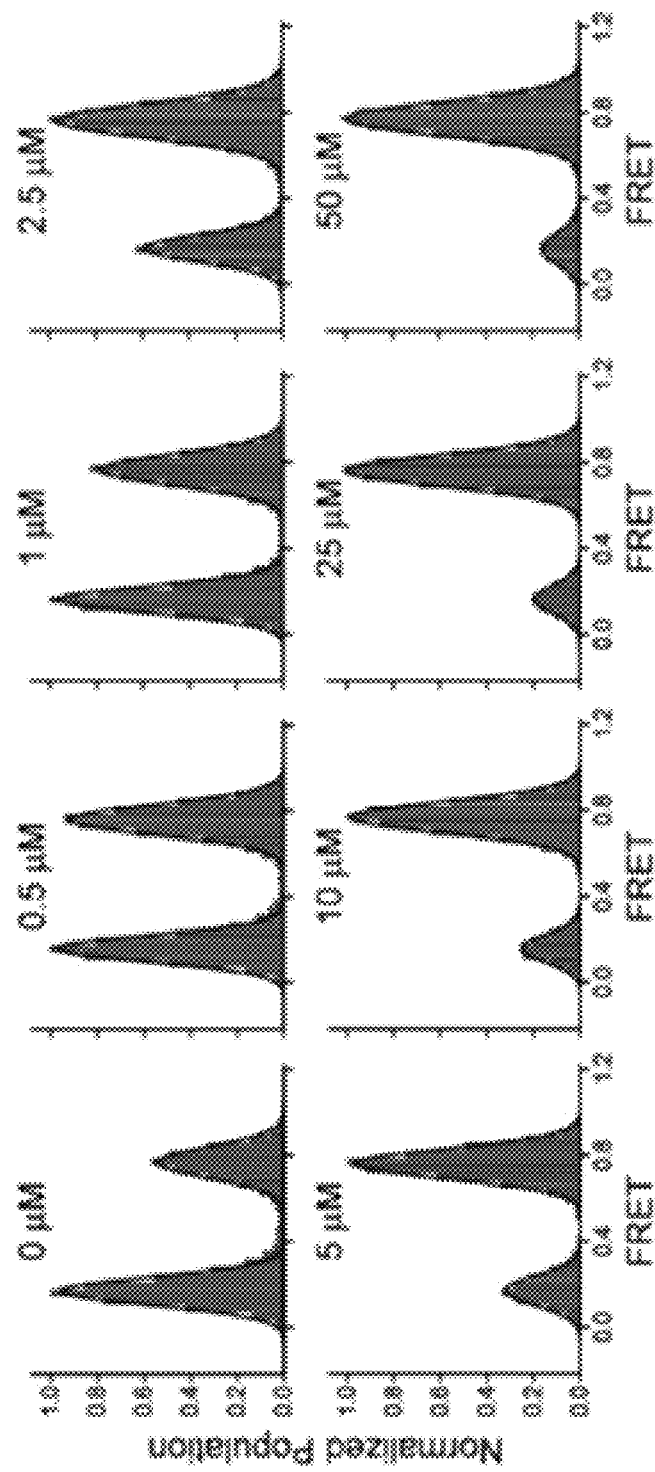
FIG. 24 shows one-dimensional smFRET histograms of RC2$_{Pmn}$+RRF titration. Data from RC2$_{Pmn}$ alone or RC2$_{Pmn}$ were collected in the presence of the concentration of RRF shown. One-dimensional histograms (red bars) were generated using the first 10 frames of resulting smFRET data. Fits of the two Gaussian distributions in each histogram (black lines) yield population information for GS1 (0.16 FRET) and GS2 (0.76 FRET), and the GS2/GS1 peak area ratio defines the equilibrium constant (K$_{eq}$) governing the GS1⇌GS2 equilibrium at every RRF concentration.
Figure 25:
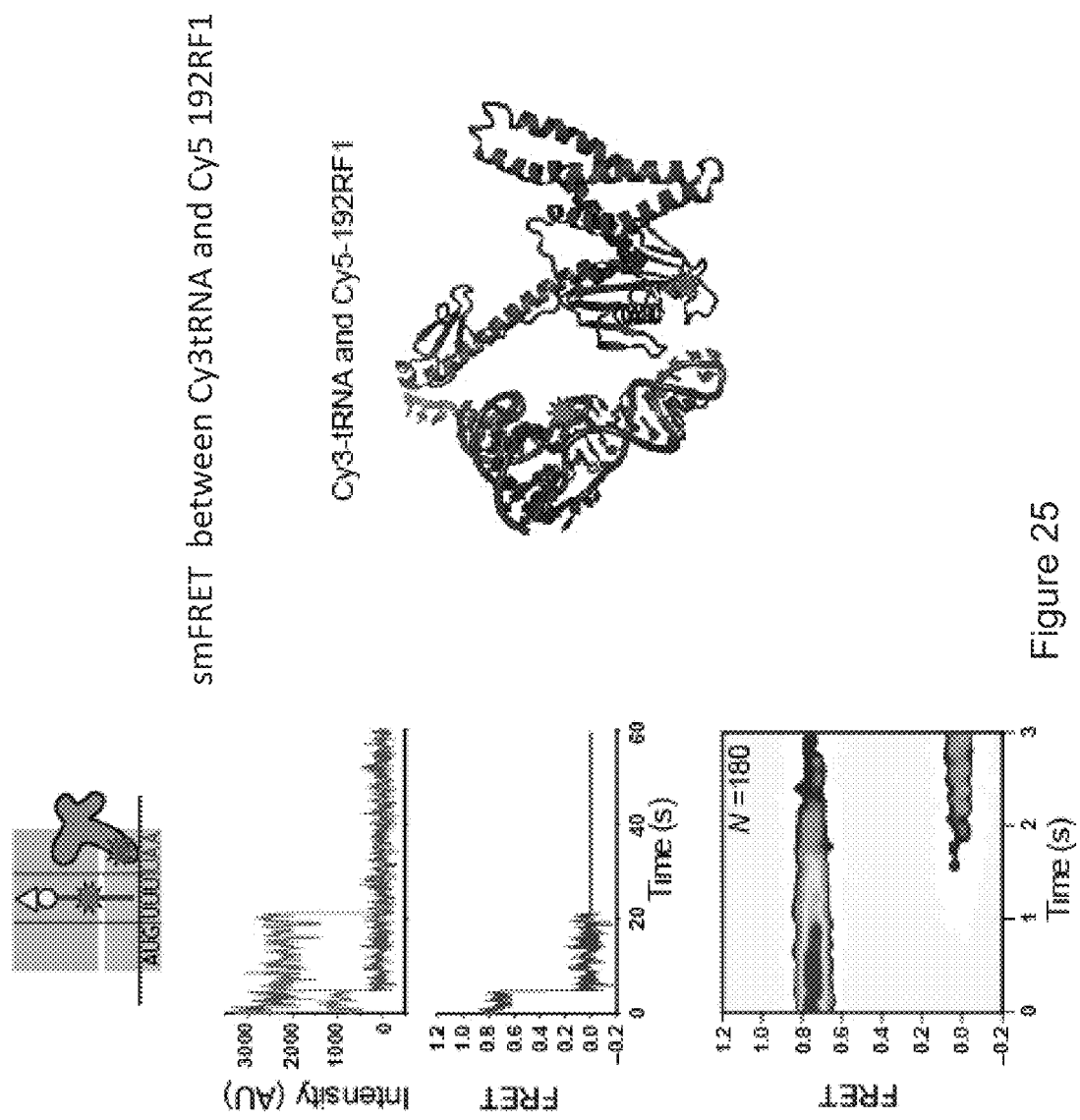
FIG. 25 shows the smFRET signal for Cy3tRNA at the P site and Cy5192RF1 at the A site for use in monitoring stable or transient interaction of RF1 to the release complex (RC).
Figure 26:
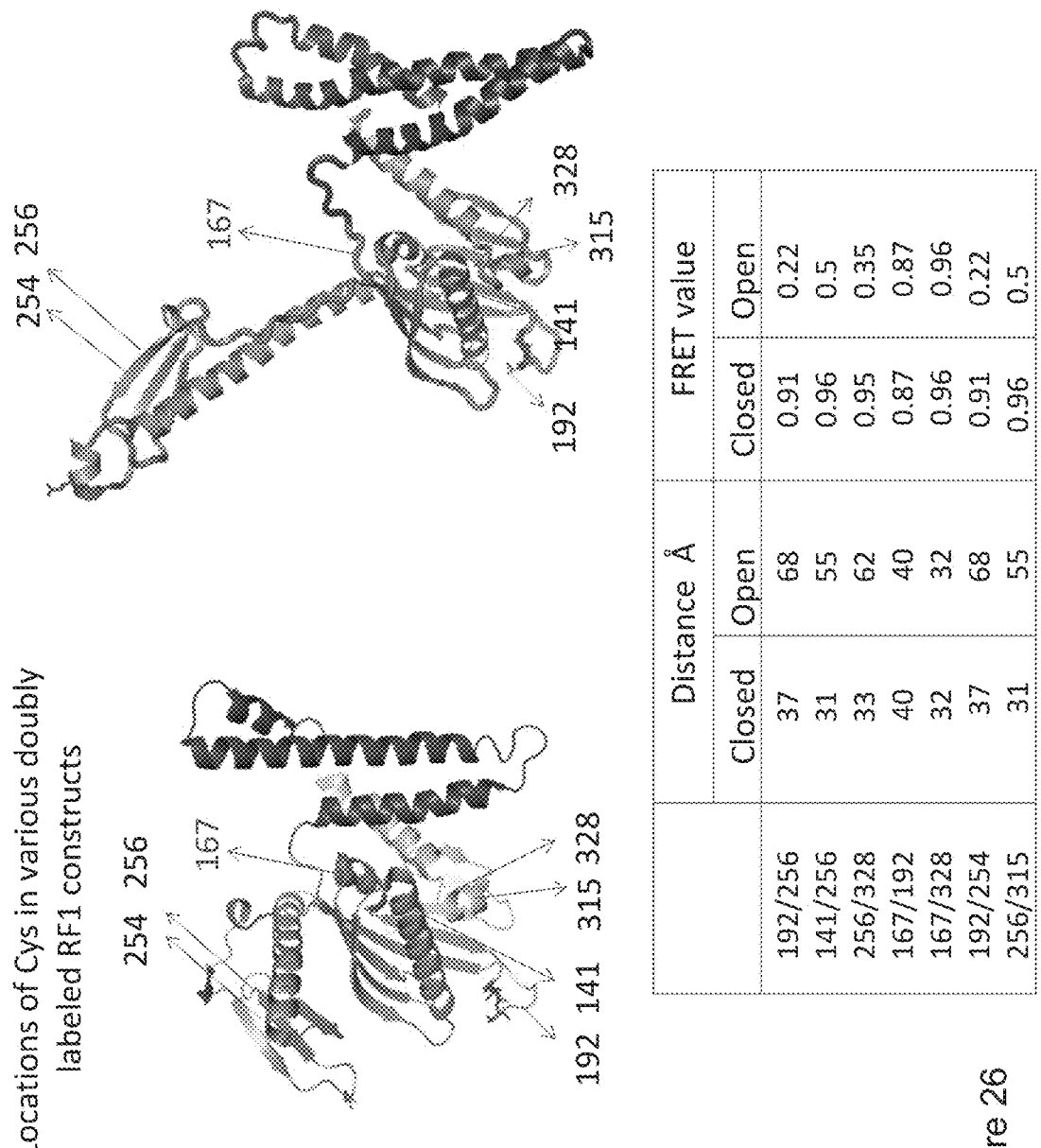
FIG. 26 shows the location of the uniquely engineered Cys in the RF1.
Figure 27:
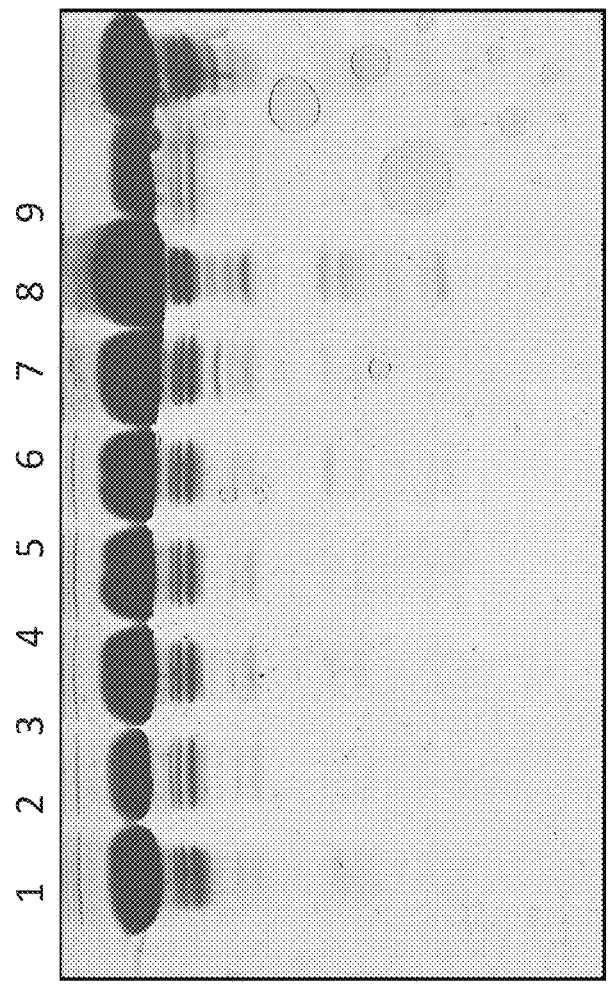
FIG. 27 shows the SDS-PAGE profile of various double Cys mutants of RF1.
Figure 28:
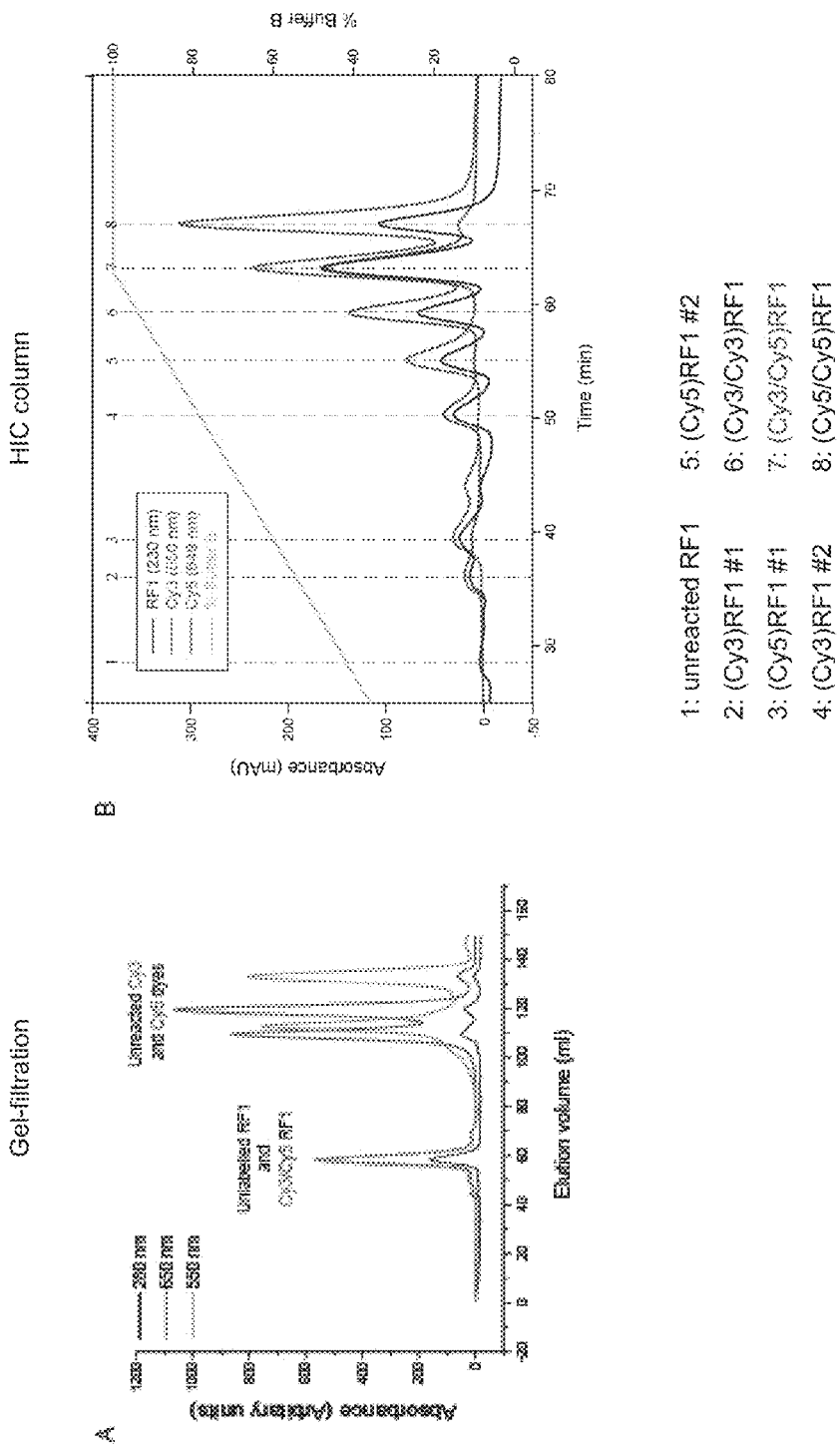
FIG. 28 shows the preparation of doubly-labeled Cy3/Cy5-RF1.
Figure 29:
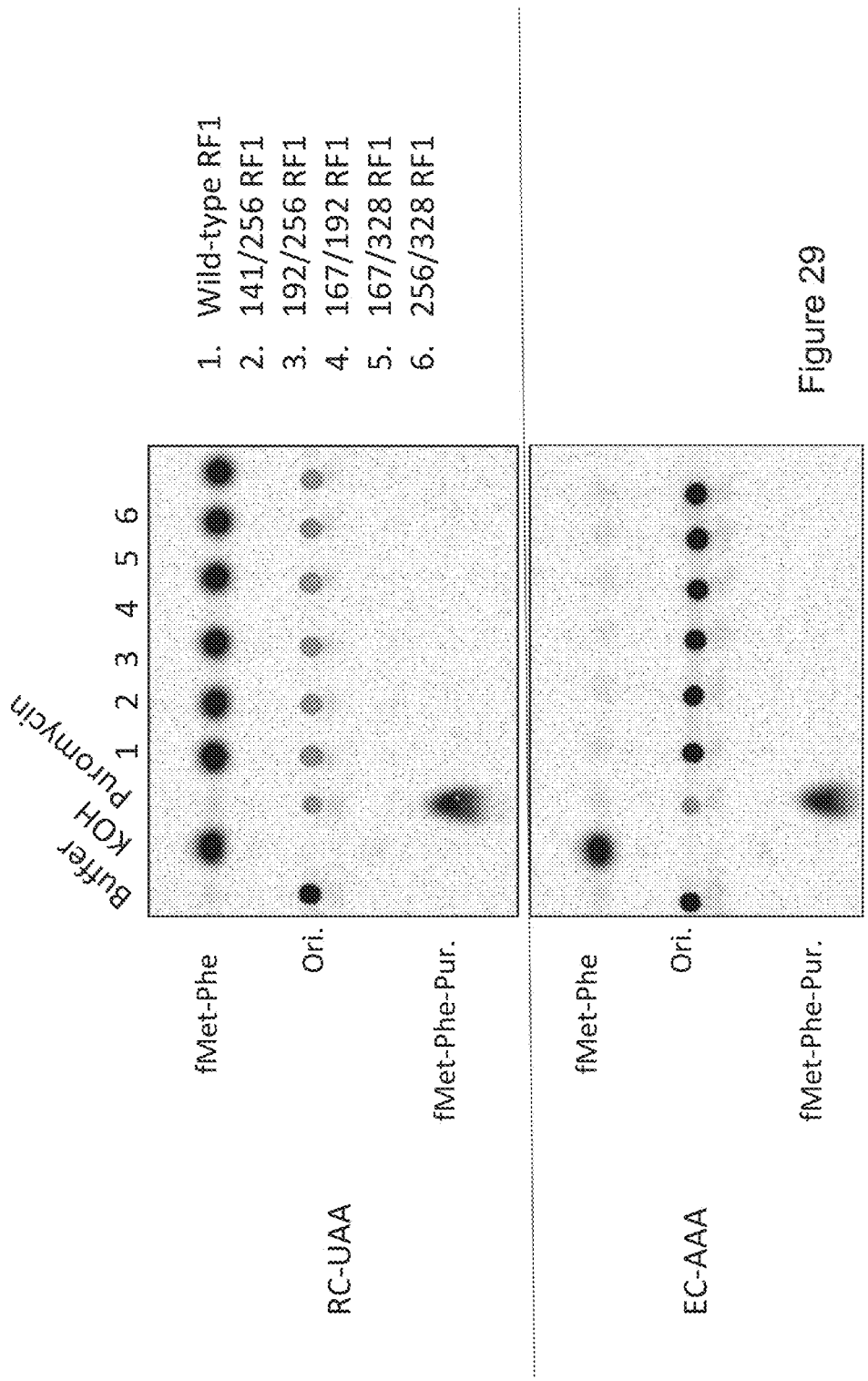
FIG. 29 shows the specificity of various double Cys mutants of RF1 in releasing dipeptide at the authentic stop codons.
Figure 30:
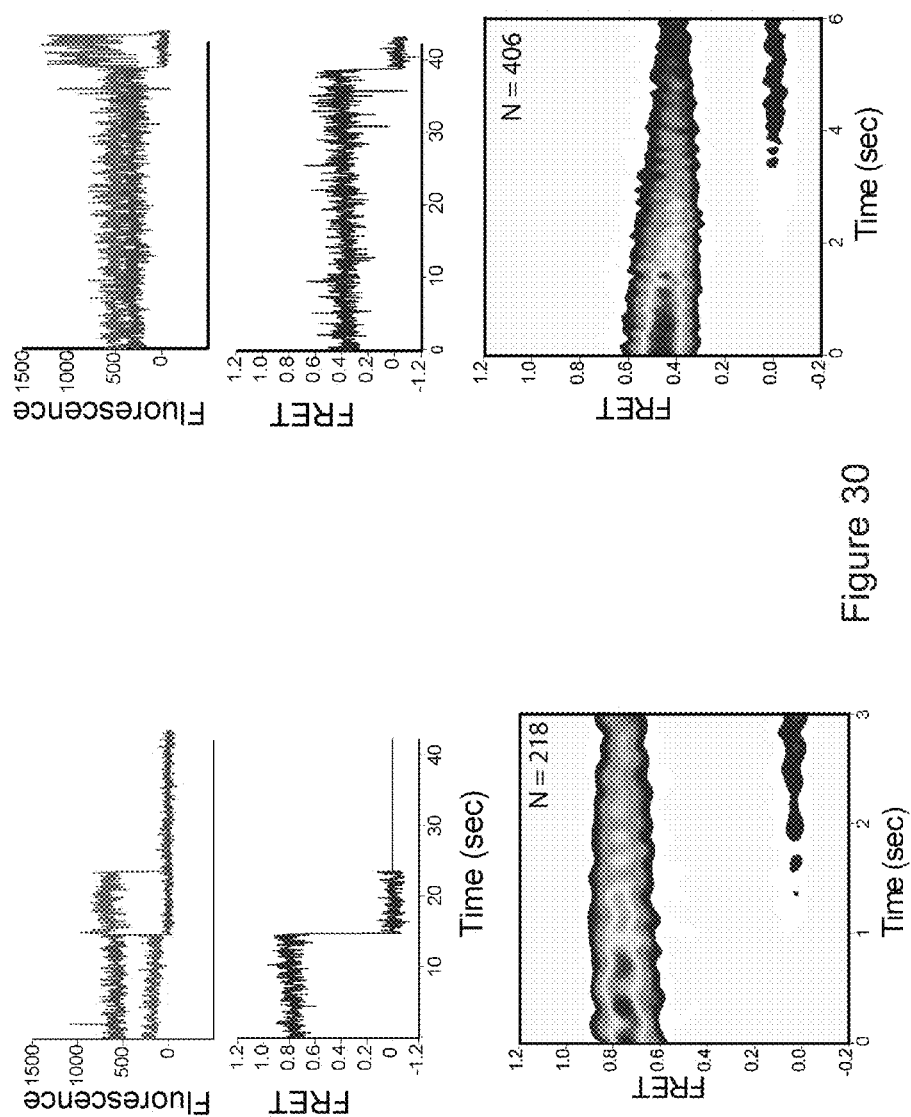
FIG. 30 shows the smFRET trajectory of 192/256-Cy3/Cy5 RF1, alone and bound to the RC.
Figure 34:
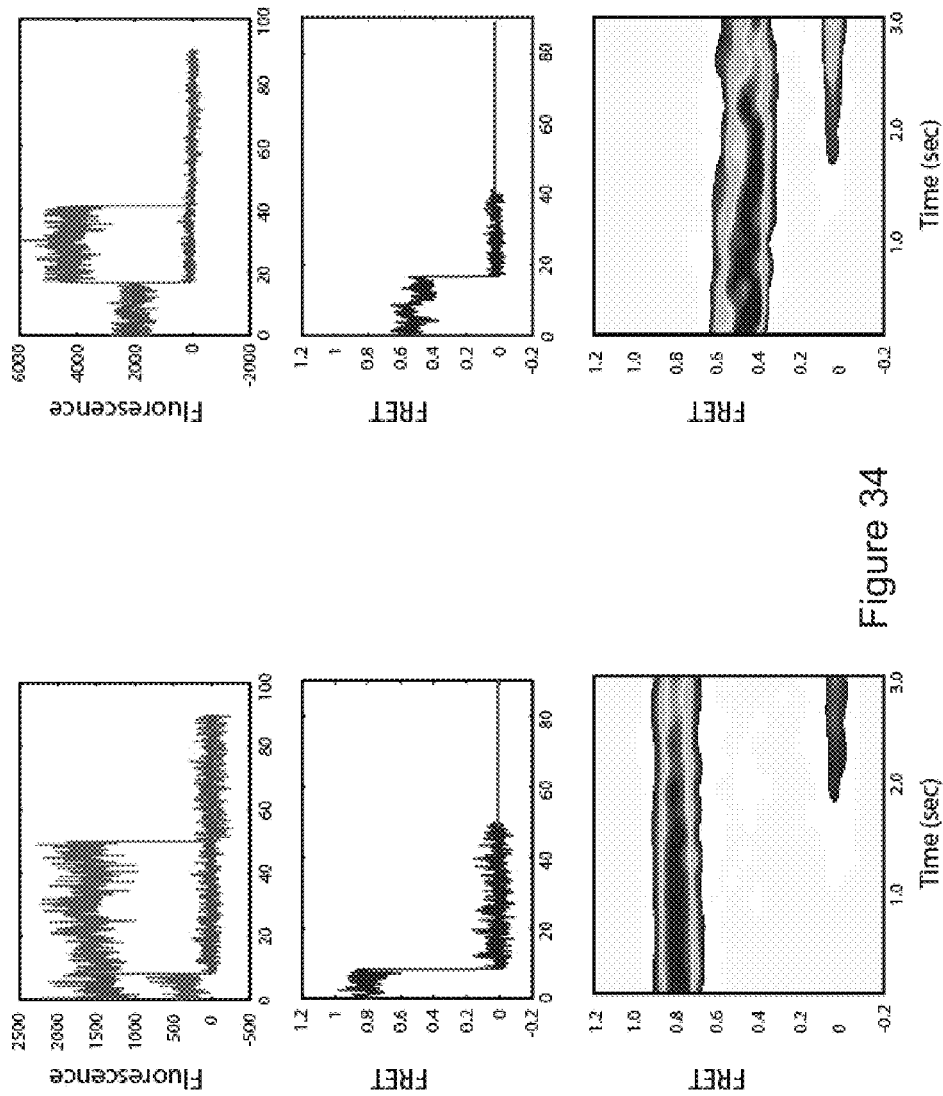
FIG. 34 shows the smFRET trajectory of 192/254-Cy3/Cy5 RF1, alone and bound to the RC.
Figure 35:
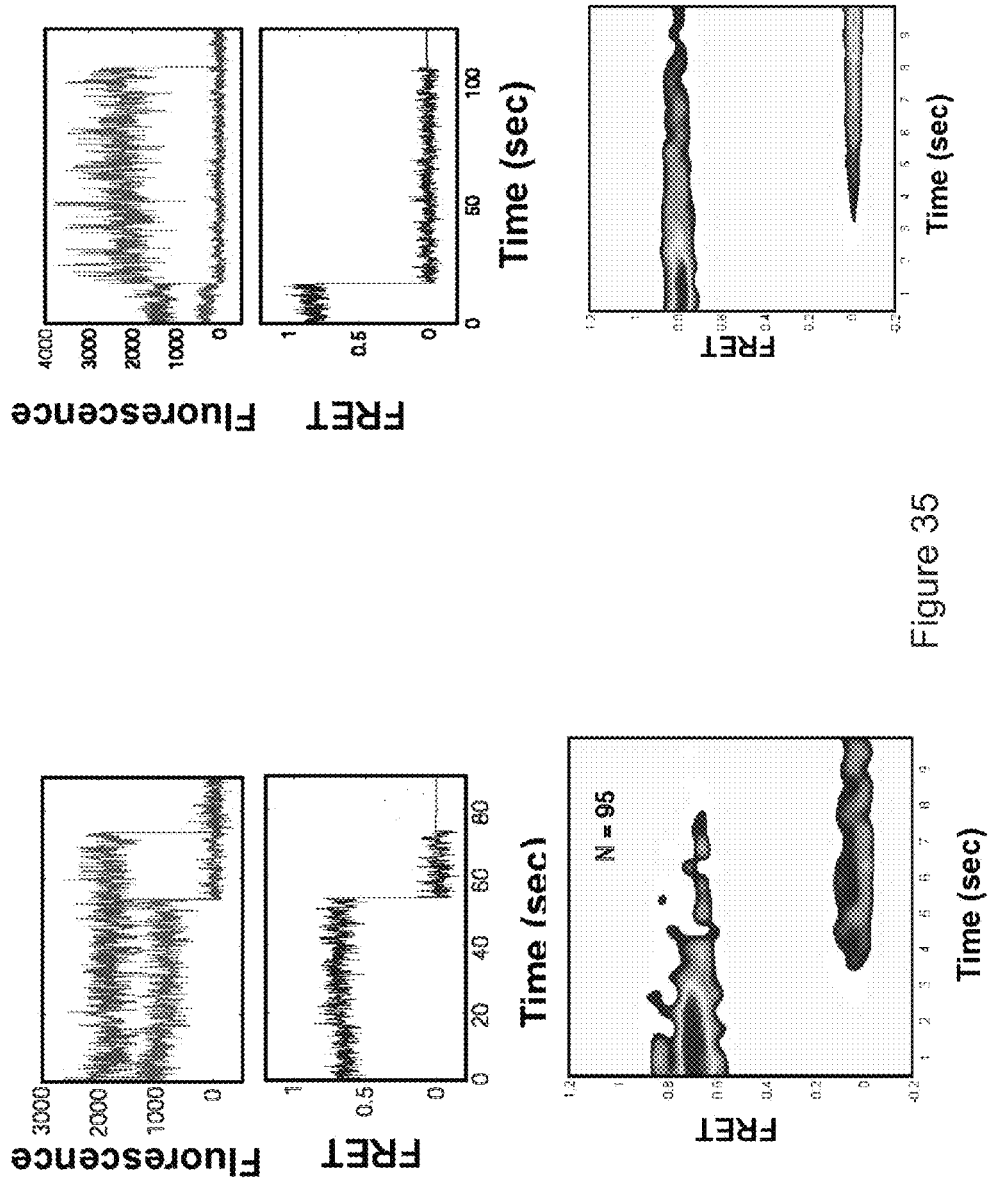
FIG. 35 shows the smFRET trajectory of 167/192-Cy3/Cy5 RF1, alone and bound to the RC.

To more quantitatively probe the subtle effect of RRF on the GS1⇆GS2 equilibrium, one-dimensional smFRET histograms of the entire population of trajectories were plotted as a function of RRF concentration (FIG. 24). The areas under the peaks centered at 0.16 and 0.76 FRET report the equilibrium populations of GS1 and GS2, respectively. These plots show that the GS1 population decreases while the GS2 population increases as a function of increasing RRF concentration. Assuming that RRF can bind to both GS1 and GS2, a plot of the GS2/GS1 peak area ratio ($K_{eq}$) vs. RRF concentration can be fit by the following binding isotherm in order to determine the equilibrium dissociation constants for RRF binding to GS1 ($K_{d,GS1}$) and GS2 ($K_{d,GS2}$) (Sarkar et al. 2007):

$$\frac{GS2 \text{ peak area}}{GS1 \text{ peak area}} = C\left[1 + \frac{[RRF]}{K_{d,GS1}}\right] \Big/ \left[1 + \frac{[RRF]}{K_{d,GS2}}\right]$$

where C is the GS2/GS1 peak area ratio in the absence of RRF.

This analysis yields a $K_{d,GS2}$ of 0.9±0.3 µM and a $K_{d,GS1}$ of 12±2 µM (FIG. 23B), revealing that RRF exhibits greater than an order of magnitude tighter binding to GS2 over GS1. This result is consistent with a clear steric clash between the binding positions of RRF and the aminoacyl-end of classically-bound tRNA at the P site within GS1 (Barat et al. 2007; Borovinskaya et al. 2007; Weixlbaumer et al. 2007; Gao et al. 2005; Agrawal et al. 2004; Lancaster et al. 2002). The $K_d$ of RRF binding to vacant ribosomes (i.e. in the absence of mRNA or tRNAs) is in the range of 0.2-0.6 µM (Seo et al. 2004; Kiel et al. 2003; Hirokawa et al. 2002). This is consistent with the $K_d$ for GS2, further demonstrating that RRF can interact with the GS2 conformation of the PoTC in much the same way as it does with a vacant ribosome.

To explore the kinetic basis for the RRF-mediated change in the GS1⇆GS2 equilibrium, $k_{GS1 \to GS2}$ and $k_{GS2 \to GS1}$ was determined in a low RRF concentration range (0-1.5 µM), where substantial corrections for premature truncation of the trajectories due to photobleaching are not necessary. Analysis of these data shows that, at RRF concentrations near $K_{d,GS2}$, $k_{GS1 \to GS2}$ remain unchanged while $k_{GS2 \to GS1}$ decreases linearly (FIG. 23C). The observation that $k_{GS1 \to GS2}$ remains unchanged is consistent with the low affinity of RRF for GS1. This result further reveals that, at low RRF concentrations, RRF neither induces nor inhibits the GS1→GS2 transition. Instead, RRF depends upon a spontaneous GS1→GS2 transition for access to the GS2 conformation of the PoTC. The decrease in $k_{GS2 \to GS1}$ within the same RRF concentration range demonstrates that RRF binds to GS2 and inhibits GS2→GS1 transitions. The results demonstrate that at RRF concentrations near $K_{d,GS2}$, RRF rapidly binds to and dissociates from GS2, with binding directly competing with the GS2→GS1 transition. As the concentration of RRF increases, repeated RRF binding events begin to out-compete the GS2→GS1 transition, thus leading to the observed steady decrease in $k_{GS2 \to GS1}$.

The $K_{d,GS1}$ of 12±2 µM, is consistent with a lack of appreciable effect in $k_{GS1 \to GS2}$ at RRF concentrations of 0-1.5 µM. To assess whether RRF can affect $k_{GS1 \to GS2}$ at higher concentrations, the 50 µM RRF dataset was examined for rare excursions to GS1. Dwell-time analysis of these rare events revealed that, at 50 µM RRF, $k_{GS1 \to GS2}$ is 1.6-fold faster than $k_{GS1 \to GS2}$ for free RC2$_{Pmn}$ (0.83±0.06 s$^{-1}$ versus 0.52±0.03 s$^{-1}$, respectively). Thus, at high enough concentrations where substantial binding to GS1 becomes possible, RRF modestly promotes the GS1→GS2 transition. Collectively, these results demonstrate that the population of PoTCs found in the GS2 conformation can be tuned by regulating RRF concentration.

Example 22

RF1 Free in Solution Predominantly Populates the Closed State

To determine whether a large-scale conformational change of RF1 is involved in allosteric communication between the DC and the PTC during termination, a double-labeled RF1 was constructed for intramolecular smFRET measurements. Doubly-labeled RF1 yields four easily distinguished and separable labeling combinations. Two of these are Cy3/Cy5 doubly-labeled and generate an indistinguishable smFRET signal, the other two are doubly-Cy3 or doubly-Cy5 labeled. The doubly-Cy5 labeled molecules are non-fluorescent in a smFRET experiment and the doubly-Cy3 labeled molecules are identified by their two-fold higher average intensity and two-step photobleaching behavior. Using hexa-histidine tagged RF1 ('hexahistidine 2 disclosed as SEQ ID NO:9) (by omitting proteolytic cleavage of the hexa-histidine affinity tag (SEQ ID NO:9) of the RF1 construct) and a biotin-conjugated anti-hexa-histidine antibody ('hexahistidine 2 disclosed as SEQ ID NO:9) (Rockland Immunochemicals, Inc.), the doubly-labeled RF1 was anchored to standard PEG/streptavidin-coated microscope slides and used to collect smFRET data directly reporting on the open-closed dynamics of RF1 (FIG. 5 and FIG. 12).

Based on distances measured from crystal structures of the closed (Graille et al. 2005; Shin et al. 2004) and open (Petry et al. 2005) states of RF1 and the locations of the dyes in the doubly-labeled RF1, FRET values of 0.94 and 0.33 FRET, respectively, were expected. Inspection of individual smFRET versus time trajectories (FIG. 12, second row) recorded on isolated RF1 reveal one predominant FRET value centered at 0.90, fully consistent with the closed conformation of RF1. Short-lived unstable fluctuations to lower FRET values were observed. This is consistent with opening of RF1. A stable population at the expected 0.33 FRET value consistent with the open conformation of RF1 was not observed. These experiments demonstrate that, RF1 exists predominantly in the closed conformation in a free solution and that transitioning to the open conformation(s) occurs only transiently. Accordingly, RF1 either (1) initially binds to the RC in the closed conformation and undergoes the closed-to-open conformational change within the RC (perhaps as part of allosteric signaling between the DC and the PTC) or (2) undergoes a spontaneous closed-to-open fluctuation in solution that then allows RF1 to bind directly to the RC in the open conformation.

To map the conformational trajectory of RF1 during termination, pre-steady state smFRET experiments are performed where RC is stopped-flow delivered to surface-immobilized doubly-labeled RF1 (or alternatively, doubly-labeled RF1 can be delivered to surface-immobilized RC). These data provide real-time trajectories of RF1 binding to the RC and stop-codon dependent conformational changes. These experiments, in combination with the smFRET experiments using singly-labeled (Cy5)RF1 variants, can be used to further describe the role of RF1 conformational dynamics in allosteric signaling between the DC and the PTC during termination.

REFERENCES

Agirrezabala, X. et al. Visualization of the hybrid state of tRNA binding promoted by spontaneous ratcheting of the ribosome. Mol Cell 32, 190-197 (2008).

Agrawal, R. K. et al. Visualization of ribosome-recycling factor on the *Escherichia coli* 70S ribosome: functional implications. Proc Natl Acad Sci USA 101, 8900-8905 (2004).

Alkalaeva, E. Z., Pisarev, A. V., Frolova, L. Y., Kisselev, L. L., and Pestova, T. V., (2006) In vitro reconstitution of eukaryotic translation reveals cooperativity between release factors eRF1 and eRF3. *Cell*, 125 (6): 1125-36.

Altschul, S. F., Gish, W., Miller, W., Myers, E. W. & Lipman, D. J. Basic local alignment search tool. *J Mol Biol* 215, 403-410 (1990).

Anczukow, O., Ware, M. D., Buisson, M., Zetoune, A. B., Stoppa-Lyonnet, D., Sinilnikova, O. M., and Mazoyer, S., (2007) Does the nonsense-mediated mRNA decay mechanism prevent the synthesis of truncated BRCA1, CHK2, and p53 proteins? *Hum Mutat*, E-pub, ahead of print.

Andrec, M., Levy, R. M., and Talaga, D. S., (2003) Direct Determination of Kinetic Rates from Single-Molecule Photon Arrival Trajectories Using Hidden Markov Models. *J Phys Chem A*, 107 (38): 7454-7464.

Barat, C., Datta, P. P., Raj, V. S., Sharma, M. R., Kaji, H., Kaji, A., and Agrawal, R. K., (2007) Progression of the ribosome recycling factor through the ribosome dissociates the two ribosomal subunits. *Mol Cell*, 27 (2): 250-61.

Bartley, L. E., Zhuang, X., Das, R., Chu, S. & Herschlag, D. Exploration of the transition state for tertiary structure formation between an RNA helix and a large structured RNA. *J Mol Biol* 328, 1011-1026 (2003).

Barton-Davis, E. R., Cordier, L., Shoturma, D. I., Leland, S. E., and Sweeney, H. L., (1999) Aminoglycoside antibiotics restore dystrophin function to skeletal muscles of mdx mice. *J Clin Invest*, 104 (4): 375-81.

Bastiaens, P. I. & Jovin, T. M. Microspectroscopic imaging tracks the intracellular processing of a signal transduction protein: fluorescent-labeled protein kinase C beta I. Proc Natl Acad Sci U S A 93, 8407-8412 (1996).

Bertram, G., Innes, S., Minella, O., Richardson, J., and Stansfield, I., (2001) Endless possibilities: translation termination and stop codon recognition. *Microbiology*, 147 (Pt 2): 255-69.

Bjomsson, A., Mottagui-Tabar, S., and Isaksson, L. A., (1996) Structure of the C-terminal end of the nascent peptide influences translation termination. *Embo J*, 15 (7): 1696-704.

Blanchard, S. C., Gonzalez Jr., R. L., Kim, H. D., Chu, S., and Puglisi, J. D., (2004a) tRNA selection and kinetic proofreading in translation. *Nat Struct Mol Biol*, 11: 1008-1014.

Blanchard, S. C., Kim, H. D., Gonzalez Jr., R. L., Puglisi, J. D., and Chu, S., (2004b) tRNA dynamics on the ribosome during translation. *Proc Natl Acad Sci USA*, 101: 12893-12898.

Bonetti, B., Fu, L., Moon, J., and Bedwell, D. M., (1995) The efficiency of translation termination is determined by a synergistic interplay between upstream and downstream sequences in *Saccharomyces cerevisiae*. *J Mol Biol*, 251 (3): 334-45.

Borovinskaya, M. A., Pai, R. D., Zhang, W., Schuwirth, B. S., Holton, J. M., Hirokawa, G., Kaji, H., Kaji, A., and Cate, J. H., (2007) Structural basis for aminoglycoside inhibition of bacterial ribosome recycling. *Nat Struct Mol Biol*, 14 (8): 727-32.

Brito, M., Malta-Vacas, J., Carmona, B., Aires, C., Costa, P., Martins, A. P., Ramos, S., Conde, A. R., and Monteiro, C., (2005) Polyglycine expansions in eRF3/GSPT1 are associated with gastric cancer susceptibility. *Carcinogenesis*, 26 (12): 2046-2049.

Brown, C. M., McCaughan, K. K., and Tate, W. P., (1993) Two regions of the *Escherichia coli* 16S ribosomal RNA are important for decoding stop signals in polypeptide chain termination. *Nucleic Acids Res*, 21 (9): 2109-2115.

Buckingham, R. H., Grentzmann, G., and Kisselev, L., (1997) Polypeptide chain release factors. *Mol Microbiol*, 24 (3): 449-56.

Chabelskaya, S., Gryzina, V., Moskalenko, S., Le Goff, C., and Zhouravleva, G., (2007) Inactivation of NMD increases viability of sup45 nonsense mutants in *Saccharomyces cerevisiae*. *BMC Mot Biol*, 8 (1): 71.

Chang, Y. F., Imam, J. S., and Wilkinson, M. F., (2007) The nonsense-mediated decay RNA surveillance pathway. *Annu Rev Biochem*, 76: 51-74.

Chavatte, L., Frolova, L., Kisselev, L., and Favre, A., (2001) The polypeptide chain release factor eRF1 specifically contacts the s(4)UGA stop codon located in the A site of eukaryotic ribosomes. *Eur J Biochem*, 268 (10): 2896-904.

Cheng, Z. et al. Structural insights into eRF3 and stop codon recognition by eRF1. Genes Dev 23, 1106-1118 (2009).

Clancy, J. P., Bebok, Z., Ruiz, F., King, C., Jones, J., Walker, L., Greer, H., Hong, J., Wing, L., Macaluso, M., Lyrene, R., Sorscher, E. J., and Bedwell, D. M., (2001) Evidence that systemic gentamicin suppresses premature stop mutations in patients with cystic fibrosis. *Am J Respir Crit. Care Med*, 163 (7): 1683-92.

Collins, R. T. and Cohen, S. M., (2005) A genetic screen in *Drosophila* for identifying novel components of the hedgehog signaling pathway. *Genetics*, 170 (1): 173-84.

Connell, S. R., Takemoto, C., Wilson, D. N., Wang, H., Murayama, K., Terada, T., Shirouzu, M., Rost, M., Schuler, M., Giesebrecht, J., Dabrowski, M., Mielke, T., Fucini, P., Yokoyama, S., and Spahn, C. M., (2007) Structural basis for interaction of the ribosome with the switch regions of GTP-bound elongation factors. *Mol Cell*, 25 (5): 751-64.

Cornish, P. V. et al. Following movement of the L1 stalk between three functional states in single ribosomes. Proc Natl Acad Sci USA (2009).

Cornish, P. V., Ermolenko, D. N., Noller, H. F. & Ha, T. Spontaneous intersubunit rotation in single ribosomes. Mol Cell 30, 578-588 (2008).

Dincbas-Renqvist V, Engstrom A, Mora L, Heurgue-Hamard V, Buckingham R, and M., E., (2000) A post-translational modification in the GGQ motif of RF2 from *Escherichia coli* stimulates termination of translation. *EMBO (Eur Mol Biol Organ) J,* 19 (24): 6900-6907.

Dorywalska, M., Blanchard, S. C., Gonzalez Jr., R. L., Kim, H. D., Chu, S., and Puglisi, J. D., (2005) Site-specific labeling of the ribosome for single-molecule spectroscopy. *Nucleic Acids Res,* 33 (1): 182-189.

Du, M., Liu, X., Welch, E. M., Hirawat, S., Peltz, S. W., and Bedwell, D. M., (2008) PTC124 is an orally bioavailable compound that promotes suppression of the human CFTR G542X nonsense allele in a CF mouse model. *Proc Natl Acad Sci USA,* 105 (6): 2064-9.

Dubourg, C., Toutain, B., Helias, C., Henry, C., Lessard, M., Le Gall, J. Y., Le Treut, A., and Guenet, L., (2002) Evaluation of ETF1/eRF1, mapping to 5q31, as a candidate myeloid tumor suppressor gene. *Cancer Genet Cytogenet,* 134 (1): 33-37.

English, B. P., Min, W., van Oijen, A. M., Lee, K. T., Luo, G., Sun, H., Cherayil, B. J., Kou, S. C., and Xie, X. S., (2006) Ever-fluctuating single enzyme molecules: Michaelis-Menten equation revisited. *Nat Chem Biol,* 2 (2): 87-94.

Ermolenko, D. N. et al. Observation of intersubunit movement of the ribosome in solution using FRET. J Mol Biol 370, 530-540 (2007).

Fei, J., Kosuri, P., MacDougall, D. D. & Gonzalez, R. L., Jr. Coupling of ribosomal L1 stalk and tRNA dynamics during translation elongation. Mol Cell 30, 348-359 (2008).

Fourmy, D., Recht, M. I., Blanchard, S. C., and Puglisi, J. D., (1996) Structure of the A site of *E. coli* 16S ribosomal RNA complexed with an aminoglycoside antibiotic. *Science,* 274: 1367-1371.

Frank, J. and Agrawal, R. K., (2000) A ratchet-like intersubunit reorganization of the ribosome during translocation. *Nature,* 406 (6793): 318-22.

Freistroffer, D. V., Kwiatkowski, M., Buckingham, R. H., and Ehrenberg, M., (2000) The accuracy of codon recognition by polypeptide release factors. *Proc Natl Acad Sci U S A,* 97 (5): 2046-51.

Freistroffer, D. V., Pavlov, M. Y., MacDougall, J., Buckingham, R. H. & Ehrenberg, M. Release factor RF3 in *E. coli* accelerates the dissociation of release factors RF1 and RF2 from the ribosome in a GTP-dependent manner. EMBO J. 16, 4126-4133 (1997).

Frischmeyer, P. A., Dietz, Harry C., (1999) Nonsense-mediated mRNA decay in health and disease. *Human Molecular Genetics,* 8 (10): 1893-1900.

Frolova, L. Y., Tsivkovskii, R. Y., Sivolobova, G. F., Oparina, N. Y., Serpinsky, O. I., Blinov, V. M., Tatkov, S. I., and Kisselev, L. L., (1999) Mutations in the highly conserved GGQ motif of class 1 polypeptide release factors abolish ability of human eRF1 to trigger peptidyl-tRNA hydrolysis. *Rna,* 5 (8): 1014-20.

Fujiwara, T., Ito, K., Yamami, T., and Nakamura, Y., (2004) Ribosome recycling factor disassembles the post-termination ribosomal complex independent of the ribosomal translocase activity of elongation factor G. *Mol Microbiol,* 53 (2): 517-28.

Gao, H., Zhou, Z., Rawat, U., Huang, C., Bouakaz, L., Wang, C., Cheng, Z., Liu, Y., Zavialov, A., Gursky, R., Sanyal, S., Ehrenberg, M., Frank, J., and Song, H., (2007a) RF3 induces ribosomal conformational changes responsible for dissociation of class I release factors. *Cell,* 129 (5): 929-41.

Gao, N., Zavialov, A. V., Ehrenberg, M., and Frank, J., (2007b) Specific interaction between EF-G and RRF and its implication for GTP-dependent ribosome splitting into subunits. *J Mol Biol,* 374 (5): 1345-58.

Gao, N., Zavialov, A. V., Li, W., Sengupta, J., Valle, M., Gursky, R. P., Ehrenberg, M., and Frank, J., (2005) Mechanism for the disassembly of the posttermination complex inferred from cryo-EM studies. *Mol Cell,* 18 (6): 663-74.

Goncalves, J., Malta-Vacas, J., Louis, M., Brault, L., Bagrel, D., Monteiro, C., and Brito, M., (2005) Modulation of translation factor's gene expression by histone deacetylase inhibitors in breast cancer cells. *Clin Chem Lab Med,* 43 (2): 151-6.

Gonzalez Jr., R. L., Chu, S., and Puglisi, J. D., (2007) Thiostrepton inhibition of tRNA delivery to the ribosome. *RNA,* 13 (12): 2091-2097.

Graille, M., Heurgue-Hamard, V., Champ, S., Mora, L., Scrima, N., Ulryck, N., van Tilbeurgh, H., and Buckingham, R. H., (2005) Molecular basis for bacterial class I release factor methylation by PrmC. *Mol Cell,* 20 (6): 917-27.

Green, R. E., Lewis, B. P., Hillman, R. T., Blanchette, M., Lareau, L. F., Garnett, A. T., Rio, D. C., and Brenner, S. E., (2003) Widespread predicted nonsense-mediated mRNA decay of alternatively spliced transcripts of human normal and disease genes. *Bioinformatics,* 19 Suppl 1: i118-21.

Guenet, L., Henry, C., Toutain, B., Dubourg, C., Le Gall, J. Y., David, V., Le Treut, A., (2000) Eukaryotic translation termination factor gene (ETF1/eRF1) maps at D5S500 in a commonly deleted region of chromosome 5q31 in malignant myeloid diseases. *Cytogenet Cell Genet,* 88 (1-2): 82-86.

Guex, N. & Peitsch, M. C. SWISS-MODEL and the Swiss-PdbViewer: an environment for comparative protein modeling. *Electrophoresis* 18, 2714-2723 (1997).

Guo, P., Zhang, L., Zhang, H., Feng, Y., and Jing, G., (2006) Domain II plays a crucial role in the function of ribosome recycling factor. *Biochem J,* 393 (Pt 3): 767-77.

Heurgue-Hamard, V., Champ, S., Engstrom, A., Ehrenberg, M. & Buckingham, R. H. The hemK gene in *Escherichia coli* encodes the N(5)-glutamine methyltransferase that modifies peptide release factors. EMBO J. 21, 769-778 (2002).

Hirokawa, G. et al. The role of ribosome recycling factor in dissociation of 70S ribosomes into subunits. RNA 11, 1317-1328 (2005).

Hirokawa, G., Inokuchi, H., Kaji, H., Igarashi, K. & Kaji, A. In vivo effect of inactivation of ribosome recycling factor—fate of ribosomes after unscheduled translation downstream of open reading frame. Mol Microbiol 54, 1011-1021 (2004).

Hirokawa, G., Kiel, M. C., Muto, A., Kawai, G., Igarashi, K., Kaji, H., and Kaji, A., (2002) Binding of ribosome recycling factor to ribosomes, comparison with tRNA. *J Biol Chem,* 277 (39): 35847-52.

Hohng, S., Joo, C. & Ha, T. Single-molecule three-color FRET. Biophys J 87, 1328-1337 (2004).

Horton, H. R., Moran, L. A., Ochs, R. S., Rawn, D. J., and Scrimgeour, K. G., *Principles of Biochemistry,* 3rd Edition. 3 ed. 2006: Prentice Hall.

Howard, M. T., Shirts, B. H., Petros, L. M., Flanigan, K. M., Gesteland, R. F., and Atkins, J. F., (2000) Sequence specificity of aminoglycoside-induced stop condon readthrough: potential implications for treatment of Duchenne muscular dystrophy. *Ann Neurol,* 48 (2): 164-9.

Ionov, Y., Nowak, N., Perucho, M., Markowitz, S., and Cowell, J. K., (2004) Manipulation of nonsense mediated decay identifies gene mutations in colon cancer Cells with microsatellite instability. *Oncogene,* 23 (3): 639-45.

Ito, K., Uno, M., and Nakamura, Y., (2000) A tripeptide 'anticodon' deciphers stop codons in messenger RNA. *Nature,* 403 (6770): 680-4.

Ito, K., Uno, M., and Nakamura, Y., (1998) Single amino acid substitution in prokaryote polypeptide release factor 2 permits it to terminate translation at all three stop codons. *Proc Natl Acad Sci USA,* 95 (14): 8165-9.

Ivanov, I., Lo, K. C., Hawthorn, L., Cowell, J. K., and Ionov, Y., (2007) Identifying candidate colon cancer tumor suppressor genes using inhibition of nonsense-mediated mRNA decay in colon cancer cells. *Oncogene,* 26 (20): 2873-84.

Janosi, L. et al. Evidence for in vivo ribosome recycling, the fourth step in protein biosynthesis. EMBO J. 17, 1141-1151 (1998).

Janzen, D. M. and Geballe, A. P., (2004) The effect of eukaryotic release factor depletion on translation termination in human cell lines. *Nucleic Acids Res,* 32 (15): 4491-502.

Jorgensen, F., Adamski, F. M., Tate, W. P., and Kurland, C. G., (1993) Release factor-dependent false stops are infrequent in *Escherichia coli. J Mol Biol,* 230 (1): 41-50.

Julian, P. et al. Structure of ratcheted ribosomes with tRNAs in hybrid states. Proc Natl Acad Sci USA 105, 16924-16927 (2008).

Karimi, R., Pavlov, M. Y., Buckingham, R. H., and Ehrenberg, M., (1999) Novel roles for classical factors at the interface between translation termination and initiation. *Mol Cell,* 3 (5): 601-9.

Keeling, K. M. and Bedwell, D. M., (2002) Clinically relevant aminoglycosides can suppress diseaseassociated premature stop mutations in the IDUA and P53 cDNAs in a mammalian translation system. *J Mol Med,* 80 (6): 367-76.

Kiel, M. C., Raj, V. S., Kaji, H., and Kaji, A., (2003) Release of ribosome-bound ribosome recycling factor by elongation factor G. *J Biol Chem,* 278 (48): 48041-50.

Kim, H. D., Puglisi, J., and Chu, S., (2007) Fluctuations of transfer RNAs between classical and hybrid states. *Biophys J,* 93 (10): 3575-3582.

Klaholz, B. P., Myasnikov, A. G., and Van Heel, M., (2004) Visualization of release factor 3 on the ribosome during termination of protein synthesis. *Nature,* 427 (6977): 862-5.

Klaholz, B. P., Pape, T., Zavialov, A. V., Myasnikov, A. G., Orlova, E. V., Vestergaard, B., Ehrenberg, M., and van Heel, M., (2003) Structure of the *Escherichia coli* ribosomal termination complex with release factor 2. *Nature,* 421 (6918): 90-4.

Lancaster, L., Kiel, M. C., Kaji, A. & Noller, H. F. Orientation of ribosome recycling factor in the ribosome from directed hydroxyl radical probing. Cell 111, 129-140 (2002).

Laurberg, M. et al. Structural basis for translation termination on the 70S ribosome. Nature 454, 852-857 (2008).

Linde, L., Boelz, S., Nissim-Rafinia, M., Oren, Y. S., Wilschanski, M., Yaacov, Y., Virgilis, D., Neu-Yilik, G., Kulozik, A. E., Kerem, E., and Kerem, B., (2007) Nonsense mediated mRNA decay affects nonsense transcript levels and governs response of cystic fibrosis patients to gentamicin. *J Clin Invest,* 117 (3): 683-92.

Malta-Vacas, J., Aires, C., Costa, P., Conde, A. R., Ramos, S., Martins, A. P., Monteiro, C., and Brito, M., (2005) Differential expression of the eukaryotic release factor 3 (eRF3/GSPT1) according to gastric cancer histological types. *J Clin Pathol* (Lond), 58 (6): 621-625.

Martin, R., Mogg, A. E., Heywood, L. A., Nitschke, L., and Burke, J. F., (1989) Aminoglycoside suppression at UAG, UAA and UGA codons in *Escherichia coli* and human tissue culture cells. *Mol Gen Genet,* 217 (2-3): 411-8.

McKinney, S. A., Joo, C., and Ha, T., (2006) Analysis of single-molecule FRET trajectories using hidden Markov modeling. *Biophys J,* 91 (5): 1941-1951.

Mitkevich, V. A., Kononenko, A. V., Petrushanko, I. Y., Yanvarev, D. V., Makarov, A. A., and Kisselev, L. L., (2006) Termination of translation in eukaryotes is mediated by the quaternary eRF1*eRF3*GTP*Mg2+ complex. The biological roles of eRF3 and prokaryotic RF3 are profoundly distinct. *Nucleic Acids Res,* 34 (14): 3947-54.

Mora, L., Zavialov, A., Ehrenberg, M., and Buckingham, R. H., (2003) Stop codon recognition and interactions with peptide release factor RF3 of truncated and chimeric RF1 and RF2 from *Escherichia coli. Mol Microbiol,* 50 (5): 1467-76.

Munro, J. B., Altman, R. B., O'Connor, N., and Blanchard, S. C., (2007) Identification of two distinct hybrid state intermediates on the ribosome. *Mol Cell,* 25 (4): 505-17.

Nakamura, Y. and Ito, K., (2002) A tripeptide discriminator for stop codon recognition. *FEBS Lett,* 514 (1): 30-33.

Nakano, H., Yoshida, T., Uchiyama, S., Kawachi, M., Matsuo, H., Kato, T., Ohshima, A., Yamaichi, Y., Honda, T., Kato, H., Yamagata, Y., Ohkubo, T., and Kobayashi, Y., (2003) Structure and binding mode of a ribosome recycling factor (RRF) from mesophilic bacterium. *J Biol Chem,* 278 (5): 3427-36.

Ogle, J. M., Brodersen, D. E., Clemons, W. M., Jr., Tarry, M. J., Carter, A. P., and Ramakrishnan, V., (2001) Recognition of cognate transfer RNA by the 30S ribosomal subunit. *Science,* 292 (5518): 897-902.

Pape, T., Wintermeyer, W., and Rodnina, M. V., (1998) Complete kinetic mechanism of elongation factor Tu-dependent binding of aminoacyl-tRNA to the A site of the *E. coli* ribosome. *EMBO (Eur Mol Biol Organ) J,* 17: 7490-7497.

Pavlov, M. Y., Antoun, A., Lovmar, M. & Ehrenberg, M. Complementary roles of initiation factor 1 and ribosome recycling factor in 70S ribosome splitting. EMBO J. 27, 1706-1717 (2008).

Peske, F., Rodnina, M. V., and Wintermeyer, W., (2005) Sequence of steps in ribosome recycling as defined by kinetic analysis. *Mol Cell,* 18 (4): 403-12.

Petry, S., Brodersen, D. E., Murphy, F. V., Dunham, C. M., Selmer, M., Tarry, M. J., Kelley, A. C., and Ramakrishnan, V., (2005) Crystal structures of the ribosome in complex with release factors RF1 and RF2 bound to a cognate stop codon. *Cell,* 123 (7): 1255-1266.

Pisarev, A. V., Hellen, C. U., and Pestova, T. V., (2007) Recycling of eukaryotic posttermination ribosomal complexes. *Cell,* 131 (2): 286-99.

Pisareva, V. P., Pisarev, A. V., Hellen, C. U., Rodnina, M. V., and Pestova, T. V., (2006) Kinetic analysis of interaction of eukaryotic release factor 3 with guanine nucleotides. *J Biol Chem,* 281 (52): 40224-35.

Politano, L., Nigro, G., Nigro, V., Piluso, G., Papparella, S., Paciello, O., and Comi, L. I., (2003) Gentamicin administration in Duchenne patients with premature stop codon. Preliminary results. *Acta Myol,* 22 (1): 15-21.

Poole, E. S., Major, L. L., Mannering, S. A., and Tate, W. P., (1998) Translational termination in *Escherichia coli*:

three bases following the stop codon crosslink to release factor 2 and affect the decoding efficiency of UGA-containing signals. *Nucleic Acids Res,* 26 (4): 954-60.

Poole, E. S., Brown, C. M., and Tate, W. P., (1995) The identity of the base following the stop codon determines the efficiency of in vivo translational termination in *Escherichia coli. Embo J,* 14 (1): 151-8.

Qin, F., Auerbach, A., and Sachs, F., (2000a) A direct optimization approach to hidden Markov modeling for single channel kinetics. *Biophys J,* 79 (4): 1915-27.

Qin, F., Auerbach, A., and Sachs, F., (2000b) Hidden Markov modeling for single channel kinetics with filtering and correlated noise. *Biophys J,* 79 (4): 1928-44.

Rawat, U. et al. Interactions of the release factor RF1 with the ribosome as revealed by cryo-EM. J Mol Biol 357, 1144-1153 (2006).

Rawat, U. B., Zavialov, A. V., Sengupta, J., Valle, M., Grassucci, R. A., Linde, J., Vestergaard, B., Ehrenberg, M., and Frank, J., (2003) A cryo-electron microscopic study of ribosome-bound termination factor RF2. *Nature,* 421 (6918): 87-90.

Rodnina, M. V., Gromadski, K. B., Kothe, U., and Wieden, H. J., (2005) Recognition and selection of tRNA in translation. *FEBS Lett,* 579 (4): 938-42.

Rossi, M. R., Hawthorn, L., Platt, J., Burkhardt, T., Cowell, J. K., and Ionov, Y., (2005) Identification of inactivating mutations in the JAK1, SYNJ2, and CLPTM1 genes in prostate cancer cells using inhibition of nonsense-mediated decay and microarray analysis. *Cancer Genet Cytogenet,* 161 (2): 97-103.

Sarkar, S. K. et al. Engineered holliday junctions as single-molecule reporters for protein-DNA interactions with application to a MerR-family regulator. J Am Chem Soc 129, 12461-12467 (2007).

Seo, H. S., Kiel, M., Pan, D., Raj, V. S., Kaji, A., and Cooperman, B. S., (2004) Kinetics and thermodynamics of RRF, EF-G, and thiostrepton interaction on the *Escherichia coli* ribosome. *Biochemistry,* 43 (40): 12728-40.

Seshadri, A. and Varshney, U., (2006) Mechanism of recycling of post-termination ribosomal complexes in eubacteria: a new role of initiation factor 3. *J Biosci,* 31 (2): 281-9.

Shin, D. H., Brandsen, J., Jancarik, J., Yokota, H., Kim, R., and Kim, S. H., (2004) Structural analyses of peptide release factor 1 from *Thermotoga maritima* reveal domain flexibility required for its interaction with the ribosome. *J Mol Biol,* 341 (1): 227-39.

Spahn, C. M., Gomez-Lorenzo, M. G., Grassucci, R. A., Jorgensen, R., Andersen, G. R., Beckmann, R., Penczek, P. A., Ballesta, J. P., and Frank, J., (2004) Domain movements of elongation factor eEF2 and the eukaryotic 80S ribosome facilitate tRNA translocation. *Embo J,* 23 (5): 1008-19.

Stansfield, I., Eurwilaichitr, L., Akhmaloka, Tuite, M. F., (1996) Depletion in the levels of the release factor eRF1 causes a reduction in the efficiency of translation termination in yeast. *Molecular Microbiology,* 20 (6): 1135-1143.

Stansfield, I., Jones, K. M., Kushnirov, V. V., Daqkesamanskaya, A. R., Poznyakovski, A. I., Paushkin, S. V., Nierras, C. R., Cox, B. S., Ter-Avanesyan, M. D., Tuite, M. F., (1995) The products of the SUP45 (eRF1) and SUP35 genes interact to mediate translation termination in *Saccharomyces cerevisiae. EMBO Journal,* 14 (17): 4365-4373.

Tate, W. P., Poole, E. S., Dalphin, M. E., Major, L. L., Crawford, D. J. G., Mannering, S. A., (1996) The translational stop signal: Codon with a context, or extended factor recognition element? *Biochimie,* 78: 945-952.

Tate, W. P., Brown, Chris M., (1992) Translational termination: "Stop" for protein synthesis or "pause" for regulation of gene expression. *Biochemistry,* 31 (9): 2443-2450.

Taylor, D. J., Nilsson, J., Merrill, A. R., Andersen, G. R., Nissen, P., and Frank, J., (2007) Structures of modified eEF2 80S ribosome complexes reveal the role of GTP hydrolysis in translocation. *Embo J,* 26 (9): 2421-31.

Traut, R. R. & Monro, R. E. The puromycin reaction and its relation to protein synthesis. J Mol Biol 10, 63-72 (1964).

Uno, M., Ito, K., and Nakamura, Y., (2002) Polypeptide release at sense and noncognate stop codons by localized charge-exchange alterations in translational release factors. *Proc Natl Acad Sci USA,* 99 (4): 1819-24.

Valle, M., Zavialov, A. V., Sengupta, J., Rawat, U., Ehrenberg, M., and Frank, J., (2003) Locking and unlocking of ribosomal motions. *Cell,* 114: 123-134.

Vestergaard, B., Sanyal, S., Roessle, M., Mora, L., Buckingham, R. H., Kastrup, J. S., Gajhede, M., Svergun, D. I., and Ehrenberg, M., (2005) The SAXS solution structure of RF1 differs from its crystal structure and is similar to its ribosome bound cryo-EM structure. *Mol Cell,* 20 (6): 929-38.

Wagner, K. R., Hamed, S., Hadley, D. W., Gropman, A. L., Burstein, A. H., Escolar, D. M., Hoffman, E. P., and Fischbeck, K. H., (2001) Gentamicin treatment of Duchenne and Becker muscular dystrophy due to nonsense mutations. *Ann Neurol,* 49 (6): 706-11.

Ware, M. D., DeSilva, D., Sinilnikova, O. M., Stoppa-Lyonnet, D., Tavtigian, S. V., and Mazoyer, S., (2006) Does nonsense-mediated mRNA decay explain the ovarian cancer cluster region of the BRCA2 gene? *Oncogene,* 25 (2): 323-8.

Weixlbaumer, A., Petry, S., Dunham, C. M., Selmer, M., Kelley, A. C., and Ramakrishnan, V., (2007) Crystal structure of the ribosome recycling factor bound to the ribosome. *Nat Struct Mol Biol,* 14 (8): 733-7.

Welch, E. M., Barton, E. R., Zhuo, J., Tomizawa, Y., Friesen, W. J., Trifillis, P., Paushkin, S., Patel, M., Trotta, C. R., Hwang, S., Wilde, R. G., Karp, G., Takasugi, J., Chen, G., Jones, S., Ren, H., Moon, Y. C., Corson, D., Turpoff, A. A., Campbell, J. A., Conn, M. M., Khan, A., Almstead, N. G., Hedrick, J., Mollin, A., Risher, N., Weetall, M., Yeh, S., Branstrom, A. A., Colacino, J. M., Babiak, J., Ju, W. D., Hirawat, S., Northcutt, V. J., Miller, L. L., Spatrick, P., He, F., Kawana, M., Feng, H., Jacobson, A., Peltz, S. W., and Sweeney, H. L., (2007) PTC124 targets genetic disorders caused by nonsense mutations. *Nature,* 447 (7140): 87-91.

Wilschanski, M., Yahav, Y., Yaacov, Y., Blau, H., Bentur, L., Rivlin, J., Aviram, M., Bdolah-Abram, T., Bebok, Z., Shushi, L., Kerem, B., and Kerem, E., (2003) Gentamicin induced correction of CFTR function in patients with cystic fibrosis and CFTR stop mutations. *N Engl J Med,* 349 (15): 1433-41.

Wilson, D. N., Blaha, G., Connell, S. R., Ivanov, P. V., Jenke, H., Stelzl, U., Teraoka, Y., and Nierhaus, K. H., (2002) Protein synthesis at atomic resolution: mechanistics of translation in the light of highly resolved structures for the ribosome. *Current Protein & Peptide Science,* 3 (1): 1-53.

Wilson, K. S., Ito, K., Noller, H. F., and Nakamura, Y., (2000) Functional sites of interaction between release factor RF1 and the ribosome. *Nat Struct Biol,* 7 (10): 866-870.

Wolf, M., Edgren, H., Muggerud, A., Kilpinen, S., Huusko, P., Sorlie, T., Mousses, S., and Kallioniemi, O., (2005) NMD microarray analysis for rapid genome-wide screen of mutated genes in cancer. *Cell Oncol*, 27 (3): 169-73.

Yang, H., Karnchanaphanurach, P., and Xie, S. N., (2002) Probing single-molecule conformation dynamics photon by photon. *Biophysical Journal 46th Annual Meeting of the Biophysical Society*; February 23-27, 2002; San Francisco, Calif., USA, 82 (1 Part 2): 192a-192A.

Youngman, E. M., He, S. L., Nikstad, L. J., and Green, R., (2007) Stop codon recognition by release factors induces structural rearrangement of the ribosomal decoding center that is productive for peptide release. *Mol Cell*, 28 (4): 533-43.

Youngman, E. M., Cochella, L., Brunelle, J. L., He, S., and Green, R., (2006) Two distinct conformations of the conserved RNA-rich decoding center of the small ribosomal subunit are recognized by tRNAs and release factors. *Cold Spring Harb Symp Quant Biol*, 71: 545-9.

Zavialov, A. V., Hauryliuk, V. V., and Ehrenberg, M., (2005) Splitting of the posttermination ribosome into subunits by the concerted action of RRF and EF-G. *Mol Cell*, 18 (6): 675-86.

Zavialov, A. V. & Ehrenberg, M. Peptidyl-tRNA regulates the GTPase activity of translation factors. Cell 114, 113-122 (2003).

Zavialov, A. V., Mora, L., Buckingham, R. H., and Ehrenberg, M., (2002) Release of peptide promoted by the GGQ motif of class 1 release factors regulates the GTPase activity of RF3. *Mol Cell*, 10 (4): 789-798.

Zavialov, A. V., Buckingham, R. H., and Ehrenberg, M., (2001) A posttermination ribosomal complex is the guanine nucleotide exchange factor for peptide release factor RF3. *Cell*, 107 (1): 115-124.

Zoldak, G., Redecke, L., Svergun, D. I., Konarev, P. V., Voertler, C. S., Dobbek, H., Sedlak, E., and Sprinzl, M., (2007) Release factors 2 from *Escherichia coli* and *Thermus thermophilus*: structural, spectroscopic and microcalorimetric studies. *Nucleic Acids Res*, 35 (4): 1343-53.

The invention claimed is:

1. A probe comprising a class 1 release factor (RF) conjugated to two fluorescent labels.

2. The probe of claim 1, wherein the class 1 RF is selected from the group consisting of RF1, RF2, and eRF 1.

3. The probe of claim 1, wherein the two fluorescent labels are a donor-acceptor pair.

4. The probe of claim 3, wherein the donor-acceptor pair is selected from the group consisting of coumarin 4/coumarin 343; 6-carboxyfluorescein/6-carboxy-X-rhodamine; 5,7-dimethyl-BODIPY/5-(4-phenyl-1,3-butadienyl)BODIPY; and Cy3/Cy5.

5. The probe of claim 1, wherein the fluorescent label comprises a fluorescein, a rhodamine, a cyanine, a coumarin, or a derivative thereof.

6. A method of making the class 1 RF conjugated to two fluorescent labels of claim 1, the method comprising:
   a) identifying at least two phylogenetically-variable amino acids in a class 1 RF sequence;
   b) mapping the phylogenetically-variable amino acids in the three-dimensional structure of the class 1 RF;
   c) removing all wildtype cysteine residues;
   d) replacing each of two phylogenetically-variable amino acids in an inactive region of the class 1 RF with a cysteine residue; and
   e) conjugating two fluorescent labels to the cysteine residues; thereby making the class 1 RF conjugated to two fluorescent labels of claim 1.

7. The method of claim 6, wherein the two fluorescent labels are a donor-acceptor pair.

8. The method of claim 7, further comprising:
   F) isolating class 1 RFs conjugated to a donor-acceptor pair.

9. The method of claim 8, wherein the isolating is by hydrophobic interaction chromatography.

10. A method of detecting a conformational change in a class 1 RF, the method comprising:
    a) providing a reaction mixture comprising an isolated, translationally-competent bacterial ribosome complex bound to a solid surface;
    b) adding to the reaction mixture a probe comprising the class 1 RF conjugated to a donor-acceptor pair of fluorescent labels of claim 3; and
    c) measuring fluorescence resonance energy transfer (FRET) efficiency between the donor-acceptor pair;
wherein a shift in FRET efficiency after adding the probe indicates a conformational change in the class 1 RF.

11. The method of claim 10, wherein the donor-acceptor pair is Cy3/Cy5.

12. A method of assaying RF3 activity, the method comprising:
    a) providing a reaction mixture comprising an isolated, translationally-competent bacterial ribosome complex bound to a solid surface;
    b) adding to the reaction mixture a probe comprising a class 1 RF conjugated to the donor-acceptor pair of fluorescent labels of claim 3;
    c) adding to the reaction mixture RF3; and
    d) measuring fluorescence resonance energy transfer (FRET) efficiency between the donor-acceptor pair by imaging the solid surface;
wherein a loss in FRET efficiency after adding the RF3 indicates RF3 activity by indicating release of the class 1 RF from the ribosome complex.

13. A method of assaying RF3 activity, the method comprising:
    a) providing a reaction mixture comprising an isolated, translationally-competent bacterial ribosome complex bound to a solid surface;
    b) adding to the reaction mixture a probe comprising a class 1 RF conjugated to the donor-acceptor pair of fluorescent labels of claim 3;
    c) adding to the reaction mixture RF3; and
    d) measuring fluorescence resonance energy transfer (FRET) efficiency between the donor-acceptor pair by imagining the reaction mixture;
wherein high FRET efficiency after adding the RF3 indicates RF3 activity by indicating release of the class 1 RF from the ribosome complex.

14. A method of identifying a compound for reducing nonsense-mediated decay of mRNA, the method comprising:
    a) providing a reaction mixture comprising an isolated, translationally-competent bacterial ribosome complex bound to a solid surface, wherein the reaction mixture comprises an mRNA comprising a premature stop codon;
    b) adding to the reaction mixture a candidate compound;
    c) adding to the reaction mixture a probe comprising a class 1 RF conjugated to the donor-acceptor pair of fluorescent labels of claim 3; and
    d) measuring fluorescence resonance energy transfer (FRET) efficiency between the donor-acceptor pair by imagining the reaction mixture;
wherein high FRET efficiency after adding the probe indicates that the candidate compound inhibits binding of the class 1 RF to the ribosome complex, thereby identifying a compound for reducing nonsense-mediated decay of mRNA.

15. A method of identifying a compound for reducing nonsense-mediated decay of mRNA, the method comprising:
    a) providing a reaction mixture comprising an isolated, translationally-competent bacterial ribosome complex bound to a solid surface, wherein the reaction mixture comprises an mRNA comprising a premature stop codon;
    b) adding to the reaction mixture a candidate compound;
    c) adding to the reaction mixture a probe comprising the class 1 RF conjugated to a donor-acceptor pair of fluorescent labels of claim 3; and
    d) measuring fluorescence resonance energy transfer (FRET) efficiency between the donor-acceptor pair by imaging the solid surface;

wherein lack of FRET efficiency or transient FRET efficiency after adding the probe indicates that the candidate compound inhibits binding of the class 1 RF to the ribosome complex, thereby identifying a compound for reducing nonsense-mediated decay of mRNA.

16. A method of identifying a compound for inhibiting termination of protein synthesis at a premature stop codon, the method comprising:
   a) providing a reaction mixture comprising an isolated, translationally-competent bacterial ribosome complex bound to a solid surface, wherein the ribosome complex comprises a first fluorescent label, and wherein the reaction mixture comprises an mRNA comprising a premature stop codon;
   b) adding to the reaction mixture a candidate compound;
   c) adding to the reaction mixture a probe comprising the class 1 RF conjugated to a donor-acceptor pair of fluorescent labels of claim 3; and
   d) measuring fluorescence resonance energy transfer (FRET) efficiency between the donor-acceptor pair by imaging the reaction mixture;
wherein high FRET efficiency after adding the probe indicates that the candidate compound inhibits binding of the class 1 RF to the ribosome complex, thereby identifying a compound for inhibiting termination of protein synthesis at a premature stop codon.

17. A method of identifying a compound for inhibiting termination of protein synthesis at a premature stop codon, the method comprising:
   a) providing a reaction mixture comprising an isolated, translationally-competent bacterial ribosome complex bound to a solid surface, wherein the ribosome complex comprises a first fluorescent label, and wherein the reaction mixture comprises an mRNA comprising a premature stop codon;
   b) adding to the reaction mixture a candidate compound;
   c) adding to the reaction mixture a probe comprising a class 1 RF conjugated to the donor-acceptor pair of fluorescent labels of claim 3; and
   d) measuring fluorescence resonance energy transfer (FRET) efficiency between the donor-acceptor pair by imaging the solid surface;
wherein lack of FRET efficiency or transient FRET efficiency after adding the probe indicates that the candidate compound inhibits binding of the class 1 RF to the ribosome complex, thereby identifying a compound for inhibiting termination of protein synthesis at a premature stop codon.

* * * * *

SEQUENCE LISTING

```
<160> NUMBER OF SEQ ID NOS: 10

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Ser Gly Gly Ser
1               5

<210> SEQ ID NO 2
<211> LENGTH: 6
<212> TYPE: RNA
<213> ORGANISM: Bovine immunodeficiency virus
<220> FEATURE:
<221> NAME/KEY: modified_base
<222> LOCATION: (1)..(1)
<223> OTHER INFORMATION: a, c, u, g, unknown or other
<220> FEATURE:
<221> NAME/KEY: modified_base
<222> LOCATION: (4)..(4)
<223> OTHER INFORMATION: a, c, u, g, unknown or other

<400> SEQUENCE: 2 nugngc                                                               6

<210> SEQ ID NO 3
<211> LENGTH: 10
<212> TYPE: PRT
<213> ORGANISM: Bovine immunodeficiency virus

<400> SEQUENCE: 3

Arg Gly Thr Arg Gly Lys Gly Arg Arg Ile
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 4

Glu Gln Lys Leu Ile Ser Glu Glu Asp Leu
1               5                   10

<210> SEQ ID NO 5
<211> LENGTH: 54
<212> TYPE: RNA
<213> ORGANISM: Enterobacteria phage T4

<400> SEQUENCE: 5
ggcaaccuaa aacuuacaca gggcccuaag gaaauaaaaa uguuuaaug uaaa          54

<210> SEQ ID NO 6
<211> LENGTH: 53
<212> TYPE: RNA
<213> ORGANISM: Enterobacteria phage T4

<400> SEQUENCE: 6
ucuacugcug aacucgcugc acaaauggcu aaacugaaug gcaauuaagg auc           53

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 3'-Biotin

<400> SEQUENCE: 7
tgtgtaagtt ttaggttgat ttg                                           23

<210> SEQ ID NO 8
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
auguuuaaac                                                          10

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 9

His His His His His His
1               5

<210> SEQ ID NO 10
<211> LENGTH: 5
<212> TYPE: RNA
<213> ORGANISM: Bovine immunodeficiency virus
<220> FEATURE:
<221> NAME/KEY: modified_base
<222> LOCATION: (3)..(3)
<223> OTHER INFORMATION: a, c, u, g, unknown or other
<220> FEATURE:
<221> NAME/KEY: modified_base
```

```
<222> LOCATION: (5)..(5)
<223> OTHER INFORMATION: a, c, u, g, unknown or other

<400> SEQUENCE: 10 gcncn                                                                    5
```